US011208369B2

(12) United States Patent
Petrovic et al.

(10) Patent No.: US 11,208,369 B2
(45) Date of Patent: Dec. 28, 2021

(54) HYDROFORMYLATED TRIGLYCERIDES AND USES THEREOF

(71) Applicant: Checkerspot, Inc., Berkeley, CA (US)

(72) Inventors: Zoran Petrovic, Pittsburg, KS (US); Jian Hong, Pittsburg, KS (US); Mihail Ionescu, Bucharest (RO)

(73) Assignee: Checkerspot, Inc., Alameda, CA (US)

( * ) Notice: Subject to any disclaimer, the term of this patent is extended or adjusted under 35 U.S.C. 154(b) by 0 days.

(21) Appl. No.: 17/185,368

(22) Filed: Feb. 25, 2021

(65) Prior Publication Data

US 2021/0230651 A1 Jul. 29, 2021

Related U.S. Application Data

(63) Continuation of application No. PCT/US2019/048751, filed on Aug. 29, 2019.
(Continued)

(51) Int. Cl.
| | |
|---|---|
| *C07C 31/18* | (2006.01) |
| *C07C 29/141* | (2006.01) |
| *C07C 45/50* | (2006.01) |
| *C07C 29/16* | (2006.01) |
| *C07C 29/17* | (2006.01) |
| *C07C 47/20* | (2006.01) |

(Continued)

(52) U.S. Cl.
CPC ............ *C07C 31/18* (2013.01); *C07C 29/141* (2013.01); *C07C 29/16* (2013.01); *C07C 29/17* (2013.01); *C07C 45/50* (2013.01); *C07C 47/20* (2013.01); *C07C 67/02* (2013.01); *C07C 67/03* (2013.01); *C08G 18/00* (2013.01); *C08G 18/10* (2013.01); *C12P 7/6463* (2013.01); *C07C 67/31* (2013.01); *C07C 67/347* (2013.01); *C08G 2101/00* (2013.01); *C08G 2170/00* (2013.01); *C12P 7/6427* (2013.01)

(58) Field of Classification Search
CPC ....... C07C 29/16; C07C 29/141; C07C 47/20; C07C 45/50; C07C 31/18; C07C 29/17141; C08G 18/00; C08G 18/10; C08G 2101/00; C08G 2170/00
See application file for complete search history.

(56) References Cited

U.S. PATENT DOCUMENTS

| | | |
|---|---|---|
| 4,248,802 A | 2/1981 | Kuntz |
| 4,483,802 A | 11/1984 | Gartner et al. |

(Continued)

FOREIGN PATENT DOCUMENTS

| | | |
|---|---|---|
| WO | WO-2008151149 A2 | 12/2008 |
| WO | WO-2010006032 A1 | 1/2010 |

(Continued)

OTHER PUBLICATIONS

Petrovic, Z.S., et al., Polyols and polyurethanes from crude algal oil, J. Am. Oil Chem. Soc., vol. 90, issue 7, pp. 1073-1078 (Year: 2013).*

(Continued)

*Primary Examiner* — Yate' K Cutliff
(74) *Attorney, Agent, or Firm* — Wilson Sonsini Goodrich & Rosati

(57) ABSTRACT

This disclosure provides methods for the chemical modification of triglycerides that are highly enriched in specific fatty acids and subsequent use thereof for producing functionally versatile polymers.

20 Claims, 31 Drawing Sheets

Related U.S. Application Data

(60) Provisional application No. 62/725,214, filed on Aug. 30, 2018.

(51) Int. Cl.
| | |
|---|---|
| *C07C 67/02* | (2006.01) |
| *C07C 67/03* | (2006.01) |
| *C08G 18/00* | (2006.01) |
| *C08G 18/10* | (2006.01) |
| *C12P 7/64* | (2006.01) |
| *C07C 67/31* | (2006.01) |
| *C07C 67/347* | (2006.01) |
| *C08G 101/00* | (2006.01) |

(56) References Cited

U.S. PATENT DOCUMENTS

| | | | |
|---|---|---|---|
| RE31,812 E | 1/1985 | Kuntz | |
| 6,107,433 A | 8/2000 | Petrovic et al. | |
| 6,180,686 B1 | 1/2001 | Kurth et al. | |
| 6,414,172 B1 * | 7/2002 | Garces | A01H 5/10 554/227 |
| 8,871,985 B2 * | 10/2014 | Van Vliet | C07C 29/141 568/882 |
| 9,000,062 B2 | 4/2015 | Albach et al. | |
| 2010/0311992 A1 * | 12/2010 | Petrovic | C08G 18/36 549/539 |
| 2011/0015292 A1 | 1/2011 | Radhakrishnan et al. | |
| 2016/0002566 A1 | 1/2016 | Vanhercke et al. | |
| 2016/0194584 A1 | 7/2016 | Ngantung et al. | |
| 2018/0127350 A1 | 5/2018 | Hapiot et al. | |
| 2018/0237811 A1 * | 8/2018 | Franklin | A23D 9/00 |

FOREIGN PATENT DOCUMENTS

| | | |
|---|---|---|
| WO | WO-2010063031 A2 | 6/2010 |
| WO | WO-2010120923 A1 | 10/2010 |
| WO | WO-2010120939 A2 | 10/2010 |
| WO | WO-2011150410 A2 | 12/2011 |
| WO | WO-2012061647 A2 | 5/2012 |
| WO | WO-2012106560 A1 | 8/2012 |
| WO | WO-2013082186 A2 | 6/2013 |
| WO | WO-2013158938 A1 | 10/2013 |
| WO | WO-2014176515 A2 | 10/2014 |
| WO | WO-2015051319 A2 | 4/2015 |
| WO | WO-2020047216 A1 | 3/2020 |

OTHER PUBLICATIONS

Uprety B. K., et al., Utilization of microbial oil obtained from crude glycerol for the production of polyol and its subsequent conversion to polyurethane foams, Bioresource Technology, No. 235, pp. 309-315 (Year: 2017).*

Acero, Polyurethane foams from renewable and sustainable polyols. Portugal: Instituto Superior Tecnico (2014).

Lin et al. Genetic engineering of microorganisms for biodiesel production. Bioengineered. Sep. 1, 2013; 4(5): 292-304. Published online Dec. 6, 2012. doi: 10.4161/bioe.23114.

McDonald. Surfing into a Greener Future. UC San Diego News Center. Apr. 23, 2015. 4 pages. URL: https://ucsdnews.ucsd.edu/feature/surfing_into_a_greener_future.

PCT/US2019/048751 International Search Report and Written Opinion dated Dec. 31, 2019.

Petrović et al. Polyols and Polyurethanes from Crude Algal Oil. Journal of the American Oil Chemists' Society, vol. 90, Issue 7, pp. 1073-1078 (Jul. 2013). First published Apr. 18, 2013. doi: https://doi.org/10.1007/s11746-013-2245-9.

Petrović. Polyurethanes from Vegetable Oils. Polymer Reviews 48:109-155 (2008).

Shi et al. Metabolic Engineering of Oleaginous Yeasts for Production of Fuels and Chemicals. Front Microbiol. 2017; 8: 2185. Published online Nov. 8, 2017. doi: 10.3389/fmicb.2017.02185. 16 pages.

Uprety et al. Utilization of microbial oil obtained from crude glycerol for the production of polyol and its subsequent conversion to polyurethane foams. Biosour Technol. Jul. 2017;235:309-315. doi: 10.1016/j.biortech.2017.03.126. Epub Mar. 24, 2017.

Zhang et al. Bio-based Polyurethane Foam Made from Compatible Blends of Vegetable-Oil-based Polyol and Petroleum-based Polyol. ACS Sustainable Chem Eng 3:743-749 (Mar. 6, 2015).

* cited by examiner

HYDROFORMYLATED TRIGLYCERIDES AND USES THEREOF

CROSS REFERENCE

This application is a continuation of PCT/US2019/048751, filed Aug. 29, 2019, which claims the benefit of U.S. Provisional Application No. 62/725,214, filed on Aug. 30, 2018, each of which is incorporated herein by reference in its entirety.

BACKGROUND

Polyurethanes can be produced via the condensation of a hydroxyl functionality, such as a polyol, with an isocyanate moiety. As a polymer class, polyurethanes are quite diverse and unique among plastics as the chemical structure of polyurethanes is not highly repetitive in nature. As a consequence, polyurethanes having the same general physical properties can have dramatically different chemical compositions. Because of their diverse structural makeup, polyurethanes come in myriad forms and are used for the production of films, coatings, hard and soft foams, sealants, adhesives, and elastomers.

Most polyols are typically derived from petroleum feedstocks. However, as the global climate continues to warm, and with little doubt remaining as to the direct correlation between the increased utilization of fossil fuels over the past millennium and the imminent threat posed by a warming climate, there is an urgent need to replace incumbent, petroleum derived fuels and chemicals with more sustainable, renewable materials. The polyol components of polyurethanes present an opportunity for renewable alternatives with novel functionalities.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

SUMMARY

Figure 1:
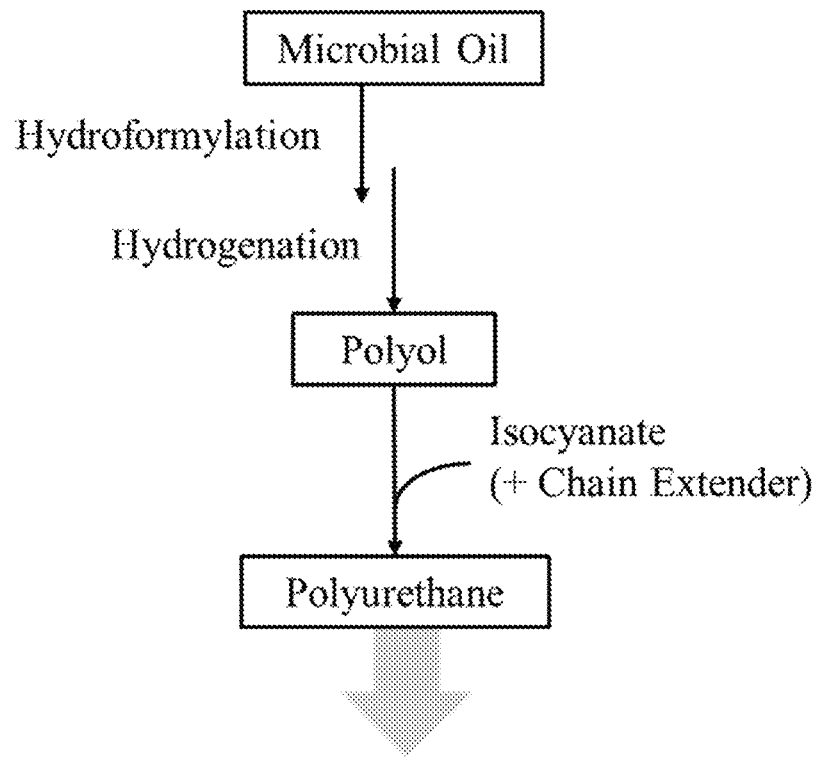
FIG. 1 illustrates a schematic of the production of polyurethane products from microbial oil.

In some aspects, the present disclosure provides a method of producing a hydroformylated polyol, comprising: (a) obtaining a microbial oil comprising triacylglycerol (TAG) species having a fatty acid profile comprising at least 60% of one or more unsaturated fatty acids; and (b) hydroformylating and hydrogenating the one or more unsaturated fatty acids, thereby generating the hydroformylated polyol.

In some aspects, the present disclosure provides a method of producing a hydroformylated polyol, comprising: (a) obtaining a microbial oil comprising up to nine TAG species present in amounts of 1% or more in the microbial oil, wherein the up to nine TAG species present in amounts of 1% or more have a fatty acid profile comprising one or more unsaturated fatty acids; and (b) hydroformylating and hydrogenating the one or more unsaturated fatty acids, thereby generating the hydroformylated polyol.

In some embodiments, the microbial oil comprises up to nine TAG species. In some embodiments, the microbial oil consists essentially of up to nine TAG species. In some embodiments, the microbial oil comprises up to four TAG species. In some embodiments, microbial oil consists essentially of up to four TAG species.

In some embodiments, the microbial oil comprises up to two TAG species comprising at least about 85% of total TAG species. In some embodiments, the microbial oil consists of one TAG species comprising at least about 85% of total TAG species. In some embodiments, the microbial oil consists of one TAG species comprising at least about 65% of total TAG species. In some embodiments, the microbial oil consists of one TAG species comprising at least about 88% of total TAG species.

In some embodiments, the fatty acid profile comprises at least 60% of the one or more unsaturated fatty acids. In some embodiments, the fatty acid profile comprises at least 65% of the one or more unsaturated fatty acids. In some embodiments, the fatty acid profile comprises at least 70% of the one or more unsaturated fatty acids. In some embodiments, the fatty acid profile comprises at least 75% of the one or more unsaturated fatty acids. In some embodiments, the fatty acid profile comprises at least 80% of the one or more unsaturated fatty acids. In some embodiments, the fatty acid profile comprises at least 85% of the one or more unsaturated fatty acids. In some embodiments, the fatty acid profile comprises at least 90% of the one or more unsaturated fatty acids. In some embodiments, the fatty acid profile comprises at least 95% of the one or more unsaturated fatty acids.

In some embodiments, the unsaturated fatty acid species is selected from the group consisting of myristoleic acid, palmitoleic acid, sapienic acid, oleic acid, elaidic acid, vaccenic acid, petroselinic acid, eicosenoic (gondoic) acid, paullinic acid, gadoleic acid, erucic acid, brassidic acid, nervonic acid, hexadecatrienoic acid, linoleic acid, linolelaidic acid, α-linolenic acid, pinolenic acid, stearidonic acid, eicosadienoic acid, mead acid, eicosatrienoic acid, dihomo-γ-linolenic acid, podocarpic acid, arachidonic acid, eicosatetraenoic acid, eicosapentaenoic acid, heneicosapentaenoic acid, docosadienoic acid, adrenic acid, docosapentaenoic acid (osbond acid), docosahexaenoic acid, docosahexaenoic acid, tetracosatetraenoic acid, and tetracosapentaenoic acid. In some embodiments, the unsaturated fatty acid species is an 18:1 fatty acid. In some embodiments, the fatty acid profile comprises from 65% to 97% of an 18:1 fatty acid. In some embodiments, the fatty acid profile comprises from 85% to 95% of an 18:1 fatty acid.

In some embodiments, the TAG species comprises 60% or more of a first TAG species. In some embodiments, the TAG species comprises 60% to 95% of a first TAG species. In some embodiments, the TAG species comprises 85% or more of a first TAG species. In some embodiments, the TAG species comprises 90% or more of a first TAG species. In some embodiments, the TAG species comprises 95% or more of a first TAG species.

In some embodiments, the first TAG species is selected from the group consisting of: OOO, LLL, LnLnLn, LLP, LPL, LnLnP, LnPLn, and any regioisomer thereof, wherein O is olein, L is linolein, Ln is linolenin, and P is palmitin. In some embodiments, the first TAG species is triolein (OOO). In some embodiments, the TAG species comprises 30% or more of triolein. In some embodiments, the TAG species comprises 60% or more of triolein. In some embodiments, the TAG species comprises 65% or more of triolein. In some embodiments, the TAG species comprises 70% or more of triolein. In some embodiments, the TAG species comprises 75% or more of triolein. In some embodiments, the TAG species comprises 80% or more of triolein. In some embodiments, the TAG species comprises 85% or more of triolein. In some embodiments, the TAG species comprises 90% or more of triolein. In some embodiments, the TAG species comprises 95% or more of triolein.

In some embodiments, the microbial oil comprises 60% or more of an 18:1 fatty acid and 30% or less of one or more saturated fatty acids. In some embodiments, the microbial oil comprises 60% or more of an 18:1 fatty acid, 30% or less of one or more saturated fatty acids, and at least one unsaturated fatty acid in a remainder. In some embodiments, the microbial oil comprises at least 85% oleate and up to 5% linoleate. In some embodiments, the microbial oil comprises at least 85% oleate, up to 5% linoleate, and up to 1.8% palmitate. In some embodiments, the microbial oil comprises 91% or more of an 18:1 fatty acid. In some embodiments, the 18:1 fatty acid is oleic acid.

In some embodiments, the fatty acid profile comprises: at least 60% of an 18:1 fatty acid and up to 15% of one or more other unsaturated fatty acids selected from the group consisting of: a 16:1 fatty acid, an 18:2 fatty acid, an 18:3 fatty acid, and any combination thereof. In some embodiments, the fatty acid profile comprises: at least 60% of an 18:1 fatty acid, up to 10% of an 18:2 fatty acid, and up to 20% of a 16:0 fatty acid. In some embodiments, the fatty acid profile comprises: at least 70% of an 18:1 fatty acid, up to 8% of an 18:2 fatty acid, and up to 12% of a 16:0 fatty acid. In some embodiments, the fatty acid profile comprises: at least 80% of an 18:1 fatty acid, up to 8% of an 18:2 fatty acid, and up to 5% of a 16:0 fatty acid. In some embodiments, the one or more unsaturated fatty acids comprise a plurality of different unsaturated fatty acids. In some embodiments, the one or more unsaturated fatty acids is one unsaturated fatty acid species.

In some embodiments, the microbial oil is from microalgae. In some embodiments, the microalgae is a species of a genus selected from the group consisting of: *Chlorella* sp., *Pseudochlorella* sp., *Heterochlorella* sp., *Prototheca* sp., *Arthrospira* sp., *Euglena* sp., *Nannochloropsis* sp., *Phaeodactylum* sp., *Chlamydomonas* sp., *Scenedesmus* sp., *Ostreococcus* sp., *Selenastrum* sp., *Haematococcus* sp., *Nitzschia, Dunaliella, Navicula* sp., *Trebouxia* sp., *Pseudotrebouxia* sp., *Vavicula* sp., *Bracteococcus* sp., *Gomphonema* sp., *Watanabea*, sp., *Botryococcus* sp., *Tetraselmis* sp., and *Isochrysis* sp. In some embodiments, the microbial oil is from *Prototheca* sp. In some embodiments, the microbial oil is from *P. moriformis*.

In some embodiments, the microbial oil is from oleaginous yeast. In some embodiments, the oleaginous yeast is a species of a genus selected from the group consisting of: *Candida* sp., *Cryptococcus* sp., *Debaromyces* sp., *Endomycopsis* sp., *Geotrichum* sp., *Hyphopichia* sp., *Lipomyces* sp., *Pichia* sp., *Rodosporidium* sp., *Rhodotorula*, sp., *Sporobolomyces* sp., *Starmerella* sp., *Torulaspora* sp., *Trichosporon* sp., *Wickerhamomyces* sp., *Yarrowia* sp., and *Zygoascus* sp.

In some embodiments, the microbial oil is from oleaginous bacteria. In some embodiments, the oleaginous bacteria is a species selected from the group consisting of: *Flavimonas oryzihabitans, Pseudomonas aeruginosa, Morococcus* sp., *Rhodobacter sphaeroides, Rhodococcus opacus, Rhodococcus erythropolis, Streptomyces jeddahensis, Ochrobactrum* sp., *Arthrobacter* sp., *Nocardia* sp., *Mycobacteria* sp., *Gordonia* sp., *Catenisphaera* sp., and *Dietzia* sp.

In some embodiments, the microbial oil is derived from a genetically modified microbe. In some embodiments, the genetically modified microbe is genetically modified from a microbe selected from the group consisting of: microalgae, oleaginous yeast, and oleaginous bacteria. In some embodiments, the genetically modified microbe is a genetically modified *Prototheca* sp. strain.

In some embodiments, the hydroformylation is performed at a temperature of from about 80° C. to about 120° C. In some embodiments, the hydroformylation is performed at a pressure of from about 800 psi to about 1200 psi. In some embodiments, the hydroformylation is performed at a pressure of about 1000 psi. In some embodiments, the hydroformylation is performed at a temperature of about 90° C. In some embodiments, the hydroformylation is performed at a temperature of about 90° C. and a pressure of about 1000 psi. In some embodiments, the hydroformylation occurs in the presence of carbon monoxide gas and a catalyst. In some embodiments, the catalyst is selected from the group consisting of: cobalt-based catalysts, cobalt tetracarbonyl hydride, cobalt phosphine catalysts, cobalt supplemented with various noble metals (e.g., palladium, ruthenium, and platinum), rhodium-based catalysts, rhodium phosphine catalysts, acetylacetonato-dicarbonylrhodium(I) (Rh(CO)$_2$acac), rhodium/cyclohexyl diphenylphosphine (Rh/CHDPP), and any transition metal-based catalyst suitable for hydroformylation. In some embodiments, the hydrogenation comprises reduction with hydrogen gas to yield the hydroformylated polyol.

In some embodiments, the hydroformylated polyol comprises a primary —OH. In some embodiments, the hydroformylated polyol has a hydroxyl number of from 90 to 182. In some embodiments, the hydroformylated polyol has a hydroxyl number of from 150 to 165. In some embodiments, the hydroformylated polyol has a hydroxyl number of from 170 to 175.

In some embodiments, the method further comprises, prior to (b), methylating the TAG species to yield fatty acid methyl esters, wherein the fatty acid methyl esters comprise one or more unsaturated fatty acids. In some embodiments, the method further comprises, following (b), methylating the hydroformylated polyol to yield hydroformylated polyol methyl esters. In some embodiments, the method further comprises, prior to (b), hydrogenating the TAG species to yield partially saturated fatty acids.

In some embodiments, the hydrogenation is performed at a temperature of from about 90° C. to about 110° C. In some embodiments, the hydrogenation is performed at a pressure of from about 600 psi to about 1200 psi.

In some embodiments, the method further comprises, polymerizing the hydroformylated polyol to yield a polymer of polymerized hydroformylated polyols.

In some embodiments, the polymer is rigid. In some embodiments, the polymerization comprises reacting an amount of isocyanate with the hydroformylated polyol to yield the polymer, wherein the polymer is a pre-polymer comprising at least one isocyanate.

In some embodiments, the polyurethane is a resin. In some embodiments, the polyurethane is a resin having a tensile strength of about 0.04 MPa to about 70 MPa and an elongation at break of about 2% to about 300%. In some embodiments, the polyurethane is a foam. In some embodiments, the foam is a hard foam. In some embodiments, the hard foam has a density of about 15 kg/m$^3$ to about 50 kg/m$^3$. In some embodiments, the hard foam has a density of about 20 kg/m$^3$ to about 200 kg/m$^3$. In some embodiments, the hard foam has a density of about 15 kg/m$^3$, about 16 kg/m$^3$, about 17 kg/m$^3$, about 18 kg/m$^3$, about 19 kg/m$^3$, about 20 kg/m$^3$, about 25 kg/m$^3$, about 30 kg/m$^3$, about 35 kg/m$^3$, about 40 kg/m$^3$, about 45 kg/m$^3$, about 50 kg/m$^3$, about 55 kg/m$^3$, about 60 kg/m$^3$, about 65 kg/m$^3$, about 70 kg/m$^3$, about 75 kg/m$^3$, about 80 kg/m$^3$, about 85 kg/m$^3$, about 90 kg/m$^3$, about 95 kg/m$^3$, about 100 kg/m$^3$, about 105 kg/m$^3$, about 110 kg/m$^3$, about 115 kg/m$^3$, about 120 kg/m$^3$, about 125 kg/m$^3$, about 130 kg/m$^3$, about 135 kg/m$^3$, about 140 kg/m$^3$, about 145 kg/m$^3$, about 150 kg/m$^3$, about 155 kg/m$^3$, about 160 kg/m$^3$, about 165 kg/m$^3$, about 170 kg/m$^3$, about 175 kg/m$^3$, about 180 kg/m$^3$, about 185 kg/m$^3$, about 190 kg/m$^3$, about 195 kg/m$^3$, or about 200 kg/m$^3$. In some embodiments, the hard foam has a compressive strength of from about 60 kPa to 1500 kPa. In some embodiments, the hard foam has a compressive strength of about 200 kPa to about 1100 kPa. In some embodiments, the hard foam has a compressive strength of about 50 kPa, about 60 kPa, about 75 kPa, about 90, kPa, about 100 kPa, about 150 kPa, about 200 kPa, about 300 kPa, about 400 kPa, about 500 kPa, about 600 kPa, about 700 kPa, about 800 kPa, about 900 kPa, about 1000 kPa, about 1100 kPa, about 1200 kPa, about 1300 kPa, about 1400 kPa, or about 1500 kPa.

In some embodiments, the method further comprises producing a product comprising the hard foam, wherein the product is selected from the group consisting of: surfboards, paddleboards, insulated coolers, housing insulation, automotive parts, aerospace foam, watercraft foam, marine insulation, structural foams, windmill blades, signage, movie set display foam, foam rollers, lightweight aircrafts, and lightweight watercraft. In some embodiments, the method further comprises producing a product from the hard foam, wherein the product is selected from the group consisting of: surfboards, paddleboards, insulated coolers, housing insulation, automotive parts, aerospace foam, watercraft foam, marine insulation, structural foams, windmill blades, signage, movie set display foam, foam rollers, lightweight aircrafts, and lightweight watercraft.

In some embodiments, the method further comprises reacting the polymerized hydroformylated polyols with isocyanate to yield a polyurethane elastomer. In some embodiments, the method further comprises reacting the polymerized hydroformylated polyols with a chain extender and isocyanate to yield a polyurethane elastomer. In some embodiments, the polyurethane elastomer comprises a soft segment concentration of about 20% to about 70%. In some embodiments, the polymerization comprises reacting the hydroformylated polyols with 1,6-hexanediol to yield a polyester, and producing the polyurethane elastomer comprises reacting the polyester with isocyanate and a chain extender. In some embodiments, the chain extender is selected from the group consisting of: ethylene glycol, diethylene glycol, triethylene glycol, tetraethylene glycol, propylene glycol (1,3-propanediol), dipropylene glycol, tripropylene glycol, neopentyl glycol, an alkyl diol, 1,3-butanediol, 1,4-butanediol, 1,6-pentanediol, 1,6-hexanediol, 1,2,6-hexanetriol, 1,4-cyclohexanedimethanol, ethanolamine, diethanolamine, methyldiethanolamine, phenyldiethanolamine, triethanolamine, isosorbide, glycerol, trimethylolpropane, pentaerythritol, diethyltoluenediamine, dimethylthiotoluenediamine, N,N,N',N'-tetrakis, glycerol, monoacylglycerol, diacylglycerol, and hydroquinone bis(2-hydroxyethyl) (HQEE). In some embodiments, the chain extender is 1,4-butanediol.

In some embodiments, the method comprises producing a polyurethane elastomer by: (i) generating a polyester by reacting the hydroformylated polyols with 1,6-hexanediol and a catalyst; (ii) generating a pre-polymer by reacting the polyester with a titrated amount of an isocyanate; and (iii) generating the polyurethane elastomer by reacting the pre-polymer with a chain extender. In some embodiments, the pre-polymer is a hydroxyl-terminated pre-polymer.

In some embodiments, polymerizing of hydroformylated polyols comprises transesterification of the hydroformylated polyols. In some embodiments, polymerizing the hydroformylated polyols comprises transesterification of the hydroformylated polyols with a chain extender and a catalyst to yield polyester diols. In some embodiments, the chain extender is selected from the group consisting of: ethylene glycol, diethylene glycol, triethylene glycol, tetraethylene glycol, propylene glycol (1,3-propanediol), dipropylene glycol, tripropylene glycol, neopentyl glycol, an alkyl diol, 1,3-butanediol, 1,4-butanediol, 1,6-pentanediol, 1,6-hexanediol, 1,2,6-hexanetriol, 1,4-cyclohexanedimethanol, ethanolamine, diethanolamine, methyldiethanolamine, phenyldiethanolamine, triethanolamine, isosorbide, glycerol, monoacylglycerol, diacylglycerol, trimethylolpropane, pentaerythritol, diethyltoluenediamine, dimethylthiotoluenediamine, N,N,N',N'-tetrakis, isosorbide, and hydroquinone bis (2-hydroxyethyl) (HQEE). In some embodiments, the catalyst is selected from the group consisting of: amine catalysts, tin catalysts, and bismuth catalysts. In some embodiments, the catalyst is titanium isopropoxide.

In some embodiments, the method further comprises reacting the polymerized hydroformylated polyols with isocyanate to yield a polyurethane adhesive. In some embodiments, a catalyst is not used in the reaction.

In some aspects, the present disclosure provides a method for producing a polymer comprising at least one urethane group, comprising: reacting at least one isocyanate with at least one hydroformylated polyol derived from a microbial oil comprising fatty acids, which fatty acids comprise 50% or more of unsaturated fatty acids, thereby generating the polymer.

In some aspects, the present disclosure provides a method for manufacturing polyurethane from microbial oil, the method comprising: (a) cultivating a population of microbes, which microbes are capable of producing oil comprising triglycerides, which triglycerides comprise 50% or more of one or more unsaturated fatty acids; (b) obtaining the oil from the microbes to yield microbial oil; (c) methylating the triglycerides of the microbial oil to yield fatty acid methyl esters; (d) hydroformylating and hydrogenating the fatty acid methyl esters to yield hydroformylated polyols; (e) reacting the hydroformylated polyols with isocyanate to yield the polyurethane.

In some aspects, the present disclosure provides an oil composition comprising: (a) hydroformylated polyols; and (b) up to nine TAG species having a fatty acid profile comprising at least 60% of one or more unsaturated fatty acids.

In some embodiments, the oil has up to nine TAG species. In some embodiments, the oil has up to four TAG species. In some embodiments, the oil has up to two TAG species. In some embodiments, the fatty acid profile comprises 63% or more of an unsaturated fatty acid species. In some embodiments, the fatty acid profile comprises 65% or more of an unsaturated fatty acid species. In some embodiments, the fatty acid profile comprises 70% or more of an unsaturated fatty acid species. In some embodiments, the fatty acid profile comprises 75% or more of an unsaturated fatty acid species. In some embodiments, the fatty acid profile comprises 80% or more of an unsaturated fatty acid species. In some embodiments, the fatty acid profile comprises 85% or more of an unsaturated fatty acid species. In some embodiments, the fatty acid profile comprises 90% or more of an unsaturated fatty acid species. In some embodiments, the fatty acid profile comprises 95% or more of an unsaturated fatty acid species. In some embodiments, the unsaturated fatty acid species is selected from the group consisting of: a 16:1 fatty acid, a 16:2 fatty acid, a 16:3 fatty acid, an 18:1 fatty acid, an 18:2 fatty acid, an 18:3 fatty acid, an 18:4 fatty acid, a 20:1 fatty acid, a 20:2 fatty acid, a 20:3 fatty acid, a 22:1 fatty acid, a 22:2 fatty acid, a 22:3 fatty acid, a 24:1 fatty acid, a 24:2 fatty acid, and a 24:3 fatty acid. In some embodiments, the unsaturated fatty acid species is an 18:1 fatty acid.

In some embodiments, the fatty acid profile comprises 63% or more of a first TAG species. In some embodiments, the fatty acid profile comprises 65% or more of a first TAG species. In some embodiments, the fatty acid profile comprises 70% or more of a first TAG species. In some embodiments, the fatty acid profile comprises 75% or more of a first TAG species. In some embodiments, the fatty acid profile comprises 80% or more of a first TAG species. In some embodiments, the fatty acid profile comprises 85% or more of a first TAG species. In some embodiments, the fatty acid profile comprises 90% or more of a first TAG species. In some embodiments, the fatty acid profile comprises 95% or more of a first TAG species.

In some embodiments, the unsaturated fatty acid species is selected from the group consisting of: a 16:1 fatty acid, a 16:2 fatty acid, a 16:3 fatty acid, an 18:1 fatty acid, an 18:2 fatty acid, an 18:3 fatty acid, an 18:4 fatty acid, a 20:1 fatty acid, a 20:2 fatty acid, a 20:3 fatty acid, a 22:1 fatty acid, a 22:2 fatty acid, a 22:3 fatty acid, a 24:1 fatty acid, a 24:2 fatty acid, and a 24:3 fatty acid. In some embodiments, the unsaturated fatty acid species is an 18:1 fatty acid.

In some embodiments, the TAG species comprises 60% or more of a first TAG species. In some embodiments, the TAG species comprises 65% or more of a first TAG species. In some embodiments, the TAG species comprises 70% or more of a first TAG species. In some embodiments, the TAG species comprises 75% or more of a first TAG species. In some embodiments, the TAG species comprises 80% or more of a first TAG species. In some embodiments, the TAG species comprises 85% or more of a first TAG species. In some embodiments, the TAG species comprises 90% or more of a first TAG species. In some embodiments, the TAG species comprises 95% or more of a first TAG species. In some embodiments, the first TAG species is selected from the group consisting of: OOO, LLL, LnLnLn, LLP, LPL, LnLnP, LnPLn, and any regioisomer thereof, wherein O is olein, L is linolein, Ln is linolenin, and P is palmitin. In some embodiments, the first TAG species is triolein (OOO).

In some embodiments, the fatty acid profile comprises the one or more unsaturated fatty acids and one or more saturated fatty acids, wherein at least 60% or more of the one or more unsaturated fatty acids in the fatty acid profile are 18:1 fatty acids and up to 30% of fatty acids in the fatty acid profile are the one or more saturated fatty acids. In some embodiments, the fatty acid profile comprises the one or more unsaturated fatty acids and one or more saturated fatty acids, wherein at least 60% or more of the one or more unsaturated fatty acids in the fatty acid profile are 18:1 fatty acids, up to 30% of fatty acids in the fatty acid profile are the one or more saturated fatty acids, and at least one unsaturated fatty acid in a remainder. In some embodiments, the fatty acid profile comprises at least 85% oleate and up to 5% linoleate. In some embodiments, the fatty acid profile comprises at least 85% oleate, up to 5% linoleate, and up to 1.8% palmitate. In some embodiments, the fatty acid profile comprises 91% or more of oleate or an 18:1 fatty acid. In some embodiments, the wherein the fatty acid profile comprises: at least 60% of an 18:1 fatty acid and up to 15% of one or more other unsaturated fatty acids selected from the group consisting of: a 16:1 fatty acid, an 18:2 fatty acid, an 18:3 fatty acid, or any combination thereof. In some embodiments, the fatty acid profile comprises: at least 60% of an 18:1 fatty acid, up to 10% of an 18:2 fatty acid, and up to 20% of a 16:0 fatty acid. In some embodiments, the fatty acid profile comprises: at least 70% of an 18:1 fatty acid, up to 8% of an 18:2 fatty acid, and up to 12% of a 16:0 fatty acid. In some embodiments, the fatty acid profile comprises: at least 80% of an 18:1 fatty acid, up to 8% of an 18:2 fatty acid, and up to 5% of a 16:0 fatty acid.

In some embodiments, the oil is a microbial oil. In some embodiments, the microbial oil is derived from microalgae. In some embodiments, the microalgae is a species of a genus selected from the group consisting of: *Chlorella* sp., *Pseudochlorella* sp., *Heterochlorella* sp., *Prototheca* sp., *Arthrospira* sp., *Euglena* sp., *Nannochloropsis* sp., *Phaeodactylum* sp., *Chlamydomonas* sp., *Scenedesmus* sp., *Ostreococcus* sp., *Selenastrum* sp., *Haematococcus* sp., *Nitzschia, Dunaliella, Navicula* sp., *Trebouxia* sp., *Pseudotrebouxia* sp., *Vavicula* sp., *Bracteococcus* sp., *Gomphonema* sp., *Watanabea*, sp., *Botryococcus* sp., *Tetraselmis* sp., and *Isochrysis* sp. In some embodiments, the microbial oil is derived from microalgae, wherein the microalgae is *Prototheca* sp. In some embodiments, the microbial oil is derived from microalgae, wherein the microalgae is *P. moriformis*.

In some embodiments, the microbial oil is derived from oleaginous yeast. In some embodiments, the oleaginous yeast is a species of a genus selected from the group consisting of: *Candida* sp., *Cryptococcus* sp., *Debaromyces* sp., *Endomycopsis* sp., *Geotrichum* sp., *Hyphopichia* sp., *Lipomyces* sp., *Pichia*, sp., *Rodosporidium* sp., *Rhodotorula* sp., *Sporobolomyces* sp., *Starmerella* sp., *Torulaspora* sp., *Trichosporon* sp., *Wickerhamomyces* sp., *Yarrowia* sp., and *Zygoascus* sp.

In some embodiments, the microbial oil is from oleaginous bacteria. In some embodiments, the oleaginous bacteria is a species selected from the group consisting of: *Flavimonas oryzihabitans, Pseudomonas aeruginosa, Morococcus* sp., *Rhodobacter sphaeroides, Rhodococcus opacus, Rhodococcus erythropolis, Streptomyces jeddahensis, Ochrobactrum* sp., *Arthrobacter* sp., *Nocardia* sp., *Mycobacteria* sp., *Gordonia* sp., *Catenisphaera* sp., and *Dietzia* sp.

In some embodiments, the microbial oil is derived from a genetically modified microbe. In some embodiments, the genetically modified microbe is genetically modified from a microbe selected from the group consisting of: microalgae, oleaginous yeast, and oleaginous bacteria. In some embodiments, the genetically modified microbe is a genetically modified *Prototheca* sp. strain.

In some aspects, the present disclosure provides a composition comprising: hydroformylated polyols each comprising a primary hydroxyl group, the hydroformylated polyols derived from a microbial oil, wherein the microbial oil comprises at least 60% of one or more unsaturated fatty acids and up to nine TAG species.

In some embodiments, the one or more unsaturated fatty acids comprise 60% or more of an 18:1 fatty acid.

In some aspects, the present disclosure provides a composition comprising: urethane and one or more hydroformylated polyols derived from microbial oil comprising 60% or more of one or more unsaturated fatty acids and/or up to nine TAG species.

In some aspects, the present disclosure provides a hard foam composition comprising: urethane and one or more hydroformylated polyols derived from a microbial oil comprising 60% or more of one or more unsaturated fatty acids and/or up to nine TAG species, wherein the hard foam has a density of about 15 kg/m$^3$ to about 50 kg/m$^3$.

In some aspects, the present disclosure provides a hard foam composition comprising: urethane and one or more hydroformylated polyols derived from microbial oil comprising 60% or more of one or more unsaturated fatty acids and/or up to nine TAG species, wherein the hard foam has a compressive strength of about 60 kPa to about 1500 kPa.

In some aspects, the present disclosure provides an elastomer composition comprising: urethane and one or more hydroformylated polyols derived from a microbial oil comprising 60% or more of one or more unsaturated fatty acids and/or up to nine TAG species, wherein the elastomer comprises a soft segment concentration of about 20% to about 70%.

In some aspects, the present disclosure provides a resin composition comprising: urethane and one or more hydroformylated polyols derived from a microbial oil comprising 60% or more of one or more unsaturated fatty acids and/or up to nine TAG species, wherein the resin has a tensile strength of 0.04 MPa or greater and an elongation at break of 20% or greater.

In some aspects, the present disclosure provides an adhesive composition comprising: urethane and one or more hydroformylated polyols derived from a microbial oil comprising 60% or more of one or more unsaturated fatty acids and/or up to nine TAG species.

In some embodiments, the one or more unsaturated fatty acids has 60% or more of an 18:1 fatty acid. In some embodiments, the one or more unsaturated fatty acids has 60% to 95% or more of an 18:1 fatty acid. In some embodiments, the up to nine TAG species is nine TAG species. In some embodiments, the up to nine TAG species is four TAG species. In some embodiments, a TAG species of the up to nine TAG species is triolein. In some embodiments, the microbial oil comprises 60% or more of one or more unsaturated fatty acids and up to nine TAG species.

DETAILED DESCRIPTION

This disclosure relates to methods for generating polyols by hydroformylation and hydrogenation of fatty acids present in microbial oils with high unsaturated fatty acid content and low triacylglycerol or "TAG" diversity (e.g., number of different TAG species in a microbial oil).

This disclosure also relates to applications for using hydroformylated polyols to make polyurethane materials, including, but not limited to, foams, elastomers, adhesives, resins, and cast urethanes.

As used herein, the term "hydroformylated" or "hydroformylation" refers to the sequential chemical reactions of hydroformylation (across C═C double bonds) to produce an aldehyde, followed by hydrogenation (of the resulting aldehyde) to produce an alcohol unless indicated otherwise.

As used herein, the term "triacylglycerol", "triglyceride", or "TAG" refers to esters between glycerol and three saturated and/or unsaturated fatty acids. Generally, fatty acids comprising TAGs have chain lengths of at least 8 carbon atoms up to 24 carbons or more.

As used herein, the term "microbial oil" refers to an oil extracted from a microbe, e.g., an oleaginous, single-celled, eukaryotic or prokaryotic microorganism, including, but not limited to, yeast, microalgae, and bacteria.

As used herein, the term "polyol", "biopolyol", "natural oil polyol", or "NOP" refers to triglycerols or fatty acid alcohols comprising hydroxyl functional groups.

As used herein, the term "polyurethane", "PU", or "urethane" refers to a class of polymers comprised of carbamate (urethane) linkages formed between a polyol and an isocyanate moiety.

As used herein, the term "TAG purity", "molecular purity", or "oil purity" refers to the number of molecular species that make up an oil composition, on an absolute basis or present in amounts above a certain threshold. The fewer the number of TAG species in an oil, the greater the "purity" of the oil. In some embodiments, a pure oil may be an oil comprising up to 9 TAG species and 60% of more of triolein. In some embodiments, a pure oil may comprise up to 4 TAG species present in amounts of above a certain threshold in the oil (e.g., ruling out trace amounts of other TAG) and 90% or more of a single TAG species, such as triolein.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are described herein.

Polyol Production

Microbial oil produced by oleaginous microbes has numerous advantages, including, but not limited to, improved production efficiency and a TAG composition that is enhanced for improved control of hydroformylation chemistry for generating polyols. These characteristics of microbial oil result in a greater degree of hydroxyl group (—OH) functionality relative to oils with greater TAG heterogeneity (hence, lower purity) and/or diversity (e.g., oilseed or plant derived oils). Thus, hydroformylated polyols derived from a microbial oil can be preferable in generating polymers, including in instances where physical properties of a polymer can be compromised by molecular impurities, such as non-hydroxylated fatty acids that may be present in oils having a more diverse or heterogeneous TAG profile.

Hydroformylated polyols derived from a microbial oil may be particularly useful for producing polyurethane materials. For example, microbial oils may comprise relatively low TAG diversity, low fatty acid diversity, and the majority of fatty acids present in the microbial oil may be unsaturated fatty acids. A higher ratio of unsaturated fatty acid to saturated fatty acid allows for increased chemical reactivity at the double bonds. Microbial oils having low TAG diversity and a high proportion of unsaturated fatty acids is especially desirable in production of polyurethanes because hydroformylation of such a mixture yields a greater percentage of hydroformylated fatty acids that can participate in crosslinking reactions with isocyanates. Unlike unsaturated fatty acids, saturated fatty acids do not contain C=C double bounds and cannot participate in crosslinking reactions with isocyanates. Thus, polyols generated from hydroformylation of unsaturated fatty acids from microbial oil may yield polyurethane materials having superior properties.

In the process of producing natural oil polyols (NOPs) from natural sources, the hydroxyl functionality can be introduced via a chemical conversion of the triglyceride oil. This conversion requires the presence of a double bond on the acyl moiety of the fatty acid, e.g. an olefinic group, which can be accomplished using several different chemistries including, for example:

i) Epoxidation in the presence of hydrogen peroxide and acid catalyst, followed by ring opening with reagents, such as water, hydrogen, methanol, ethanol, or other polyols. These chemistries result in secondary hydroxyl moieties, and are therefore less reactive, for example, with isocyanate or methyl esters.

ii) Ozonolysis by molecular oxygen results in the formation of ozonides, which upon further oxidation results in scission at the double bond and formation of di-acids, carboxylic acids, and, upon reduction with hydrogen, aldehydes. Ozonolysis and reduction of oleic acid, for example, produces azelaic acid, pelargonic acid, and pelargonaldehyde, respectively.

iii) Hydroformylation with synthesis gas (syngas), using rhodium or cobalt catalysts to form the aldehyde at the olefinic group, followed by reduction of the aldehyde to alcohol in the presence of hydrogen.

While typically carried out in organic solvent, processes that utilize aqueous systems have been developed to improve sustainability of these chemistries. Of the chemistries described above, only hydroformylation results in the preservation of fatty acid length and formation of primary —OH moieties. Primary —OH functionalities are highly desirable due to increased reactivity compared to secondary —OH moieties. Furthermore, only olefinic fatty acids with a double bond that is converted into a site possessing hydroxyl functionality, through epoxidation and ring opening, ozonolysis, or hydroformylation/reduction, can participate in subsequent downstream chemistries, i.e. reaction with an isocyanate moiety to form a urethane linkage or reaction with methyl esters to form polyesters. All other fatty acids, namely, fully saturated fatty acids that do not contain C=C double bonds, cannot participate in crosslinking reactions with isocyanates. Hence, saturated fatty acids will compromise the structural integrity and degrade performance of the polymer produced therefrom.

The complexity and physical properties of a triglyceride oil can be evaluated by the fatty acid profile, and the triacylglycerol (TAG) profile. The fatty acid profile is simply a measure of fatty acid composition. The fatty acid profile can be determined by subjecting oils to transesterification to generate fatty acid methyl esters and subsequently quantitating fatty acid type by Gas Chromatography equipped with a Flame Ionization Detector (GC-FID). Because fatty acids are arrayed at three positions along the glycerol backbone in the triglyceride molecule, the number of possible distinct regioisomers of TAG molecules is defined by the number of fatty acid species comprising the oil raised to the third power.

Soybean oil, for example, is comprised of 6 fatty acids. Thus, in theory, soybean oil can contain as many as 216 or ($6^3$) TAG regioisomers. The actual number of TAG regioisomers in soybean oil is substantially smaller (approximately 37), as soybean oil is a complex, heterogeneous material with each TAG species having varying levels of unsaturated fatty acids. Similarly, soybean oil derived polyols produced by hydroformylation/reduction are highly heterogeneous, which negatively impacts the physical properties of the final polymer produced therefrom. Thus, oils that are very low in saturates and high in a particular species of unsaturated fatty acid are most suitable for generating NOPs since virtually all fatty acids contained in the triglyceride oil can participate in crosslinking with isocyanate moieties.

Additionally, if the fatty acid profile can be modulated such that the concentration of a particular species of monounsaturated or polyunsaturated fatty acid can be significantly increased from the concentration in the native oil, there would be an overall decrease in the diversity of TAG species present in the resulting oil. The net effect is that a higher number of hydroxylated fatty acids and a higher proportion of all TAG species can participate in urethane chemistries. For example, in two cultivars of peanut oil, N-3101 and H4110, oleic acid content was increased from 46% to 80% and total monounsaturated and polyunsaturated fatty acids was increased only subtly, from 77% to 84%, respectively. According to the TAG profile of the resulting oils derived from the two cultivars, approximately 95% of all TAG species are accounted for in just eight regioisomers in cultivar H4110 and 23 regioisomers in cultivar N-3101. Thus, triglycerides that are significantly enriched in a single species result in more homogeneous substrates for subsequent chemical manipulations and incorporation into materials.

Provided herein are methods for the conversion of oils into highly homogenous polyols via hydroformylation and hydrogenation. Hydroformylated polyols may be reacted with isocyanates to produce polymers with high homogeneity. FIG. 1 provides a schematic overview of this process in which high purity oils (e.g., microbial oil(s) comprising 60% or more of one or more unsaturated fatty acids, oil(s) comprising up to nine TAG species present in an amount of 1% or more in the oil, and the like) are hydroformylated and hydrogenated to yield hydroformylated polyols. Hydroformylated polyols can be used as starting material for polyurethane formulations (e.g., by reacting with isocyanate and a chain extender). In some embodiments, high purity oils can undergo processing steps prior to or following hydroformylation and hydrogenation depending on the desired properties of the polymer product. For example, microbial oils can be methylated prior to or following hydroformylation and hydrogenation to produce methylated microbial oils for producing polyester products.

Physical properties of polyurethanes prepared using NOPs can be compromised by molecular impurities. This is particularly true for elastomeric applications in which natural oil polyols (NOPs) are used as components in polyesterdiols. Unlike the polyols disclosed in the present disclosure, as a result of impurities, non-functionalized fatty acid methyl esters derived from oils of lower purity cannot participate in the formation of the polymer network. Additionally, the high reactivity of polyols disclosed herein (e.g., exemplified by the hydroxyl number and primary —OH functionality of the polyol) can be particularly useful in cast urethane and 3-D printing applications, as well as components in thermoplastic polyurethanes (TPUs). The molecular purity of these polyols can be advantageous for all types of polyurethane applications, for example, as coatings for textiles and surfaces, as adhesives in packaging, textile, and industrial applications, as well as in hard and soft foam and elastomeric applications.

Microbial Oils
Microbes

Microbial oils used in the instant disclosure may comprise novel triglycerides derived from a microbe. Microbial oils may be produced using oleaginous microbes.

Oleaginous microbes can refer to species of microbes having oil contents in excess of 20% on a dry cell weight basis. These microbes are uniquely suited for generating highly pure, NOPs with primary hydroxyl (—OH) functionality. Oleaginous microbes have also been proven extremely facile for genetic modification and improvement through synthetic biology approaches.

Indeed, these improvements can occur on time scales that are greatly accelerated relative to what can be achieved in higher plant oilseeds. Oleaginous microbes offer tremendous utility in generating large quantities of triglyceride oils in short periods of time. In as little as 48 hours, appreciable oil production of about 30-40% oil (dry cell weight) can be obtained, whereas typical production requires 120 hours or more to achieve 70-80% oil (dry cell weight).

Furthermore, because these microbes can be heterotrophically grown using simple sugars, the production of these triglyceride oils can be divorced from the traditional constraints imposed by geography, climate, and season on triglyceride oil production from oilseed crops.

Recombinant DNA techniques can be used to engineer or modify oleaginous microbes to produce triglyceride oils having desired fatty acid profiles and regio- or stereospecific profiles. Fatty acid biosynthetic genes, including, for example, those encoding stearoyl-ACP desaturase, delta-12 fatty acid desaturase, acyl-ACP thioesterase, ketoacyl-ACP synthase, and lysophosphatidic acid acyltransferase can be manipulated to increase or decrease expression levels and biosynthetic activity. These genetically engineered microbes can produce oils having enhanced oxidative and thermal stability, or for use as sustainable feedstock sources for various chemical processes. The fatty acid profile of the oils can be enriched in midchain profiles or the oil can be enriched in triglycerides having specific saturation contents. WO2010/063031, WO2010/120923, WO2012/061647, WO2012/106560, WO2013/082186, WO2013/158938, WO2014/176515, WO2015/051319, Lin et al. (2013) *Bioengineered*, 4:292-304, and Shi and Zhao. (2017) *Front. Microbiol.*, 8: 2185 each discloses microbial genetic engineering techniques for oil production and is entirely incorporated herein by reference.

Among microalgae, several genera and species are particularly suitable for producing triglyceride oils that can be converted to polyols including, but not limited to, *Chlorella* sp., *Pseudochlorella* sp., *Heterochlorella* sp., *Prototheca* sp., *Arthrospira* sp., *Euglena* sp., *Nannochloropsis* sp., *Phaeodactylum* sp., *Chlamydomonas* sp., *Scenedesmus* sp., *Ostreococcus* sp., *Selenastrum* sp., *Haematococcus* sp., *Nitzschia, Dunaliella, Navicula* sp., *Trebouxia* sp., *Pseudotrebouxia* sp., *Vavicula* sp., *Bracteococcus* sp., *Gomphonema* sp., *Watanabea* sp., *Botryococcus* sp., *Tetraselmis* sp., and *Isochrysis* sp.

Among oleaginous yeasts, several genera are particularly suitable for producing triglyceride oils that can be converted to polyols including, but not limited to, *Candida* sp., *Cryptococcus* sp., *Debaromyces* sp., *Endomycopsis* sp., *Geotrichum* sp., *Hyphopichia* sp., *Lipomyces* sp., *Pichia* sp., *Rodosporidium* sp., *Rhodotorula* sp., *Sporobolomyces* sp., *Starmerella* sp., *Torulaspora* sp., *Trichosporon* sp., *Wickerhamomyces* sp., *Yarrowia* sp., and *Zygoascus* sp.

Among oleaginous bacteria there are several genera and species which are particularly suited to producing triglyceride oils that can be converted to polyols including, but not limited to *Flavimonas oryzihabitans, Pseudomonas aeruginosa, Morococcus* sp., *Rhodobacter sphaeroides, Rhodococcus opacus, Rhodococcus erythropolis, Streptomyces jeddahensis, Ochrobactrum* sp., *Arthrobacter* sp., *Nocardia* sp., *Mycobacteria* sp., *Gordonia* sp., *Catenisphaera* sp., and *Dietzia* sp.

Growth of Oleaginous Microbes and Extraction of Microbial Oil

Oleaginous microbes may be cultivated in a bioreactor or fermenter. For example, heterotrophic oleaginous microbes can be cultivated on a sugar-containing nutrient broth.

Oleaginous microbes produce microbial oil, which comprises triacylglycerides or triacylglycerols and may be stored in storage bodies of the cell. A raw oil may be obtained from microbes by disrupting the cells and isolating the oil. WO2008/151149, WO2010/06032, WO2011/150410, WO2012/061647, and WO2012/106560 each disclose heterotrophic cultivation and oil isolation techniques and is entirely incorporated by reference herein. For example, microbial oil may be obtained by providing or cultivating, drying and pressing the cells. Microbial oils produced may be refined, bleached, and deodorized (RBD) as described in WO2010/120939, which is entirely incorporated herein by reference. Microbial oils can be obtained without further enrichment of one or more fatty acids or triglycerides with respect to other fatty acids or triglycerides in the raw oil composition.

Microbial Oil Content

A microbial oil may be characterized by its triacylglycerol ("TAG") profile. A TAG profile indicates relative amounts of various TAGs, and consequently, fatty acids (each TAG molecule is a tri-ester of glycerol and three fatty acids) that are present in microbial oil. As disclosed herein, fatty acids from microbial oils having TAG profiles comprising high levels of unsaturated fatty acids and/or having low TAG diversity may be hydroformylated and hydrogenated to produce hydroformylated polyols.

A microbial oil may have a TAG profile comprising a high proportion of one or more unsaturated fatty acids relative to other fatty acids in the microbial oil. A microbial oil may have a TAG profile comprising 60% or more of one or more unsaturated fatty acids.

A microbial oil may have a TAG profile comprising a high proportion of one or more unsaturated fatty acids relative to one or more saturated fatty acids in the microbial oil. A microbial oil may have a TAG profile comprising low TAG diversity, e.g., fewer TAG species than in, for example, an oilseed derived oil. Microbial oils rich in a TAG or fatty acid may comprise fewer varieties of TAG species or lesser amounts of different TAG species.

Oils derived from microorganisms having TAG profiles with high purity/high homogeneity/low diversity and high unsaturated fatty acid content are particularly advantageous for use in polyurethane production. Highly pure oils improve product yield and reduce the likelihood of contaminants that adversely affect the physical properties of the resulting polyurethane. Highly unsaturated oils allow for increased numbers of primary alcohol groups formed during hydroformylation and hydrogenation, thereby increasing the functionality, reactivity, and crosslinking during subsequent polymerization reactions. The quantity and type of crosslinking influence the stability, durability, and rigidity of the resulting polymer.

In some embodiments, an oil composition described herein comprises up to nine, up to eight, up to seven, up to six, up to five, up to four, up to three, up to two, or one TAG species present in amounts of 1% or more of the total TAG species.

In some embodiments, the microbial oil comprises one TAG species present in amounts of about 85% or more, about 86% or more, about 87% or more, about 88% or more, about 89% or more, about 90% or more, about 91% or more, about 92% or more, about 93% or more, about 94% or more, about 95% or more, about 96% or more, about 97% or more, about 98% or more, or about 99% or more of the total TAG species.

In some embodiments, an oil composition described herein comprises two TAG species present in amounts of about 85% or more, about 86% or more, about 87% or more, about 88% or more, about 89% or more, about 90% or more, about 91% or more, about 92% or more, about 93% or more, about 94% or more, about 95% or more, about 96% or more, about 97% or more, about 98% or more, or about 99% or more of the total TAG species.

In some embodiments, an oil composition described herein comprises three TAG species present in amounts of about 85% or more, about 86% or more, about 87% or more, about 88% or more, about 89% or more, about 90% or more, about 91% or more, about 92% or more, about 93% or more, about 94% or more, about 95% or more, about 96% or more, about 97% or more, about 98% or more, or about 99% or more of the total TAG species.

Non-limiting examples of TAG species include OOO, LLL, LnLnLn, LLP, LPL, LnLnP, LnPLn, and any regioisomer thereof, wherein O is olein, L is linolein, Ln is linolenin, and P is palmitin. In some embodiments, the predominant TAG species in the microbial oil is OOO, LLL, LnLnLn, LLP, LPL, LnLnP, LnPLn, or any regioisomer thereof.

In some embodiments, the predominant TAG species in an oil described herein is OOO or triolein. In some embodiments, the microbial oil comprises at least about 60%, at least about 61%, at least about 62%, at least about 63%, at least about 64%, at least about 65%, at least about 66%, at least about 67%, at least about 68%, at least about 69%, at least about 70%, least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% of triolein.

In some embodiments, the fatty acid profile of an oil described herein comprises at least about 60%, at least about 61%, at least about 62%, at least about 63%, at least about 64%, at least about 65%, at least about 66%, at least about 67%, at least about 68%, at least about 69%, at least about 70%, least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% of any one or combination of unsaturated fatty acid species. Non-limiting examples of unsaturated fatty acid species include of a 16:1 fatty acid, a 16:2 fatty acid, a 16:3 fatty acid, an 18:1 fatty acid, an 18:2 fatty acid, an 18:3 fatty acid, an 18:4 fatty acid, a 20:1 fatty acid, a 20:2 fatty acid, a 20:3 fatty acid, a 22:1 fatty acid, a 22:2 fatty acid, a 22:3 fatty acid, a 24:1 fatty acid, a 24:2 fatty acid, and a 24:3 fatty acid.

In some embodiments, the fatty acid profile of an oil described herein comprises up to about 1%, up to about 2%, up to about 3%, up to about 4%, up to about 5%, up to about 6%, up to about 7%, up to about 8%, up to about 9%, up to about 10%, up to about 11%, least about 12%, up to about 13%, up to about 14%, up to about 15%, up to about 16%, up to about 17%, up to about 18%, up to about 19%, up to about 20%, up to about 21%, up to about 22%, up to about 23%, up to about 24%, up to about 25%, up to about 26%, up to about 27%, up to about 28%, up to about 29%, up to about 30%, up to about 31%, up to about 32%, up to about 33%, up to about 34%, or up to about 35% of any one or combination of saturated fatty acid species. Non-limiting examples of saturated fatty acid species include a 16:0 fatty acid, an 18:0 fatty acid, a 20:0 fatty acid, a 22:0 fatty acid, a 22:0 fatty acid, or a 24:0 fatty acid.

In some embodiments, the fatty acid profile of an oil described herein comprises about 60%, about 61%, about 62%, about 63%, about 64%, about 65%, about 66%, about 67%, about 68%, about 69%, about 70%, least about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% of any one or combination of unsaturated fatty acid species. Non-limiting examples of unsaturated fatty acid species include a 16:1 fatty acid, a 16:2 fatty acid, a 16:3 fatty acid, an 18:1 fatty acid, an 18:2 fatty acid, an 18:3 fatty acid, an 18:4 fatty acid, a 20:1 fatty acid, a 20:2 fatty acid, a 20:3 fatty acid, a 22:1 fatty acid, a 22:2 fatty acid, a 22:3 fatty acid, a 24:1 fatty acid, a 24:2 fatty acid, and a 24:3 fatty acid.

In some embodiments, the fatty acid profile of an oil described herein comprises at least about 60%, at least about 61%, at least about 62%, at least about 63%, at least about 64%, at least about 65%, at least about 66%, at least about 67%, at least about 68%, at least about 69%, at least about 70%, least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% of any one or combination of unsaturated fatty acid species. Non-limiting examples of unsaturated fatty acid species include those listed in TABLE 1.

In some embodiments, the fatty acid profile of an oil described herein comprises about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% of any one or combination of unsaturated fatty acid species. Non-limiting examples of unsaturated fatty acid species include those listed in TABLE 1.

TABLE 1

| Mono-unsaturated FA | Lipid Number | Poly-unsaturated FA | Lipid Number |
|---|---|---|---|
| Myristoleic acid | C14:1 | Hexadecatrienoic acid (HTA) | C16:3 |
| Palmitoleic acid | C16:1 | Linoleic acid | C18:2 |
| Sapienic acid | C16:1 | Linolelaidic acid | C18:2 |
| Oleic acid | C18:1 | α-Linolenic acid | C18:3 |
| Elaidic acid | C18:1 | Pinolenic acid | C18:3 |
| Vaccenic acid | C18:1 | Stearidonic acid | C18:4 |
| Petroselinic acid | C18:1 | Eicosadienoic acid | C20:2 |

TABLE 1-continued

| Mono-unsaturated FA | Lipid Number | Poly-unsaturated FA | Lipid Number |
|---|---|---|---|
| Eicosenoic (Gondoic) acid | C20:1 | Mead acid | C20:3 |
|  |  | Eicosatrienoic acid (ETE) | C20:3 |
| Paullinic acid | C20:1 | Dihomo-γ-linolenic acid (DGLA) | C20:3 |
| Gadoleic acid | C20:1 |  |  |
| Erucic acid | C22:1 | Podocarpic acid | C20:3 |
| Brassidic acid | C22:1 | Arachidonic acid (AA) | C20:4 |
| Nervonic acid | C24:1 | Eicosatetraenoic acid (ETA) | C20:4 |
|  |  | Eicosapentaenoic acid (EPA) | C20:5 |
|  |  | Heneicosapentaenoic acid (HPA) | C21:5 |
|  |  | Docosadienoic acid | C22:2 |
|  |  | Adrenic acid (AdA) | C22:4 |
|  |  | Docosapentaenoic acid (Osbond acid) | C22:5 |
|  |  | Docosahexaenoic acid (DPA) | C22:5 |
|  |  | Docosahexaenoic acid (DHA) | C22:6 |
|  |  | Tetracosatetraenoic acid | C24:4 |
|  |  | Tetracosapentaenoic acid | C24:5 |

In some embodiments, the fatty acid profile of an oil described herein comprises at least about 60%, at least about 61%, at least about 62%, at least about 63%, at least about 64%, at least about 65%, at least about 66%, at least about 67%, at least about 68%, at least about 69%, at least about 70%, least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% of an 18:1 fatty acid.

In some embodiments, the fatty acid profile of an oil described herein comprises about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% of an 18:1 fatty acid.

In some embodiments, the fatty acid profile of an oil described herein comprises at least about 60%, at least about 61%, at least about 62%, at least about 63%, at least about 64%, at least about 65%, at least about 66%, at least about 67%, at least about 68%, at least about 69%, at least about 70%, least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% of oleic acid or oleate.

In some embodiments, the fatty acid profile of an oil described herein comprises about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% of oleic acid or oleate.

In some embodiments, the fatty acid profile of an oil described herein comprises up to about 1%, up to about 2%, up to about 3%, up to about 4%, up to about 5%, up to about 6%, up to about 7%, up to about 8%, up to about 9%, up to about 10%, up to about 11%, least about 12%, up to about 13%, up to about 14%, up to about 15%, up to about 16%, up to about 17%, up to about 18%, up to about 19%, up to about 20%, up to about 21%, up to about 22%, up to about 23%, up to about 24%, up to about 25%, up to about 26%, up to about 27%, up to about 28%, up to about 29%, up to about 30%, up to about 31%, up to about 32%, up to about 33%, up to about 34%, or up to about 35% of any one or combination of saturated fatty acid species selected from the group consisting of a 16:0 fatty acid, an 18:0 fatty acid, a 20:0 fatty acid, a 22:0 fatty acid, and a 24:0 fatty acid.

In some embodiments, an oil described herein comprises 60% or more of an 18:1 fatty acid and 30% or less of one or more saturated fatty acids. In some embodiments, an oil described herein comprises at least 85% oleate and up to 5% linoleate.

In some embodiments, an oil described herein comprises 60% or more of an 18:1 fatty acid, 30% or less of one or more saturated fatty acids, and at least one unsaturated fatty acid in a remainder. In some embodiments, an oil described herein comprises at least 85% oleate, up to 5% linoleate, and up to 1.8% palmitate.

In some embodiments, an oil described herein comprises at least 60% of an 18:1 fatty acid and up to 15% of one or more other unsaturated fatty acids selected from the group consisting of: a 16:1 fatty acid, an 18:2 fatty acid, an 18:3 fatty acid, and any combination thereof.

In some embodiments, an oil described herein comprises at least 60% of an 18:1 fatty acid, up to 10% of an 18:2 fatty acid, and up to 20% of a 16:0 fatty acid.

In some embodiments, an oil described herein comprises at least 70% of an 18:1 fatty acid, up to 8% of an 18:2 fatty acid, and up to 12% of a 16:0 fatty acid.

In some embodiments, an oil described herein comprises at least 80% of an 18:1 fatty acid, up to 8% of an 18:2 fatty acid, and up to 5% of a 16:0 fatty acid.

Hydroformylation

Hydroformylation is a chemical process for converting alkenes to aldehydes, which results in the addition of a formyl (CHO) group and a hydrogen atom on the carbon-carbon double bond. The process of hydroformylation requires high pressures of carbon monoxide and hydrogen (syngas) at temperatures between about 40° C. and 200° C. Hydroformylation reactions also typically require transition metal catalysts.

In some embodiments, hydroformylation can be performed at about 40° C., about 50° C., about 60° C., about 70° C., about 80° C., about 90° C., about 100° C., about 110° C., about 120° C., about 130° C., about 140° C., about 150° C., about 160° C., about 170° C., about 180° C., about 190° C., about 200° C., about 210° C., about 220° C., about 230° C., about 240° C., or about 250° C.

In some embodiments, hydroformylation can be performed at about 500 psi, about 600 psi, about 700 psi, about 800 psi, about 900 psi, about 1000 psi, about 1100 psi, about 1200 psi, about 1300 psi, about 1400 psi, or about 1500 psi.

In some embodiments, hydroformylation can be performed for about 1 hour, about 1.5 hours, about 2 hours, about 2.5 hours, about 3 hours, about 3.5 hours, about 4 hours, about 4.5 hours, about 5 hours, about 5.5 hours, or about 6 hours.

Hydroformylation reactions can be performed using various catalysts, including for example, cobalt-based catalysts, cobalt tetracarbonyl hydride, cobalt phosphine catalysts, cobalt supplemented with various noble metals (e.g., palladium, ruthenium, and platinum), rhodium-based catalysts, rhodium phosphine catalysts, acetylacetonato-dicarbonylrhodium(I) ($Rh(CO)_2acac$), rhodium/cyclohexyl diphenylphosphine (Rh/CHDPP), or any transition metal-based catalyst suitable for hydroformylation.

Hydrogenation

Hydrogenation is the reduction of olefinic or aldehyde groups to alkanes or alcohols, respectively, using $H_2$. Unsaturated fatty acids can be hydrogenated to produce saturated fatty acids. Hydroformylation followed by hydrogenation of unsaturated fatty acids can be used to create polyols. Hydrogenation reactions are performed using various types of metal catalysts including nickel, palladium, and platinum.

In some embodiments, hydrogenation can be performed at about 40° C., about 50° C., about 60° C., about 70° C., about 80° C., about 90° C., about 100° C., about 110° C., about 120° C., about 130° C., about 140° C., about 150° C., about 160° C., about 170° C., about 180° C., about 190° C., about 200° C., about 210° C., about 220° C., about 230° C., about 240° C., or about 250° C.

In some embodiments, hydrogenation can be performed at about 500 psi, about 600 psi, about 700 psi, about 800 psi, about 900 psi, about 1000 psi, about 1100 psi, about 1200 psi, about 1300 psi, about 1400 psi, or about 1500 psi.

In some embodiments, hydrogenation can be performed for about 1 hour, about 1.5 hours, about 2 hours, about 2.5 hours, about 3 hours, about 3.5 hours, about 4 hours, about 4.5 hours, about 5 hours, about 5.5 hours, or about 6 hours.

Hydrogenation can be performed using various catalysts, including for example, Raney nickel (spongy nickel), Urushibara nickel, nickel, palladium, platinum, rhodium, and ruthenium.

Fatty Acid Methyl Esters

Like triglycerides, fatty acid methyl esters (FAME) of triglycerides can undergo hydroformylation and hydrogenation to produce other polyol derivatives. Transesterification of triglycerides to fatty acid methyl esters can be performed by reacting with methanol and potassium methoxide. The resultant FAME can then undergo hydroformylation and hydrogenation to produce hydroformylated, hydrogenated fatty acid methyl polyesters. Polyesters are useful for the production of elastomers.

Polyols

Hydroformylation and hydrogenation of TAG and fatty acids produces polyols, a principle component in polyurethane production. Polyol derivatives may be produced by hydroformylation and hydrogenation, hydroformylation and hydrogenation followed by methylation, or methylation followed by hydroformylation and hydrogenation. Methylation of TAG or fatty acids yields fatty acid methyl esters. Methylation of hydroformylated polyols yields hydroformylated polyol methyl esters.

In some embodiments, oils may undergo hydrogenation prior to hydroformylation and hydrogenation to alter fatty acid saturation levels, resulting in partially saturated TAG and/or fatty acids. In some embodiments, oils may undergo hydrogenation prior to methylation to alter fatty acid saturation levels.

Polyols derived from highly unsaturated oils have high hydroxyl numbers compared to polyols derived from oils having lower saturation levels. High hydroxyl number increases the versatility of a polyol for producing a wide range of polyurethane materials. A polyol produced from methods described herein can have a hydroxyl number of from 90 to 190, from 140 to 190, from 100 to 180, from 150 to 165, from 150 to 160, from 170 to 175, from 175 to 182, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, or 190.

Polyurethane Production

Polyurethanes are linear polymers that have a molecular backbone containing carbamate/urethane groups (—NHCO$_2$). Polyurethanes are produced by reacting polyols with isocyanates in the presence of catalyst, heat, a linker or chain extender, and other additives. Additives can include surfactants (e.g. silicon surfactants), emulsifiers, stabilizers, property modifiers, performance additives, curatives, release agents, and coloring agents (e.g. color pastes). Additives can be used to achieve specific physical and functional properties of the polyurethane, as well as improve processing, resin stability, cycle times, and overall yields. U.S. Pat. No. 4,374,209 discloses methods of polyurethane synthesis, and is entirely incorporated by reference herein.

Wide variation in physical properties of polyurethane polymers can be attained by varying the type of starting materials, for example, the starting polyol, isocyanate, and chain extender. Chain extenders are typically low molecular weight compounds, such as hydroxyl amines, glycols, or diamines, that facilitate polymerization. Chain extenders greatly influence the mechanical response (rigidity and flexibility) of the PU. For example, polyurethane elastomers, where at least one ingredient has a glass transition temperature below room temperature, consist of alternating flexible (soft) and relatively rigid and/or mobile (hard) segments. Phase segregation occurs during and following polymerization, to produce an elastomeric matrix of the soft segments containing rigid inclusions formed by association of the hard segments. Non-limiting examples of chain extenders include ethylene glycol, diethylene glycol, triethylene glycol, tetraethylene glycol, propylene glycol (1,3-propanediol), dipropylene glycol, tripropylene glycol, neopentyl glycol, alkyl diols of varying lengths (HO—(CH$_2$)$_p$—OH, where p is an integer greater than 1), 1,3-butanediol, 1,4-butanediol, 1,6-pentanediol, 1,6-hexanediol, 1,2,6-hexanetriol, 1,4-cyclohexanedimethanol, ethanolamine, diethanolamine, methyldiethanolamine, phenyldiethanolamine, triethanolamine, isosorbide, glycerol, trimethylolpropane, pentaerythritol, diethyltoluenediamine, dimethylthiotoluenediamine, N,N, N',N'-tetrakis, glycerol, monoacylglycerol, diacylglycerol, and hydroquinone bis(2-hydroxyethyl) (HQEE).

Methylene diphenyl diisocyanate (MDI), and toluene diisocyanate (TDI), hexamethylene diisocyanate (HDI), isophorone diisocyanate (IPDI), and methyl isocyanate (MIC) are common isocyanates used in the production of polyurethanes. Additional non-limiting examples of isocyanates include Rubinate® 9225, Rubinate® 44, and Rubinate® M. Rubinate® 9225 is a uretonomine-modified pure MDI. Rubinate® 9225 is derived from pure MDI and has been adjusted with a moderate amount of 2,4' isomer to improve stability and maximize physical properties. Rubinate® 9225 can be used as a precursor for prepolymers. Rubinate® 44 is a pure (>98%) 4,4' MDI with a melting point of 38° C. and is solid at room temperature. Rubinate® M isocyanate is a standard polymeric MDI.

Catalysts used for polymerization of polyols and isocyanates to form polyurethanes include, for example, tin catalysts, dibutyl tin dilaurate (DBTDL), dibutyltin diacetate (DBTDA), triethylenediamine (TEDA or DABCO), dimethylcyclohexylamine (DMCHA), dimethylethanolamine (DMEA), and bis-(2-dimethylaminoethyl)ether (A-99), titanium(IV) isopropoxide, tin carboxylates, bismuth-based catalysts, bismuth carboxylates, zinc carboxylates, zirconium carboxylates, nickel carboxylates, metal carboxylates, amines, and amine catalysts (e.g., JEFFCAT® catalysts (e.g. JEFFCAT® ZF-22)). Catalyst selection can depend on balancing three reactions: urethane (polyol+isocyanate, or gel) formation, urea (water+isocyanate, or "blow") formation, and the isocyanate trimerization reaction. In some embodiments, catalysts are not required for polymerization. For example, heat can be used to accelerate the polymerization reaction.

Polyurethane Products

Polyurethanes produced from hydroformylated polyols described herein, including those generated from microbial oils, may have improved stability, durability, hydrophobicity, and rigidity over polyurethane materials produced from conventional oils, such as those derived from plant oilseed crops.

Polyurethanes can be used for the manufacture of various products, including, for example, rigid foams, hard foams, spray foams, flexible foams, adhesives, sealants, fibers, elastomers, cast urethanes, coatings, surface finishes, inks, paints, synthetic leather, lubricants and functional fluids, and personal care products.

Rigid foams and hard foams can be used in products, including, for example, surfboards, paddleboards, insulated coolers, housing insulation, automotive parts, aerospace foam, watercraft foam, marine insulation, structural foams, windmill blades, signage, movie set display foam, foam rollers, lightweight aircrafts, lightweight watercrafts, other recreational equipment or other outdoor equipment.

Spray foams can be used in products, including, for example, insulated coolers, home and industrial building insulation, marine insulation, pipe insulation, airplane hangar insulation, mining, and packaging for shipping purposes.

Foams produced by the methods described herein may have a density of from about 15 kg/m$^3$ to about 50 kg/m$^3$, about 20 kg/m$^3$ to about 200 kg/m$^3$, about 15 kg/m$^3$, about 16 kg/m$^3$, about 17 kg/m$^3$, about 18 kg/m$^3$, about 19 kg/m$^3$, about 20 kg/m$^3$, about 25 kg/m$^3$, about 30 kg/m$^3$, about 35 kg/m$^3$, about 40 kg/m$^3$, about 45 kg/m$^3$, about 50 kg/m$^3$, about 55 kg/m$^3$, about 60 kg/m$^3$, about 65 kg/m$^3$, about 70 kg/m$^3$, about 75 kg/m$^3$, about 80 kg/m$^3$, about 85 kg/m$^3$, about 90 kg/m$^3$, about 95 kg/m$^3$, about 100 kg/m$^3$, about 105 kg/m$^3$, about 110 kg/m$^3$, about 115 kg/m$^3$, about 120 kg/m$^3$, about 125 kg/m$^3$, about 130 kg/m$^3$, about 135 kg/m$^3$, about 140 kg/m$^3$, about 145 kg/m$^3$, about 150 kg/m$^3$, about 155 kg/m$^3$, about 160 kg/m$^3$, about 165 kg/m$^3$, about 170 kg/m$^3$, about 175 kg/m$^3$, about 180 kg/m$^3$, about 185 kg/m$^3$, about 190 kg/m$^3$, about 195 kg/m$^3$, or about 200 kg/m$^3$.

Foams produced by the methods described herein may have a compressive strength of from about 50 kPa to 1500 kPa, about 200 kPa to about 1100 kPa, about 50 kPa, about 60 kPa, about 75 kPa, about 90, kPa, about 100 kPa, about 150 kPa, about 200 kPa, about 300 kPa, about 400 kPa, about 500 kPa, about 600 kPa, about 700 kPa, about 800 kPa, about 900 kPa, about 1000 kPa, about 1100 kPa, about 1200 kPa, about 1300 kPa, about 1400 kPa, about 1500 kPa, or greater.

Flexible foams can be used in products, including, for example, mattresses, bedding, pet bedding, pillows, seat cushions, automotive cushioning and flooring, carpet underlay, life jackets, personal flotation devices, sleeping pads, gym mats, yoga mats, backpacks, bouldering crash pads, body padding, acoustic uses, filters, wetsuits, packaging, protective case inserts, foam rollers, shoe soles, cleaning sponges, medical sponges, luggage and pack padding, shoulder straps, and waist straps.

Compression set resistance is the ability of a foam to return to its original thickness after a compression load, under a specific time and temperature, is released. The compression set of a material is the permanent deformation remaining when an applied force is removed. Flexible foams produced by the methods described herein may have compression set resistance of about 5% to about 30%, about 6% to about 22%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25% about 26%, about 27%, about 28%, about 29%, or about 30%.

Adhesives can be used in products, including, for example, for bonding materials such as textiles, nonwovens, metal, synthetic fibers, natural fibers, plastics, wood, concrete, ceramic, plastics, glass fiber reinforced plastic, rubber, carpet, paper, cardboard, vinyl, carpet backing, climbing skins, jackets, tents, packs, gloves, shoes, goggles, and other outdoor equipment and apparel.

Sealants can be used in products, including, for example, for asphalt, cement, concrete, ceramic, tires, wood, metal, glass, vacuum systems, boat hulls, or bone.

Elastomers can be used in products, including, for example, hydration bladders, flexible liquid storage containers, water bottles, backpacks, duffel bags, luggage, gear boxes, marine fabrics, swimming goggles, gaskets, wire and cable coatings, tubing, handle grips, and footwear (e.g. hiking boots, approach shoes, trail running shoes, rock climbing shoes, and athletic shoes).

Soft segment concentration (SSC) is a measure of the ratio of hard and soft segments of an elastomer. Elastomers produced by the methods described herein may have a SSC of from about 20% to about 90%, from about 20% to about 80%, from about 20% to about 70%, about 10%, about 15%, about 20%, about 25%, about 30%, about 35%, about 40%, about 45%, about 50%, about 55%, about 60%, about 65%, about 70%, about 75%, about 80%, about 85%, or about 90%.

Cast urethanes can be used in products, including, for example, wheels (e.g. for skateboards, rollerblades, and roller skates), wheels and castors (e.g. for carts and furniture), conveyance rollers, frames for sports goggles (e.g. for dirt biking, motor cycling, and winter sports), and resins (e.g. for prototyping).

Resins produced by the methods described herein may have a tensile strength of about 0.04 MPa to about 70 MPa, about 0.04 MPa to about 80 MPa, about 0.04 MPa, about 0.05 MPa, about 0.10 MPa, about 0.15 MPa, about 0.20 MPa, about 0.25 MPa, about 0.30 MPa, about 0.35 MPa, about 0.40 MPa, about 0.45 MPa, about 0.50 MPa, about 0.55 MPa, about 0.60 MPa, about 0.65 MPa, about 0.70 MPa, about 0.75 MPa, about 0.80 MPa, about 0.85 MPa, about 0.90 MPa, about 0.95 MPa, about 1 MPa, about 2 MPa, about 3 MPa, about 4 MPa, about 5 MPa, about 6 MPa, about 7 MPa, about 8 MPa, about 9 MPa, about 10 MPa, about 11 MPa, about 12 MPa, about 13 MPa, about 14 MPa, about 15 MPa, about 16 MPa, about 17 MPa, about 18 MPa, about 19 MPa, about 20 MPa, about 21 MPa, about 22 MPa, about 23 MPa, about 24 MPa, about 25 MPa, about 26 MPa, about 27 MPa, about 28 MPa, about 29 MPa, about 30 MPa, about 31 MPa, about 32 MPa, about 33 MPa, about 34 MPa, about 35 MPa, about 36 MPa, about 37 MPa, about 38 MPa, about 39 MPa, about 10 MPa, about 41 MPa, about 42 MPa, about 43 MPa, about 44 MPa, about 45 MPa, about 46 MPa, about 47 MPa, about 48 MPa, about 49 MPa, about 50 MPa, about 51 MPa, about 52 MPa, about 53 MPa, about 54 MPa, about 55 MPa, about 56 MPa, about 57 MPa, about 58 MPa, about 59 MPa, about 60 MPa, about 61 MPa, about 62 MPa, about 63 MPa, about 64 MPa, about 65 MPa, about 66 MPa, about 67 MPa, about 68 MPa, about 69 MPa, about 70 MPa, about 71 MPa, about 72 MPa, about 73 MPa, about 74 MPa, about 75 MPa, about 76 MPa, about 77 MPa, about 78 MPa, about 79 MPa, about 80 MPa, or greater.

Resins produced by the methods described herein may have an elongation at break of about 1% to about 300%, about 2% to about 300%, about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 205%, about 210%, about 215%, about 220%, about 225%, about 230%, about 235%, about 240%, about 245%, about 250%, about 255%, about 260%, about 265%, about 270%, about 275%, about 280%, about 285%, about 290%, about 295%, about 300%, or greater.

Coatings, surface finishes, inks, and paints can be used in products, including, for example, for surface finishes, inks, and paints for surfaces, such as fabric, textiles, nonwovens, leather, synthetic leather, wood, nylon, metal, natural fibers, synthetic fibers, ceramic, plastic, recycled plastic, concrete, fire retardant clothing, paper, newspaper, masonry, and electronics. Inks can include, for example, printing inks, toner, ink jet printing, preservation ink, and fabric ink. Finishes can include, for example, finishes used on skateboards, surfboards, paddle boards, kiteboards, snowshoes, sails, and apparel, such as jackets, rain jackets, ski jackets, rain paints, waders, socks, underwear, tents, canopies, packs, and luggage.

Synthetic leather products, including, for example, for footwear (e.g. climbing shoes, hiking boots, approach shoes, snow shoes, biking shoes, cleats, running shoes, dress shoes), apparel or clothing (e.g. jackets and pants), automotive and aerospace interiors, watercraft seating and interiors, home furnishings, office furniture, bags, purses, wallets, phone covers, electronics casings, watch bands, belts, bicycle seats, backpacks, gloves, and sporting goods equipment (e.g. baseball gloves, footballs, soccer balls, gymnastics equipment, and motorcycle suits).

Lubricants and functional fluids can be used in products, including, for example, for metal working, machining fluids, cutting fluids, metal stamping, metal forming, wire drawing, oven chain lubrication, greases, and hydraulic fluids.

Personal care products can include, for example, lip balm, lip gloss, lotions, sunscreen, emollients, shampoo, and conditioner.

EXAMPLES

Example 1. Synthesis of a Hydroformylated, Hydrogenated Polyol from Algae Oil and Characterization Thereof This example describes the synthesis of a hydroformylated, hydrogenated polyol from algae oil (91% oleate, 5% linoleate, 1.8% palmitate, and 1.12% others; with an Iodine Value (IV) of 88 g $I_2$/100 g). The polyol was characterized by gel permeation chromatography (GPC), Fourier Transform Infrared Spectroscopy (FT-IR), Differential Scanning calorimetry (DSC), and Thermo Gravimetric Analysis (TGA). A 2-L pressure reactor was charged with 450 g of algae oil, 0.45 g of Rh (as acetylacetonato-dicarbonylrhodium(I)), and 2.48 g of triphenylphosphine (TPP) ligand. The vessel was flushed with 4×100 psig syngas and then heated to 90° C. The syngas pressure was maintained at 1000 psi for 6 hours followed by cooling of the vessel to room temperature and venting the syngas. The reactor was opened and charged with 225 mL of isopropanol and 45 g of Raney nickel and closed again. The mixture was then flushed with 4×100 psig of hydrogen, and subsequently heated to 110° C. The hydrogen pressure was maintained at 1000 psi for 5 hours and the reactor was cooled, opened, and diluted with another 100 mL of isopropanol. The reactor contents were filtered through Celite® to remove the Raney nickel and Rh catalysts. After removing the solvents under vacuum, 480 grams of viscous liquid was obtained.

Hydroxyl number of the resulting polyol was determined by ASTM method E1899 to be 173 mg KOH/g (versus 175 mg KOH/g theoretical). The polyol had a viscosity of 2.6 Pa·s at 25° C. Thus, the conversion of oil to polyol was quantitative.

Figure 2:
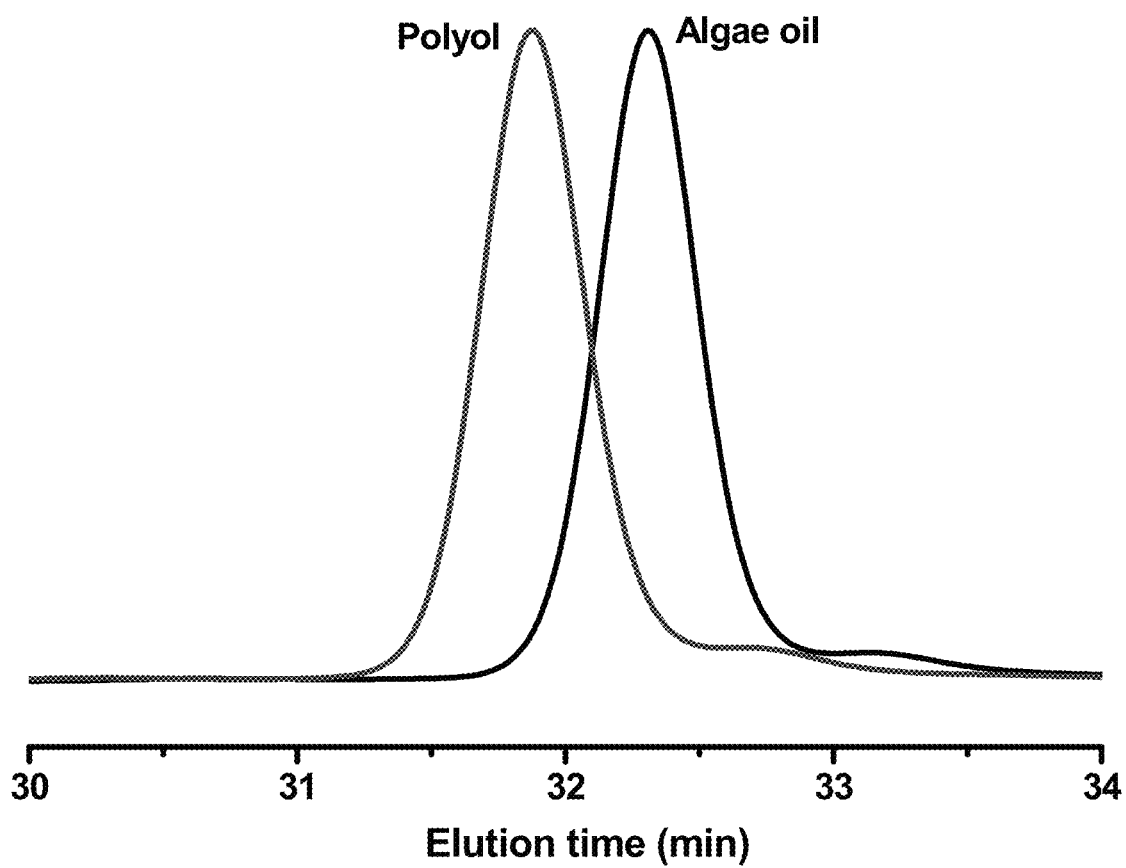
FIG. 2 illustrates GPC curves of algae oil and polyol.

GPC analysis of the polyol product and the algal oil substrate showed that the polyol peak shifted to the left, which was indicative of an increase in molecular weight (MW) compared to the algal oil substrate (FIG. 2). In addition, GPC showed a single, narrow peak of polyol, which confirmed all algae oil starting material converted to polyol.

Figure 3:
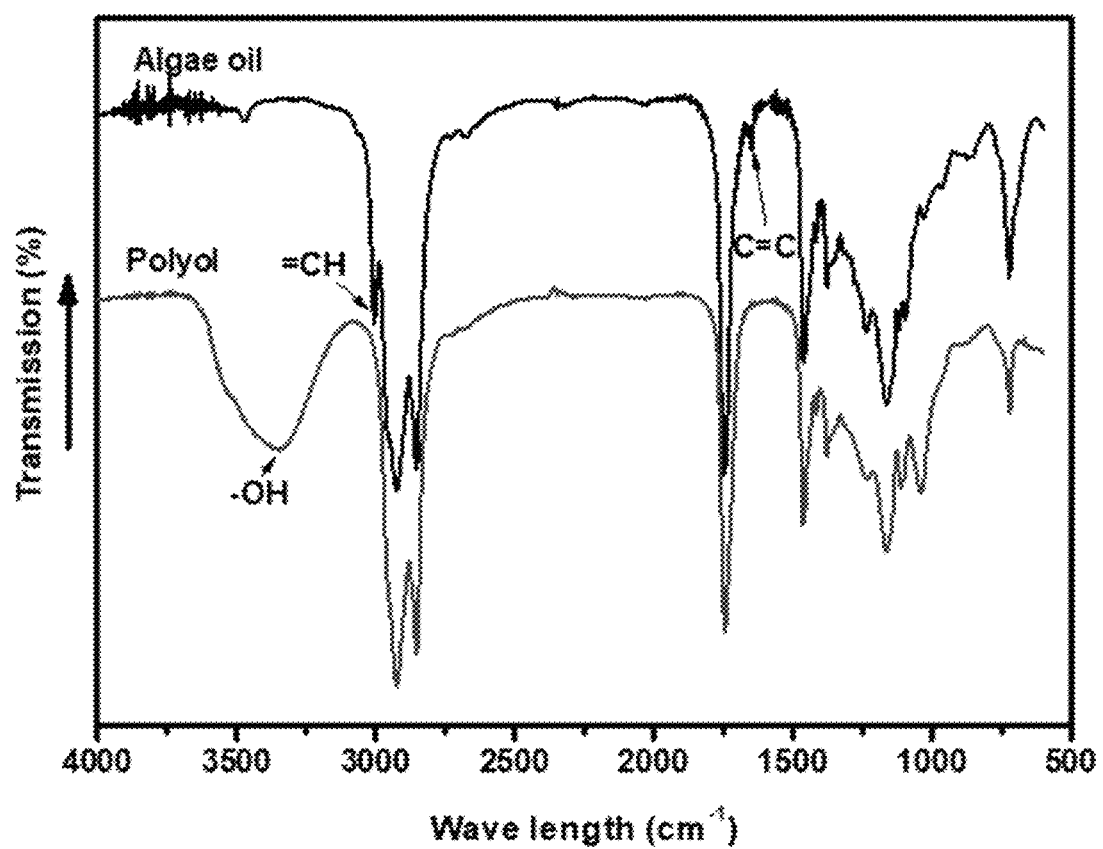
FIG. 3 illustrates the FT-IR spectra of algae oil and polyol.

FT-IR was used to assess the chemical makeup of the samples. Signals at 3005 $cm^{-1}$ and 1650 $cm^{-1}$ that were present in the algae oil (indicative of C=C bonds) were absent in the polyol. The appearance of a broad peak at 3000-3700 $cm^{-1}$ was due to the O—H stretching of the hydroxyl groups formed in the polyol (FIG. 3).

Figure 4:
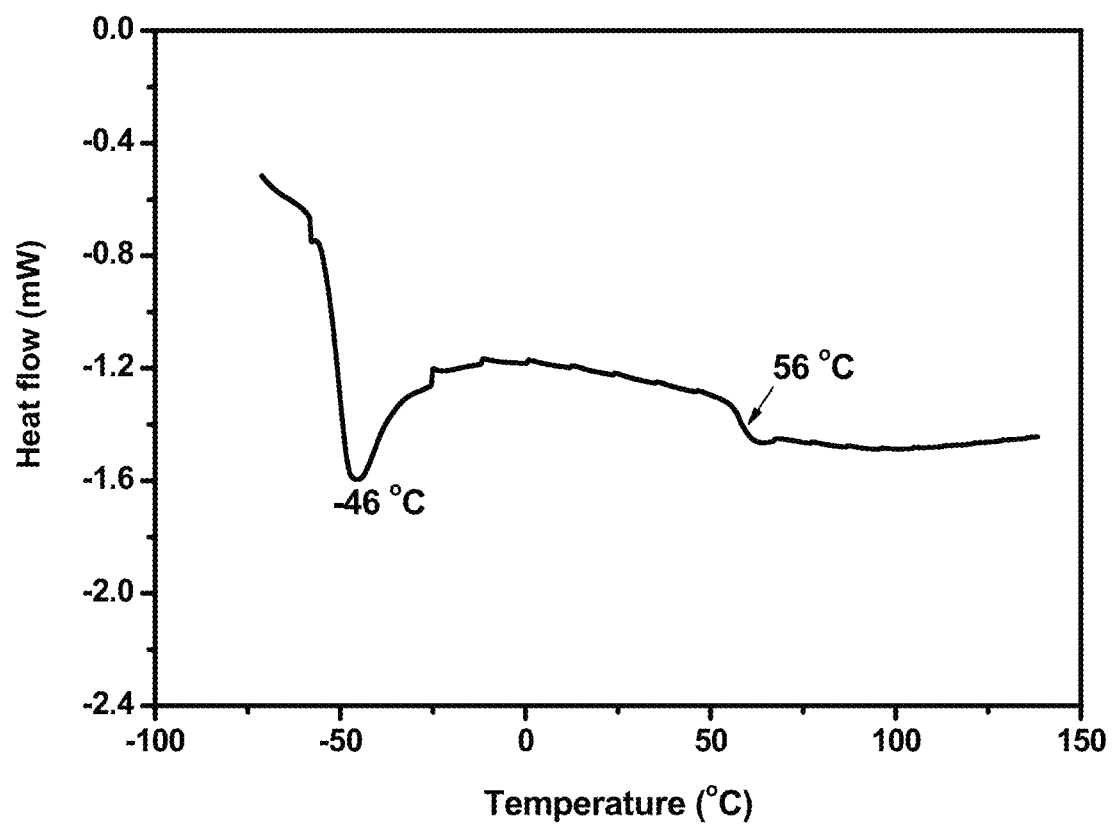
FIG. 4 illustrates a DSC curve of polyol derived from algal oil subjected to hydroformylation.

DSC was used to assess thermal properties of the polyol. The DSC curve showed a melting point ($T_m$) at −46° C. and a signal at 56° C. The signal at 56° C. may be due to melting of fully hydrogenated oleic moieties that failed to undergo hydroformylation but were reduced during the hydrogenation reaction (FIG. 4).

Figure 5:
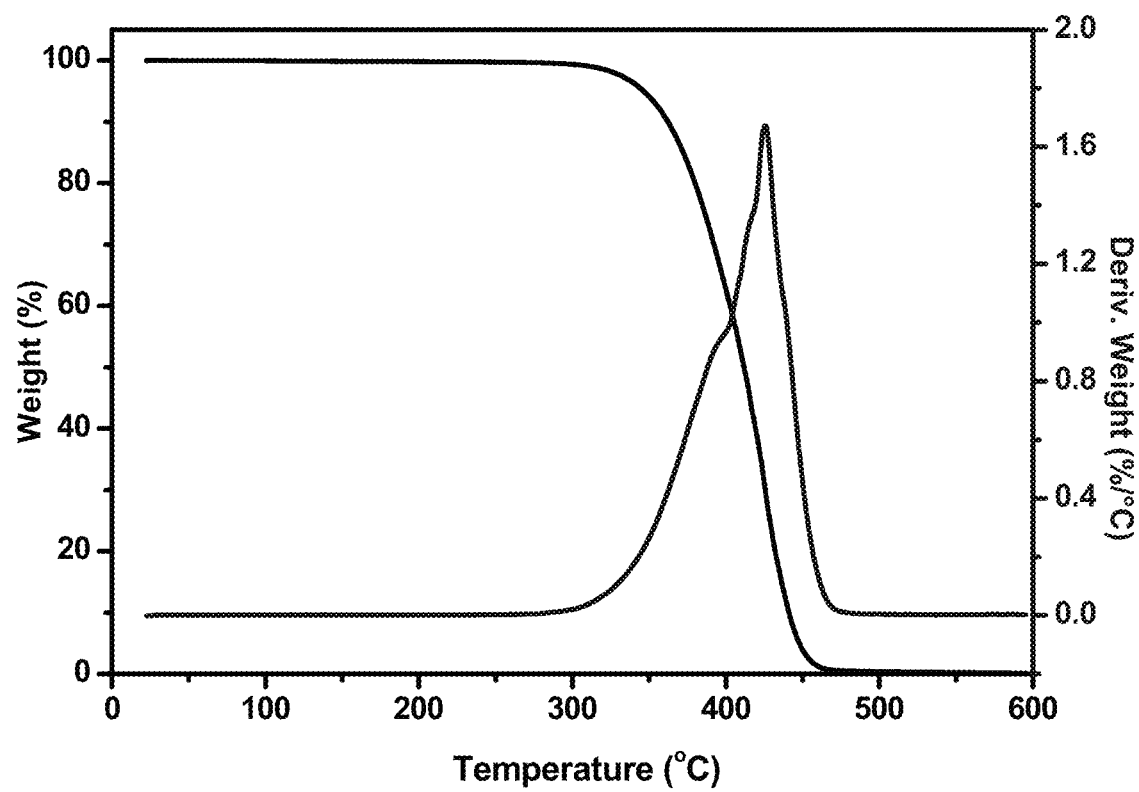
FIG. 5 illustrates a TGA curve of polyol.

Thermal stability of the algal polyol was assessed through TGA. The data, as shown in FIG. 5, indicated that the polyol had excellent thermal stability as evidenced by only 5% weight loss at a temperature of 346° C.

Figure 6:
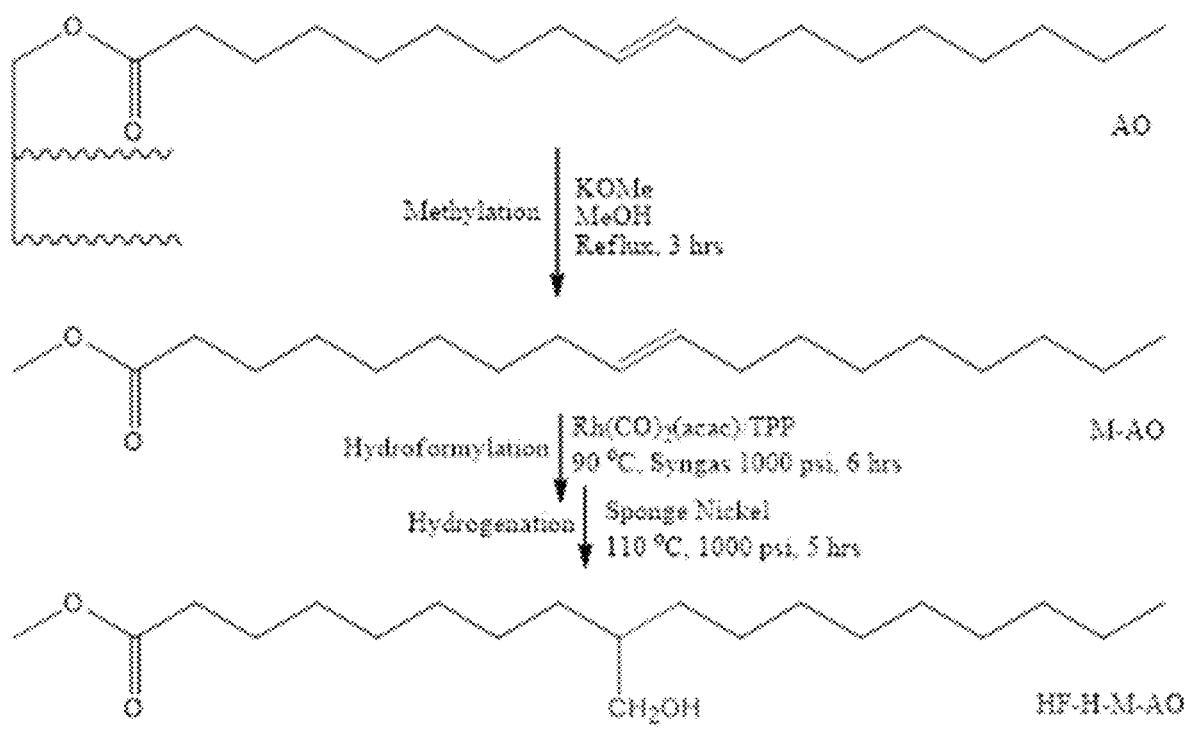
FIG. 6 shows a schematic of methylation, hydroformylation, and reduction reactions of algal oil to form polyol.

Example 2. Preparation of Methylated, Hydroformylated, and Hydrogenated Fatty Acids from Algal Oil Like intact algal triglyceride oils, fatty acids and methyl esters derived from such oils can be hydroformylated. In this example, methylated and hydroformylated fatty acids were prepared in two steps, as shown in FIG. 6. The synthesis involves the methylation of algae oil (91% oleate, 5% linoleate, 1.8% palmitate, and 1.12% others; with an Iodine Value (IV) of 88 g $I_2$/100 g) to produce fatty acid methyl esters, which is followed by hydroformylation and hydrogenation of the methyl esters to form polyols. AO, algae oil; M-AO, methylated algae oil; HF-H-M-AO, methylated and hydroformylated fatty acids.

Generation of fatty acid methyl esters of algal oil was carried out as follows. Algal oil (100 g, ca. 0.115 mol assuming triolein), methanol (165 g, ca. 5.16 mol, ca. 45-fold molar excess to oil), and potassium methoxide (1 g, 1% wt/wt to oil) were combined into 500-mL flask equipped with a condenser. The mixture was stirred vigorously under reflux conditions (70° C.) for 3 hours. The mixture was then cooled to around 50° C. and Amberlite IR120 H resin was added to neutralize the reaction. The mixture was then stirred at 50° C. for 1 hour. The Amberlite IR120 H resin was filtered out and the solvent was removed via rotary evaporation. Glycerol was removed by a separatory funnel, and then washed with 10 mL of water. Residual solvent and water in the organic phase were removed by rotary evaporation under high vacuum at 70° C. for 2 hours.

Figure 7:
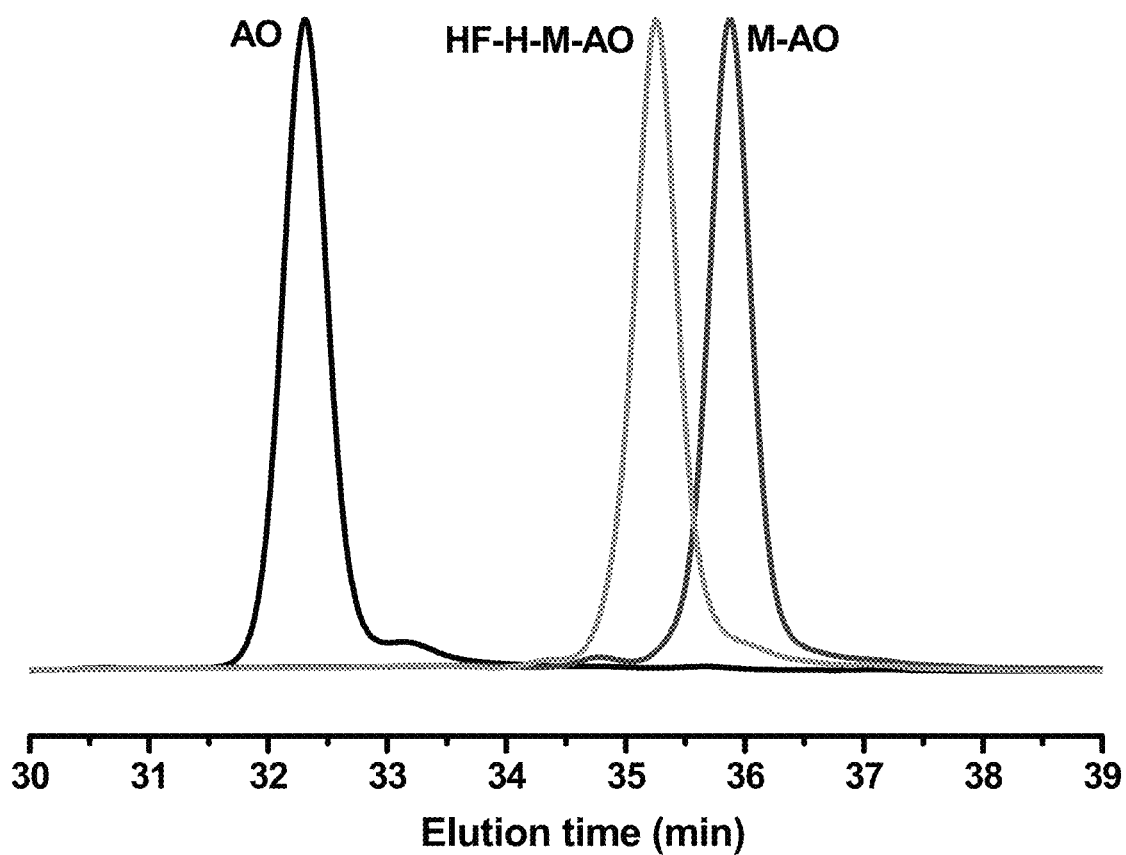
FIG. 7 illustrates the GPC spectra of algal oil (AO), fatty acid methyl esters (M-AO), and hydroformylated, hydrogenated methyl esters of algal oil (HF-H-M-AO).

Hydroformylation of the resulting fatty acid methyl esters was carried out as follows. A 500-mL reactor was charged with methylated algae oil (100 g) and catalyst (0.1 g of Rh(CO)$_2$acac and 0.55 g TPP). The reactor was flushed 4×100 psig with syngas, heated to 90° C. and the syngas pressure was maintained at 1000 psi for 6 hours. After cooling the reactor to room temperature and releasing the syngas, the reactor was opened, and 50 g of isopropanol and 10 g of Raney nickel were added. The mixture was then flushed 4×100 psig with hydrogen and heated to 110° C. at 1000 psi for 5 hours. The reactor was then cooled to room temperature and opened. The mixture was diluted with another 100 mL of isopropanol and filtered through Celite® to remove the Ni and Rh catalysts. Residual solvent was removed by rotary evaporation under low pressure at 60° C., followed by high vacuum at 70° C. for 2 hours. The resulting polyol was characterized by hydroxyl number (OH #), FT-IR, and GPC. Hydroxyl number was assessed by ASTM method E1899 and determined to be 158 mg KOH/g, which was about a 90% conversion rate of fatty acid methyl esters to polyol. A GPC analysis of algal oil, fatty acid methyl esters, and hydroformylated, hydrogenated fatty acid methyl esters is shown in FIG. 7. Algal oil (triglyceride) eluted as a single peak at around 32.5 min. As expected, the elution profile of the fatty acid methyl esters (M-AO; red curve) was shifted to the right due to the significant reduction in molecular weight owing to cleavage from the glycerol backbone, whereas the hydroformylated, hydrogenated product (HF-H-M-AO) eluted slightly sooner due to the corresponding increase in molecular weight.

Figure 8:
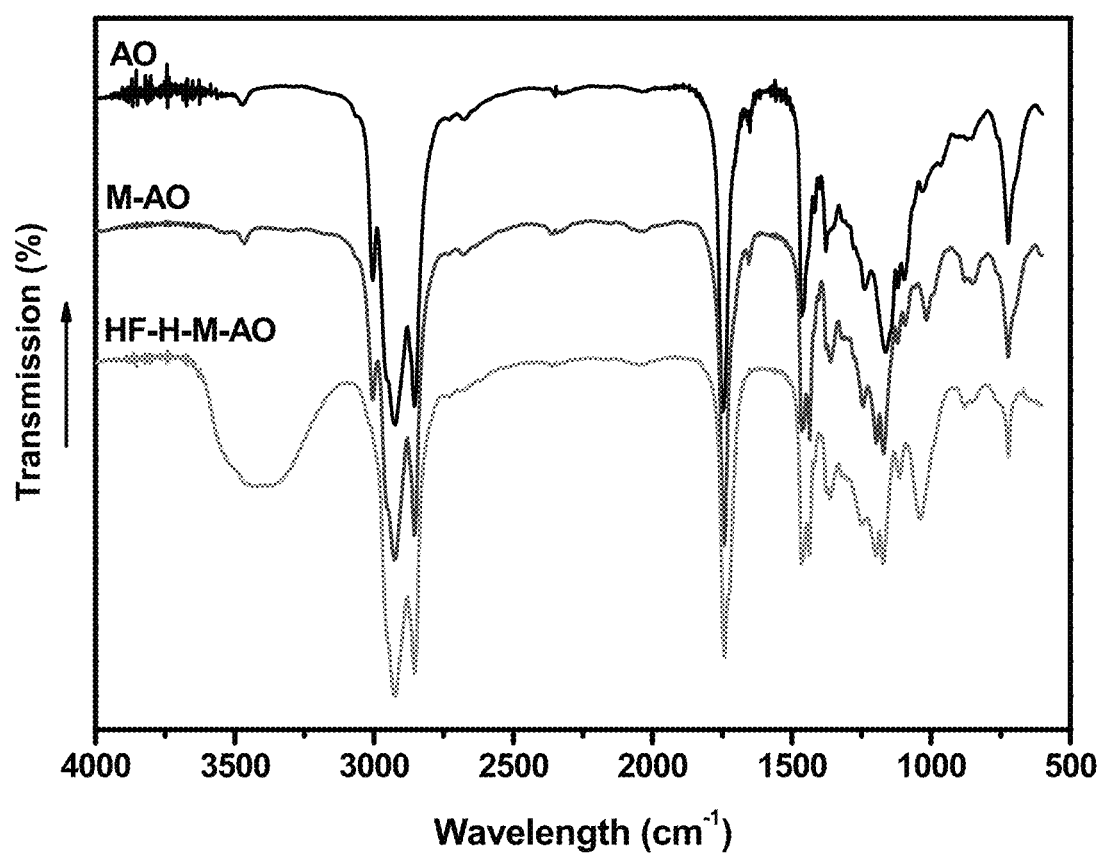
FIG. 8 illustrates the FT-IR spectra of algal oil (AO), methyl esters (M-AO), and hydroformylated, hydrogenated methyl esters (HF-H-M-AO).

FT-IR analysis of algal oil and fatty acid methyl esters derived therefrom both show peaks indicative of C=C bonds at 3005 $cm^{-1}$ and 1640 $cm^{-1}$, but which disappeared after hydroformylation (FIG. 8). A strong, broad OH peak was observed at 3300 $cm^{-1}$ in the hydroformylated, hydrogenated fatty acid methyl esters.

Figure 9:
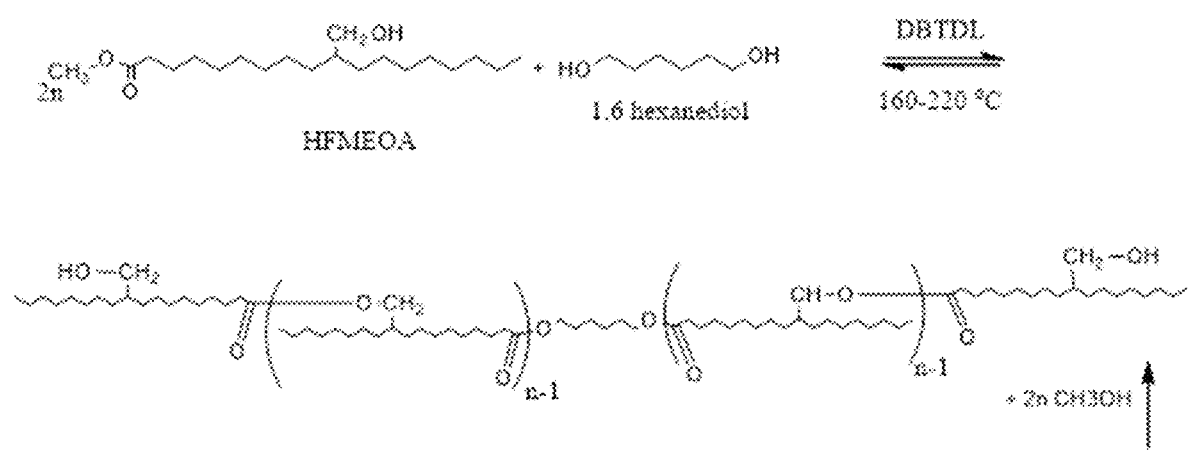
FIG. 9 shows a schematic of the synthesis and structure of polyester diols based on HFMEOA initiated by 1,6-HD and catalyzed by DBTDL.

Example 3. Synthesis of Polyester Diols from Hydroformylated, Hydrogenated Methyl Esters of Oleic Acid Hydroformylated, hydrogenated methyl esters of oleic acid (HFMEOA; derived from algal oil comprised of 91% oleate, 5% linoleate, 1.8% palmitate, and 1.12% others; with an Iodine Value (IV) of 88 g $I_2$/100 g) was prepared as outlined in Example 2. 1,6-hexanediol (1,6-HD) was used as soft segments in polyurethane (PU) elastomeric materials. A polyester diol was prepared by polyesterification of HFMEOA using 1,6-HD as an initiator and 0.14% DBTDL as catalyst. This reaction is shown schematically in FIG. 9.

The ratio of HFMEOA and 1,6-HD for making soft segments for PU elastomers largely depends on the desired molecular weight of the diol being developed. In this example, diol molecular weights of 1000 and 2000 were synthesized to serve as soft segments in elastomeric PUs.

As an example, raw material content for MW=2000 was calculated using the following equation. The equation can be used to determine the number of moles of HFMEOA required to react with one mole of 1,6-HD to obtain the desired molecular weight of the soft segment. $M_{polyol}$, desired molecular weight of polyester; $M_{1,6HD}$, molecular weight of 1,6 hexanediol (118.1 g/mol); $M_{HFMEOA}$, molecular weight of HFMEOA (328.3 g/mol); $M_{CH3OH}$, molecular weight of methanol (32 g/mol); and n, number of moles of HFMEOA (or methanol) needed to obtain the desired $M_{polyol}$.

$$M_{polyol} = M_{1,6HD} + n(M_{HFMEOA} - M_{CH3OH})$$

For a desired polyol with a MW of 2000, moles of HFMEOA and moles of methanol were calculated as follows:

2000=118.1+n(328.3−32)

n=6.351 mol of HFMEOA or mol of methanol

Thus, for each mol of 1,6-HD, 2085 g of HFMEOA and 203.2 g of methanol were required.

For a desired polyol with a MW of 1000, moles of HFMEOA were calculated as follows:

1000=118.1+n(328.3−32)

n=2.976 mol of HFMEOA or mol of methanol

Thus, for each mol of 1,6-HD, 977 g of HFMEOA and 95.2 g of methanol were required.

Based on the calculations above, two formulations of polyester polyol (MW of 2000 and 1000) were prepared. For the 2000 MW polyester polyol, 52.12 g of HFMEOA, 2.95 g of 1,6-HD, and 0.08 g of (0.14%) DBTDL catalyst were used. For the 1000 MW polyester polyol, 44.00 g of HFMEOA, 5.5 g of 1,6-HD, and 0.07 g of DBTDL (0.14% catalyst) were used. For both syntheses, a Dean-Stark Trap was used as the polyesterification reactor. The reactor was charged with HFMEOA, 1,6-HD, and DBTDL. The reactor was heated initially to 160° C. with a nitrogen sparge. Through the continuous removal of methanol, the equilibrium of polyesterification was shifted to the formation of polyester polyol. The temperature was then increased in a step-wise fashion as follows: 160° C. for 1 hour, increasing to 180° C. for 3 hours, increasing to 200° C. for 3 hours, and finally increasing to 210° C. for 3 hours. The resulting polyols were characterized by OH #, viscosity, acid value, MW (calculated based on OH #), GPC, and FT-IR. The hydroxyl number, viscosity, acid value, and MW data are presented in TABLE 2.

TABLE 2

| Characteristic | Algal HF-Polyol (M = 2000) | Algal HF-Polyol (M = 1000) |
|---|---|---|
| Hydroxyl number (mg KOH/g) | 44.2 | 88.2 |
| Viscosity @ 25° C. (Pa · s) | 7.79 | 2.60 |
| Acid value (mg KOH/g) | 0.2 | 0.32 |
| MW (g/mol) | 2540 | 1270 |

Figure 10:
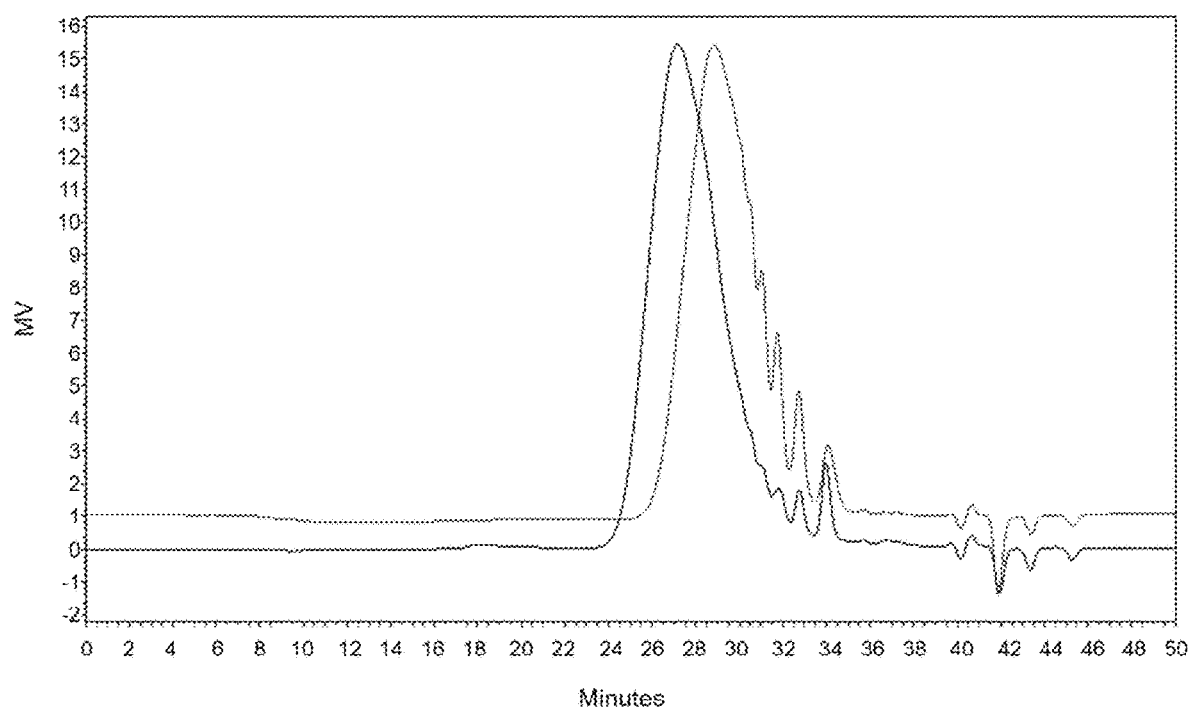
FIG. 10 illustrates an overlay of GPC curves of Algal HF-Polyol M=2000 and Algal HF-Polyol M=1000.

FIG. 10 shows an overlay of two GPC curves for algal polyols of MW 2000 (left peak; black line) and MW 1000 (right peak; blue line). As expected, each polyol spectrum exhibited a series of smaller MW peaks resulting from partial reactions.

Figure 11:
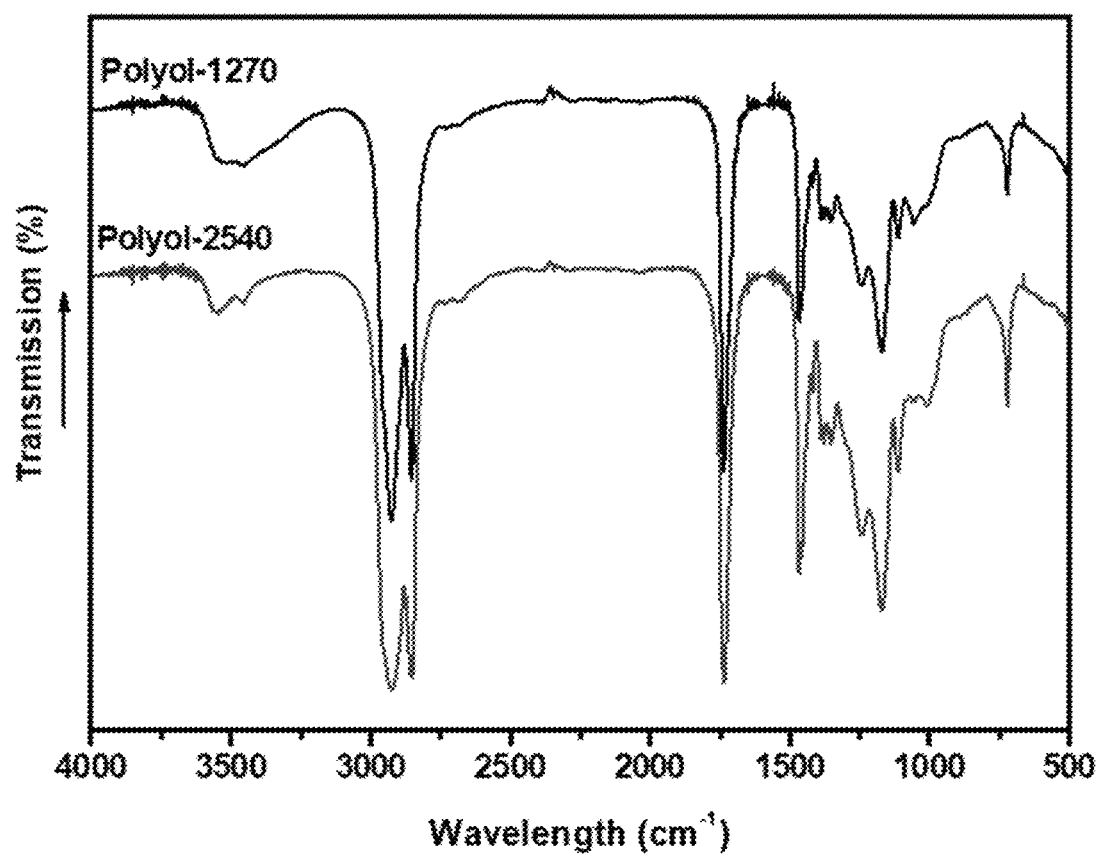
FIG. 11 illustrates the FT-IR spectra of both polyester diols prepared by polyesterification of HFMEOA initiated by 1,6-HD.

FIG. 11 shows the FT-IR spectra of both polyester diols (Polyol-1270 and Polyol-2540) prepared by polyesterification of HFMEOA initiated by 1,6 hexanediol. The absorption bands of hydroxyl groups at 3400-3500 $cm^{-1}$ are observed. No absorption of double bonds at 3009 $cm^{-1}$ is observed. The presence of carbonyl group from ester bonds at around 1750 $cm^{-1}$, C—O bonds at around 1100 $cm^{-1}$ are also observed.

Example 4. Preparation of Polyurethane Elastomers from Polyester Diols, Isocyanate Rubinate® 9225 (a Monomeric MDI), and Butanediol (1,4-BD)

Figure 12:
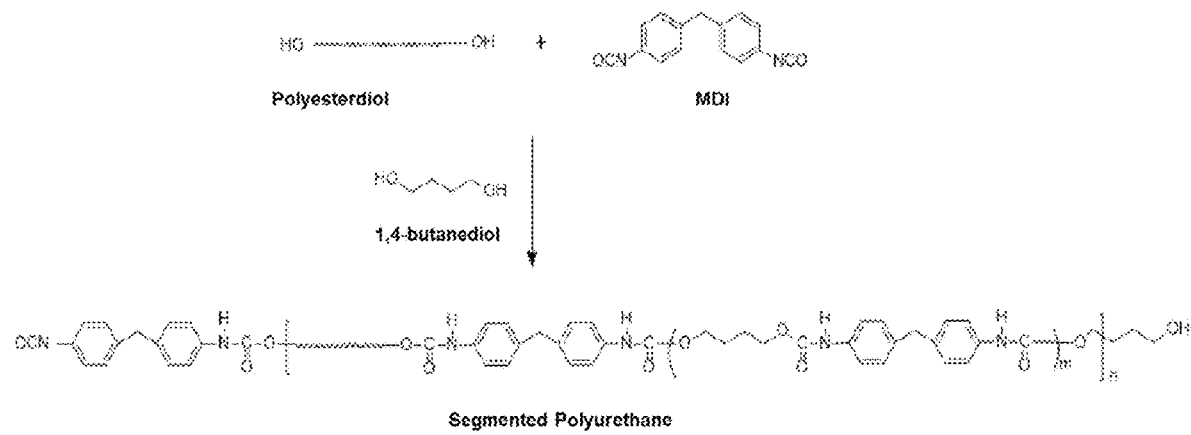
FIG. 12 shows the reaction scheme for preparation of PU elastomer.

In this example, a pre-polymer technique was used to prepare the PU elastomers. Using this method, a polyester-diol, prepared as in Example 3, was reacted with a calculated amount of isocyanate to obtain a "quasi-pre-polymer". The quasi pre-polymer contains polyols with terminal isocyanate groups and free methylene diphenyl diisocyanate (MDI). The quasi pre-polymer was subsequently reacted with a chain extender (1,4-BD) to obtain the final polymer, as illustrated in FIG. 12.

PU elastomeric materials are comprised of "hard" and "soft" segments. The ratio of hard and soft segments is referred to as the soft segment content (SSC). In this example, a PU elastomer with 70% SSC using a polyol having MW of approximately 2000 was prepared. The second PU elastomer with 50% SSC using a polyol having a MW of approximately 1000 was also prepared. Polyester diols were prepared as outlined in Example 3. The formulation components are shown in TABLE 3. The polyols were derived from hydroformylated fatty acid methyl esters, 1,4-BD (MW=90, EW=45), and pure MDI (MW=250, EW=125). The polyols had MWs of 2450 and 1350, and OH #s of 44 (AHF-44) and 88 (AHF-88), respectively.

TABLE 3

| Sample | Polyol (g) | MDI (g) | 1,4-BD (g) |
|---|---|---|---|
| AHF-44-70% SSC | 15 | 4.4 | 1.1 |
| AHF-88-50% SSC | 18 | 13.5 | 3.6 |

Figure 13:
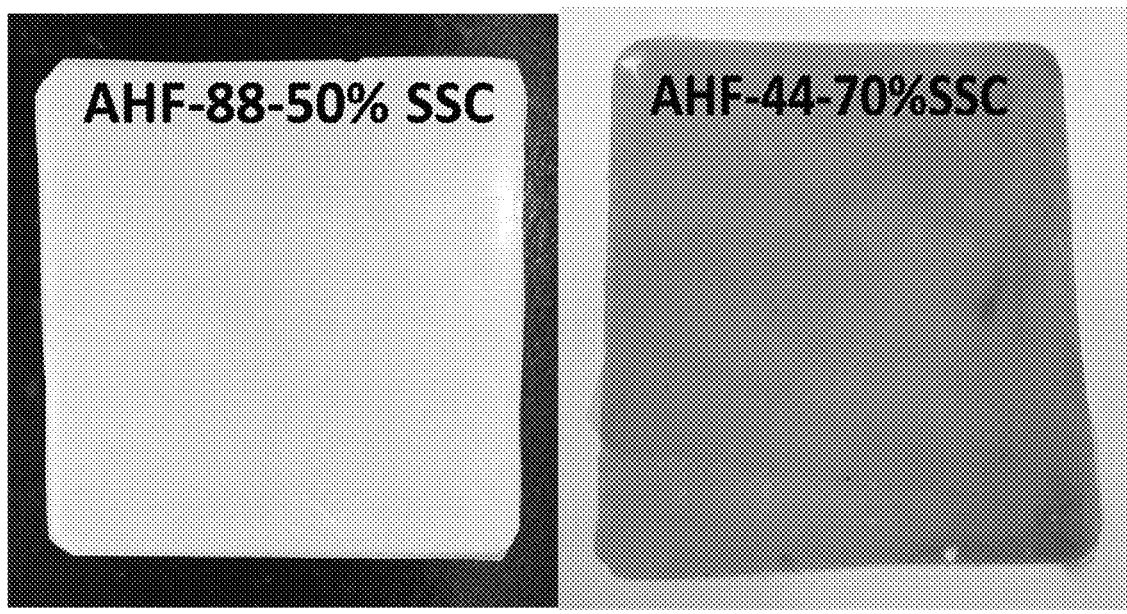
FIG. 13 shows the physical appearance of elastomeric materials prepared with algal oil derived polyols.

For each formulation, polyols were charged into a 125-mL Erlenmeyer flask, heated to 70° C., and kept under low vacuum for several minutes. 1,4-BD was then injected with agitation and the mixture was incubated at 70° C. until the 1,4-BD was completely incorporated. MDI was then injected into the mixture with continued agitation for 2 min and transferred into molds that were preheated to 110° C. Images of the 50% and 70% SSC cast urethanes are shown in FIG. 13. Samples were cured overnight, and post-cured at room temperature for 24 hours before testing. Samples were subjected to thermal (DSC) and mechanical testing, including assessment of tensile properties using ASTM D638-03 and shore hardness using a Shore A durometer. The results are showing in TABLE 4. $T_g$, glass transition temperature; $T_m$, melting temperature.

TABLE 4

| PU elastomer | Density (g/cm³) | $T_g$ (° C.) | $T_m$ (° C.) | Tensile strength (MPa) | Elongation (%) | Young modulus (MPa) | Shore A Hardness |
|---|---|---|---|---|---|---|---|
| AHF-88-50% SSC | 1.03 | −52 | 210 | 6.143 | 64 | 33 | 50 |
| AHF-44-70% SSC | 1.03 | −62 | 190 | 2.417 | 85 | 3.2 | 89 |

Figure 14:
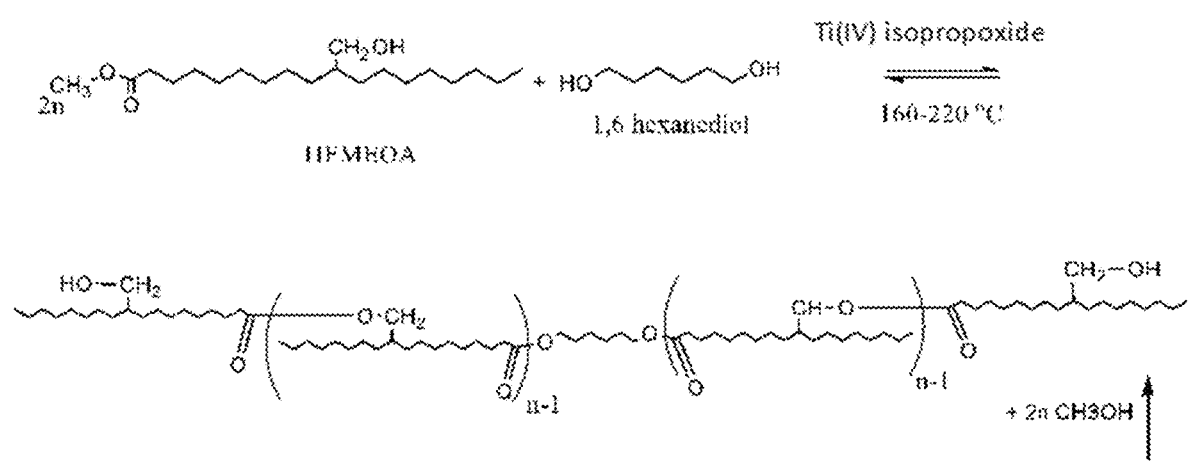
FIG. 14 shows the synthesis and structure of polyester diols based on HFMEOA initiated by 1,6-HD and catalyzed by either DBTDL or Ti(IV) isopropoxide.

Example 5. Polymerization of Polyester Polyols by Transesterification with Hexanediol and Titanium Isopropoxide as Catalyst FIG. 14 shows a schematic of the polymerization reaction in which HFMEOA was reacted with 1,6-HD and Ti(IV) isopropoxide. HFMEOA was prepared, as outlined in Example 2, in 5×100 g batches. The OH #, viscosity, % conversion, and % yield of each batch are shown in TABLE 5. [a] Conversion was calculated from experimental and theoretical OH #: (OH #$_{exp}$/OH #$_{th}$)*100%. The OH #$_{th}$ is 174 mg KOH/g. [b] Yield was calculated from experimental and theoretical product weight (110.8 g): (Weight$_{exp}$/110.8) *100%.

TABLE 5

| HF-H-M-AO | OH# (mg KOH/g) | Viscosity (mPa · S) | Conversion[a] (%) | Weight (g) | Yield[b] (%) |
|---|---|---|---|---|---|
| 1 | 174 | 54 | 100 | 97 | 87.5 |
| 2 | 170 | | 97.7 | 103 | 92.9 |
| 3 | 167 | | 96.0 | 102 | 92.0 |
| 4 | 170 | | 97.7 | 103 | 92.9 |
| 5 | 169 | | 97.1 | 104 | 93.8 |

Figure 15:
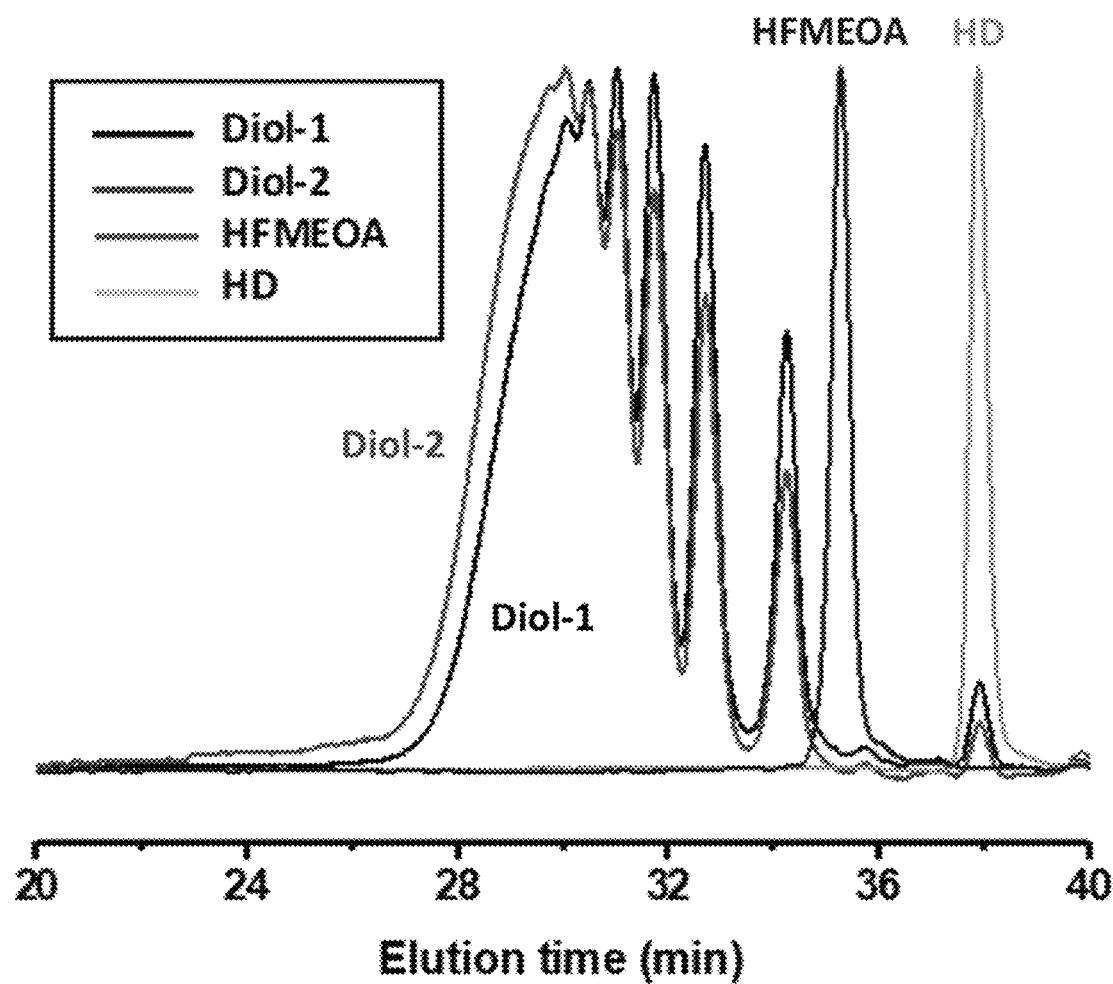
FIG. 15 illustrates GPC curves for both polyesterdiols (Diol-1 and Diol-2), HFMEOA, and 1,6-HD.
Figure 16:
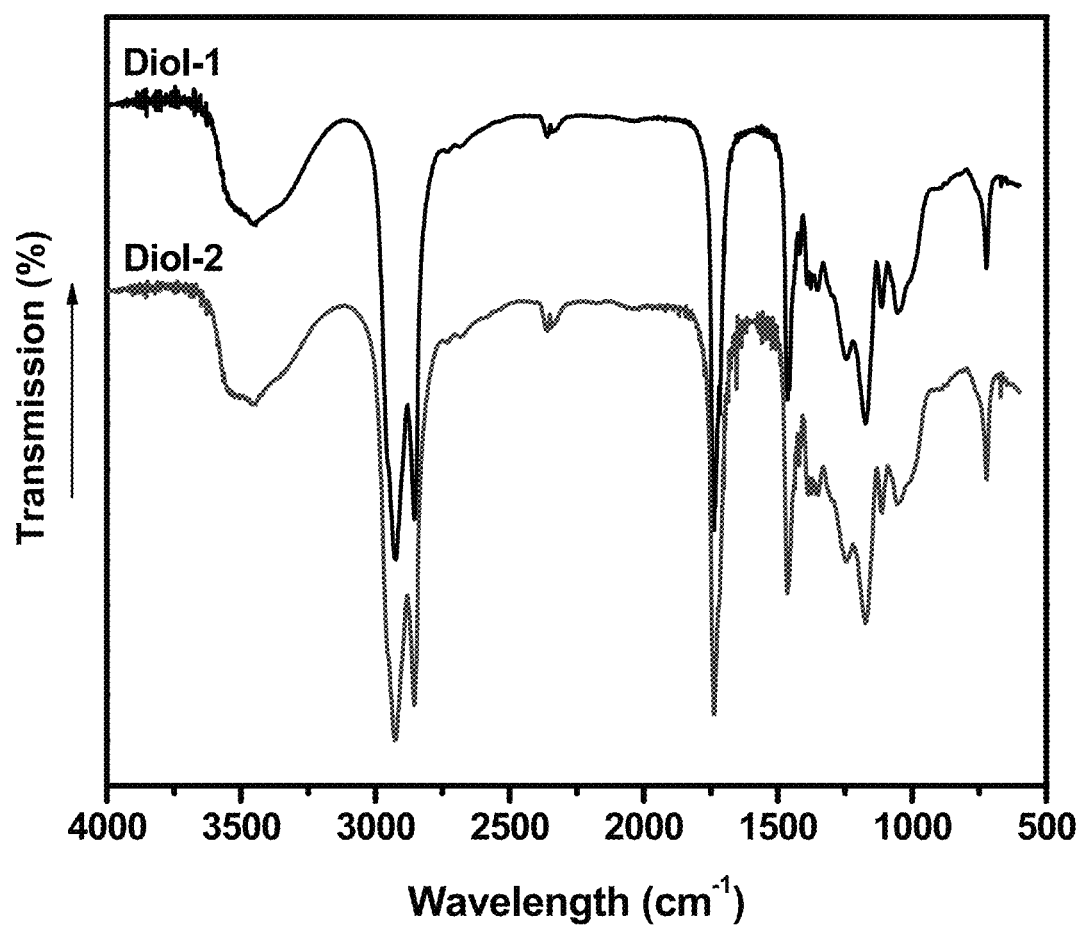
FIG. 16 illustrates the FT-IR spectra for polyesterdiols 1 and 2.

To prepare a polyesterdiol with an average MW of 1000, two separate reactions (Diol-1 and Diol-2) were prepared. For each reaction, HFMEOA (100 g, 0.30 mol), 1,6-HD (12.5 g, 0.106 mol), and titanium isopropoxide (0.563 g, or 0.5 wt % of HFMEOA+1,6-HD) were charged into a 500-mL flask equipped with a Dean-Stark Trap and a condenser. Each mixture was stirred vigorously and heated at 150° C. for 2 hours with nitrogen sparge. The temperature was then increased to 180° C. and the process was continued for 3 additional hours. The temperature was then further increased to 200° C. for an additional 3 hours. Each mixture was cooled to room temperature. Each mixture was dissolved in chloroform and decolored with active carbon for 1 hour. After removing active carbon by filtration over Celite®, residual solvent was removed by rotary evaporation under high vacuum at 70° C. for 2 hours. The reaction yielded 94 g of pale brown, transparent product with approximately 91% yield [MW of methanol (CH$_3$OH) is 32.08; Theoretical weight of diol: 113.06−32.04*0.3=103.45 g; Yield of diol: 94.0/103.45*100%=90.9%]. The two polyesterdiols were further characterized by measuring OH #, acid value (AV), viscosity, OH # equivalents and MW (TABLE 6). The chemical structures of the two polyesterdiols were further assessed by GPC (FIG. 15) and FT-IR (FIG. 16).

TABLE 6

| Polyesterdiol | OH# (mg KOH/g) | AV (mg KOH/g) | Viscosity (Pa · S) | OH# Equiv. (= 56100/OH#) | Mw (= 2 × OH Equiv.) |
|---|---|---|---|---|---|
| Diol-1 | 96 | 0.5 | 1.4 | 584 | 1168 |
| Diol-2 | 93 | 0.6 | 1.4 | 603 | 1206 |
| Combined | 92 | 0.3 | 1.5 | 610 | 1220 |

In the GPC spectra, the two higher MW polyesterdiols (Diol-1 and Diol-2) and lower MW partial products eluted first. The lower MW starting materials, 1,6-HD and HFMEOA, eluted later.

In the FT-IR, strong absorption bands of the hydroxyl groups at 3400-3500 cm$^{-1}$ were observed. No absorption of double bonds at 3009 cm$^{-1}$ were observed. Absorption bands at around 1750 cm$^{-1}$ arising from carbonyl groups from ester bonds were also observed.

Example 6. Preparation of Polyurethane Elastomers from Polyester Diols, Isocyanate Rubinate® 9225, and 1,4-BD Algal oil polyols (AOP) pooled from Example 5 and Rubinate® 9225 were formulated as with 1,4-BD to prepare elastomeric PUs with targeted SSC content of 50-60%. The two formulations are shown in TABLE 7.

TABLE 7

| Sample | AOP (g) | AOP (eq) | 1,4-BD (g) | 1,4-BD (eq) | Rubinate ® 9225 (g) |
|---|---|---|---|---|---|
| JH-AOP-50% SSC | 10.29 | 0.0169 | 2.01 | 0.0447 | 8.36 |
| JH-AOP-60% SSC | 12.34 | 0.0203 | 1.35 | 0.030 | 6.84 |

Figure 17:
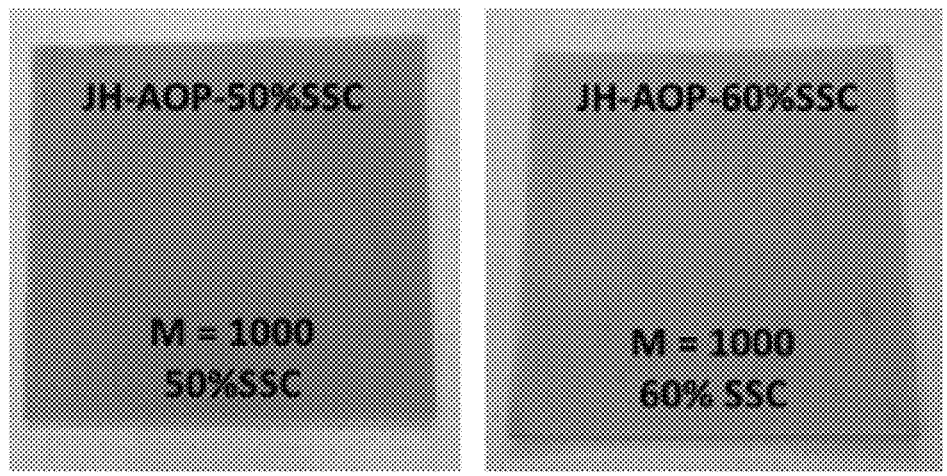
FIG. 17 shows casts of the 50% and 60% SSC elastomeric materials.

Polyesterdiols were charged into a 125-mL Erlenmeyer flask, heated to 70-80° C., and kept under low vacuum for several minutes to remove air. 1,4-BD was injected into the mixture with strong agitation and the mixture was continued to heat at 70° C. while stirring. Rubinate® 9225 was injected into the mixture and the mixture was stirred for approximately 2 min before transferring into a 120° C. pre-heated mold. The samples were then cured overnight at 120° C., post-cured at room temperature for 24 hours, and tested for thermal (DSC) and mechanical properties, including tensile strength (ASTM D68-03) and hardness (TABLE 8). FIG. 17 shows an image of the 50% and 60% SSC cast urethanes. TABLE 9 shows the glass transition temperature ($T_g$) and hard segment melting point ($T_m$) of the elastomeric PUs with SSC content of 50% and 60% compared to the elastomeric PU with SSC content of 70%.

TABLE 8

| Sample | Tensile Strength (MPa) | Elongation (%) | Yield Stress (MPa) | Young Modulus (MPa) | Shore A Hardness |
|---|---|---|---|---|---|
| JH-AOP-50% SSC | 8.0 | 179 | 7.4 | 11 | 89 |
| JH-AOP-60% SSC | 9.7 | 117 | 9.4 | 31 | 87 |

TABLE 9

| Sample | $T_g$ (° C.) | Hard segment $T_m$ (° C.) |
|---|---|---|
| JH-AOP-50% SSC | −42 | 185 |
| JH-AOP-60% SSC | −41 | 157 |
| MI-AOP-70% SSC | −40 | 60 |

Example 7. Preparation of Polyurethane Cast Resins from Hydroformylated, Hydrogenated High Oleic Algal Oil and Three Different Isocyanates, Including Rubinate® 44 (R44, Huntsman; a Pure MDI), and Rubinate® 9225 (R9225, Huntsman; Uretonimine Modified Monomeric MDI), and Rubinate® M (RM, Hunstman; a Standard Polymeric, Crude MDI)

In this example, catalyst was not used. With 1% of DBTDL, the gel point of the reaction was just 10 seconds. A 10-fold reduction in DBTDL increased the gel point to just 52 seconds, which was still too short of a pot life for most applications, although catalyst loading method and type can be varied to optimize the gel point. All cast urethane reactions were carried out under identical conditions. Polyols were vacuumed at room temperature for 10 min, removed from the vacuum followed by the addition of isocyanate. The polyol-isocyanate mixture was mixed well and returned to vacuum for 2 min before transferring into a stainless-steel mold heated at 110° C. in an oven overnight. The formulations and properties of the resins are listed in TABLE 10. [a] Isocyanate index is 1.02. [b] Glass transition temperature. [c] Temperature of 5% weight loss.

TABLE 10

| Film | HF-AO-Polyol (g) | Isocyanate[a] (g) | Tensile strength at break (MPa) | Break elongation (%) | $T_g$[b] (° C.) | $T_{5\%}$[c] (° C.) |
|---|---|---|---|---|---|---|
| Cast-1 | 13 | R44, 4.96 | 3.45 ± 0.52 | 84.9 ± 11.9 | −1.6 | 338 |
| Cast-2 | 13 | R9225, 5.28 | 6.17 ± 0.12 | 94.9 ± 2.2 | 3.8 | 342 |
| Cast-3 | 13 | RM, 5.36 | 11.9 ± 1.2 | 68.7 ± 1.4 | 15.4 | 345 |

Figure 18:
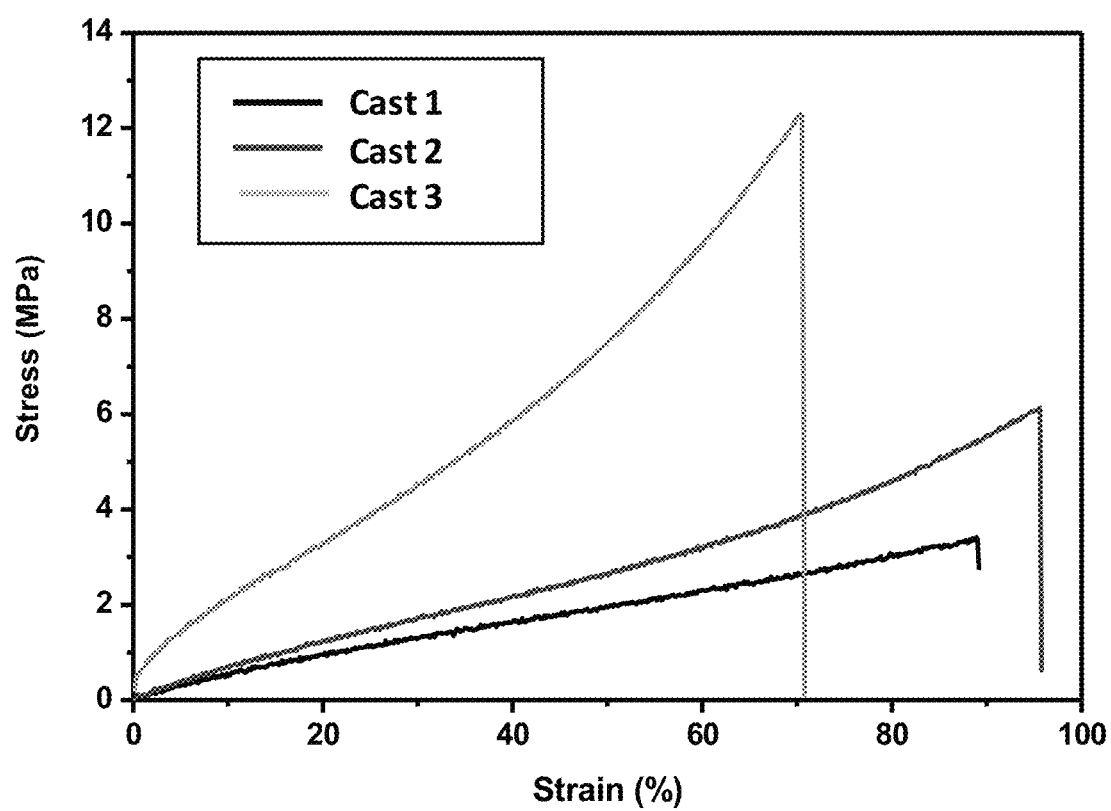
FIG. 18 illustrates stress-strain curves of cast resins.
Figure 19:
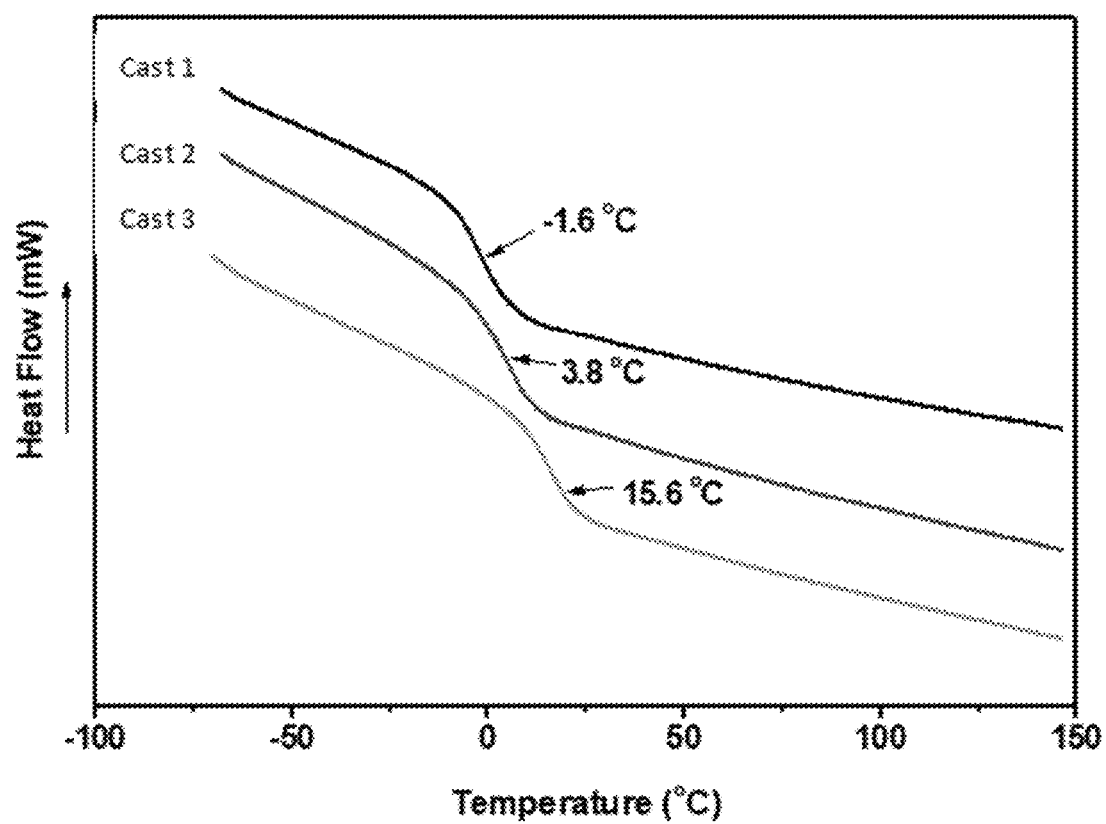
FIG. 19 illustrates DSC curves of cast resins.
Figure 20:
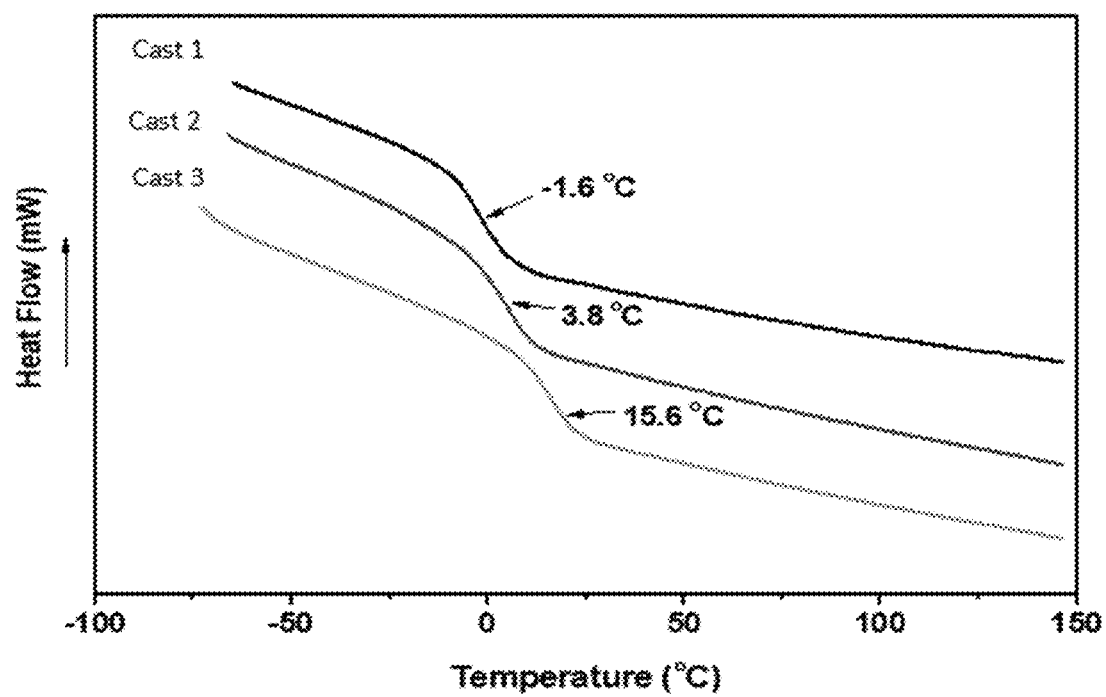
FIG. 20 illustrates TGA curves of cast resins.

The cast urethane properties are related to the type of isocyanate used. Tensile strength (FIG. 18), glass transition temperature (FIG. 19), and temperature at 5% weight loss (FIG. 20) increased with increasing functionality of the isocyanate. Since $T_g$ values were below room temperature, the polymers were in the rubbery state. At room temperature, the polymers exhibited high elongations and reduced strength. However, the polymers would have high strength for use as elastomers and would be strong and tough for use as adhesives. Since these polyols have hydroxyl numbers similar to castor oil, the polyols are a potentially interesting alternative to castor oil with the added advantage having no double bonds (i.e. higher oxidative stability).

Example 8. Preparation of Polyurethane Hard Foams from Hydroformylated, Hydrogenated High Oleic Algal Oil (Example 1)

Rigid foams with different densities were made from hydroformylated, hydrogenated high oleic algal oil in formulations comprised of the algal polyol (polyol), glycerol (GLY), B8871 (TEGOSTAB® surfactant, Evonik), ZF-22 (JEFFCAT® amine catalyst, Huntsman), DBTDL (dibutyltin dilaurate, Evonik), DMEA (Jeffcat amine catalyst, Huntsman), water (as a blowing agent), and isocyanate (Rubinate® M; RM). The various formulations with corresponding cream time, rise time, and tack-free time are shown in TABLE 11.

TABLE 11

| Foam-2-1 | Polyol (g) | GLY (g) | B8871 (g) | ZF-22 (g) | | Water (g) | RM (g) | Total (g) | Mixing time (s) | Cream time (s) | Rising time (s) | Tackle free time (s) |
|---|---|---|---|---|---|---|---|---|---|---|---|---|
| | 90 pph 18 | 10 pph 2 | 2 pph 0.4 | 0.5 pph 0.1 | | 3 pph 0.6 | 27.6 | 48.7 | 8 | 42 | 170 | 307 |
| Foam-2-2 | Polyol (g) | GLY (g) | B8871 (g) | ZF-22 (g) | DBTDL (g) | Water (g) | RM (g) | Total | | | | |
| | 90 pph 18 | 10 pph 2 | 2 pph 0.4 | 0.5 pph 0.1 | 0.2 pph 0.04 | 3 pph 0.6 | 27.6 | 48.7 | 8 | — | 20 | |
| Foam-2-3 | Polyol (g) | GLY (g) | B8871 (g) | ZF-22 (g) | | Water (g) | RM (g) | Total | | | | |
| | 90 pph 18 | 10 pph 2 | 2 pph 0.4 | 1 pph 0.2 | | 3 pph 0.6 | 27.6 | 48.8 | 8 | 12 | 60 | 132 |
| Foam-2-4 | Polyol (g) | GLY (g) | B8871 (g) | DMEA (g) | | Water (g) | RM (g) | Total | | | | |
| | 90 pph 9 | 10 pph 1 | 2 pph 0.2 | 1 pph 0.1 | | 3 pph 0.3 | 13.8 | 24.4 | 8 | 50 | 92 | 152 |
| Foam-1 | Polyol (g) | GLY (g) | B8871 (g) | ZF-22 (g) | | Water (g) | RM (g) | Total | | | | |

TABLE 11-continued

| | 90 pph | 10 pph | 2 pph | 1 pph | 1 pph | | | | | | |
|---|---|---|---|---|---|---|---|---|---|---|---|
| | 27 | 3 | 0.6 | 0.3 | 0.3 | 31.5 | 62.7 | 8 | 11 | 60 | 147 |

| Foam-3 | Polyol (g) | GLY (g) | B8871 (g) | ZF-22 (g) | Water (g) | RM (g) | Total | | | | |
|---|---|---|---|---|---|---|---|---|---|---|---|
| | 90 pph | 10 pph | 2 pph | 1 pph | 6 pph | | | | | | |
| | 9 | 1 | 0.2 | 0.1 | 0.6 | 18.7 | 29.6 | 8 | 7 | 65 | 132 |

Hard foams of varying densities were produced by keeping total polyol (glycerol+algal polyol) and surfactant (pph) constant, while varying catalyst loading, catalyst type, water, and isocyanate. As shown in TABLE 11, the foam with 0.5 pph of ZF-22 (Foam-2-1) had far too long of a tack-free time (307 s). However, when 0.2 pph of DBTDL was added (Foam-2-2), the reaction was too fast to observe a cream time and the foam cell structure was poor. Increasing the content of ZF-22 from 0.5 pph to 1 pph (Foam-2-3) improved the processing times. Foam properties are listed in TABLE 12. Compressive strength was directly correlated with density of the foam.

TABLE 12

| Foam | Density (kg/m$^3$) | Compressive strength (kPa) |
|---|---|---|
| Foam-2-1 | 56 | 303 |
| Foam-2-2 | 89 | 503 |
| Foam-2-3 | 68 | 399 |
| Foam-2-4 | 61 | 361 |
| Foam-1 | 122 | 1080 |
| Foam-3 | 42 | 248 |

Example 9. Preparation of Polyurethane Adhesives from Hydroformylated, Hydrogenated High Oleic Algal Oil (Example 1) and Rubinate® 9225 (R9225, Huntsman, Uretonimine-Modified Monomeric MDI)

Catalyst was not used in this example. Oak and aluminum were used as substrates to assess PU adhesiveness. Six g of hydroformylated, hydrogenated algal polyol (OH #=169 mg KOH/g, EW=330) was combined with 2.47 g of Rubinate® 9225 (NCO=31.5%, EW=133.3, Functionality=2.06), mixed well, and spread over 1 square inch area of substrate. Another piece of substrate was then overlapped along the area to which adhesive had been applied. The two pieces were clamped and cured at 80° C. for 12 hours. Curing at high temperature was not required, but accelerated the reaction and shortened the waiting time prior to testing. The resulting adhesives were tested according to ASTM standards D 2339—Standard Test Method for Strength Properties of Adhesives in Two-Ply Wood Construction in Shear by Tension Loading and D 1002—Standard Test Method for Apparent Shear Strength of Single-Lap-Joint Adhesively Bonded Metal Specimens by Tension Loading (Metal-to-Metal). Adhesives properties are listed in TABLE 13. Both wood and metal failures were cohesive. Lap shear strength of wood and aluminum were 2.5 MPa and 1.4 MPa, respectively.

TABLE 13

| Substrate | Lap Shear strength (MPa) | Failure |
|---|---|---|
| Oak | 2.5 ± 0.5 | Cohesive |
| Aluminum | 1.4 ± 0.3 | Cohesive |

Example 10. Analysis of Triacylglycerol (TAG) Composition of Algal Oils

Figure 21:
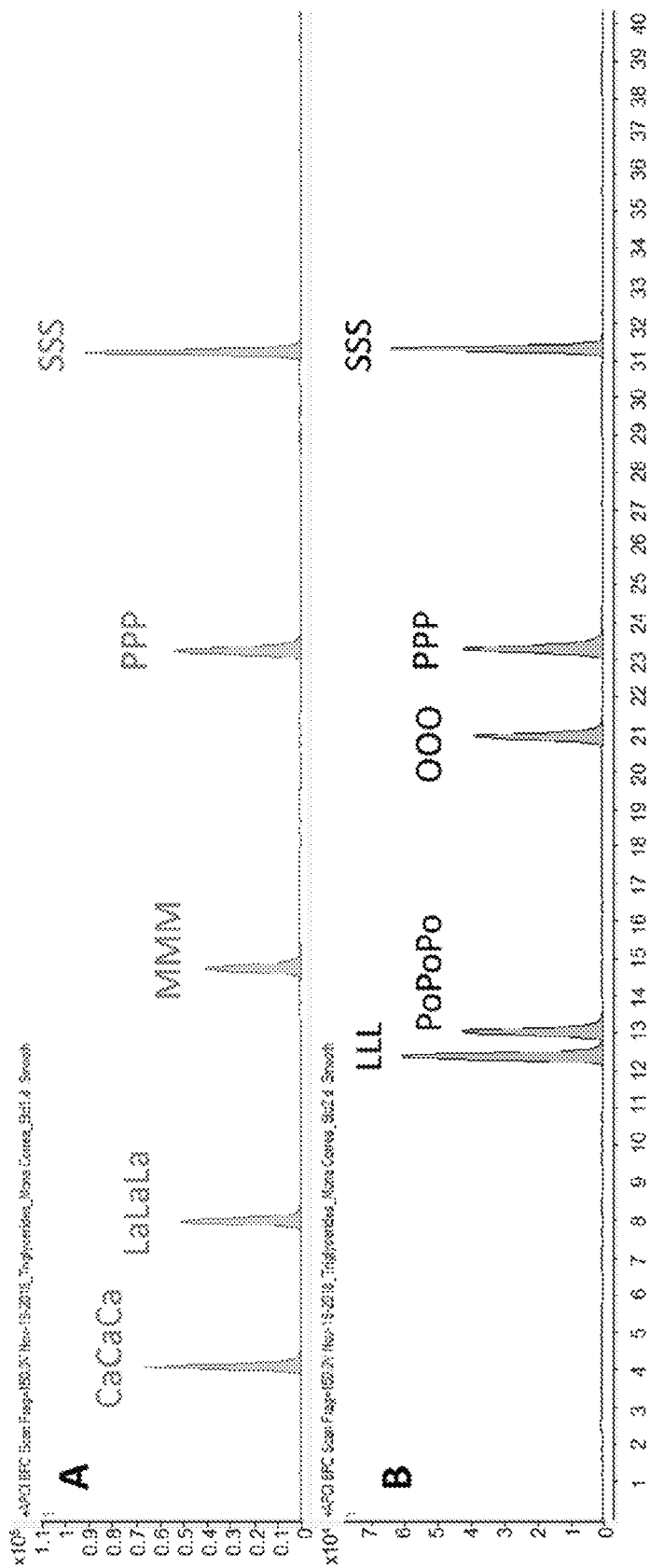
FIG. 21 illustrates LC chromatograms of TAG standards with TAGs as confirmed by MS.

To assess the diversity of TAG present in triglyceride oils, samples were analyzed by LC/TOF-MS (Liquid Chromatography/Time of Flight-Mass Spectroscopy). Fractionation was carried out on a C18 column (Shimadzu Shim-pack XR-ODS III 2.2 µm, 2.0×200 mm) followed by interrogation of individual peaks on an Agilent TOF LC-MS equipped with an APCI (Atmospheric Pressure Chemical Ionization) source. As shown in FIG. 21, NuChek reference standards 51A (A) and 54A (B) showed excellent baseline resolution of peaks and concordance of TAG species and retention times on the LC column (PPP and SSS were common between the two standards).

LC TAG standards from NuChek were run on a Shimadzu Shim-pack XR-ODS III 2.2 µm, 2.0×200 mm column and confirmed by MS on an Agilent TOF LC-MS equipped with an APCI ionization source. The TAG standard in FIG. 21, Panel A comprised of equal mass amounts of tricaprin, trilaurin, trimyristin, tripalmitin, and tristearin (CaCaCa, LaLaLa, MMM, PPP, and SSS, respectively). The TAG standard in FIG. 21, Panel B comprised of equal mass amounts of tripalmitin, tripalmitolein, triolein, tristearin, and trilinolein (PPP, PoPoPo, SSS, OOO, and LLL, respectively).

Compared to the algal oils, soybean oil has a more diverse TAG population. TABLE 14 shows the fatty acid profiles of soybean oil, mid oleic algal oil, and high oleic algal oil, showing various types of fatty acid methyl esters (FAME), as determined by GC/FID. The TAG profile of mid oleic algal oil and high oleic algal oil are shown in TABLE 15.

Figure 22:
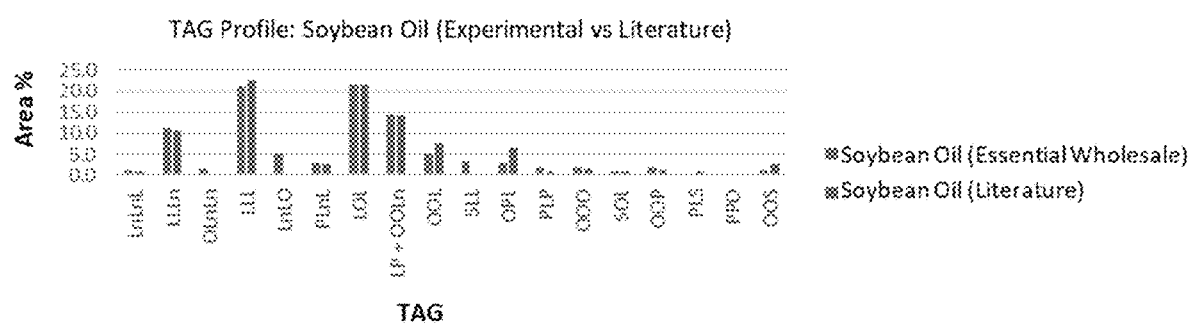
FIG. 22 illustrates liquid chromatography-mass spectrometry (LC-MS) data for soybean oil (experimental data versus literature data).

The soybean TAG profile (Essential Wholesale, left bars) shown in FIG. 22 was generated as described for NuChek standards. This TAG profile was compared to the TAG profile generated in the literature (Literature, right bars) and there was excellent concordance between the results. Literature values were obtained from W. E. Neff and W. C.

Byrdwell, Soybean Oil Triacylglycerol Analysis by Reversed-Phase High-Performance Liquid Chromatography Coupled with Atmospheric Pressure Chemical Ionization Mass Spectrometry, JAOCS, Vol. 72, no. 10 (1995). Ln, linolenic; L, linoleic; P, palmitate; O, oleic; S, stearate.

TABLE 14

Soybean Oil

| FAME | C16:0 | C16:1 | C18:0 | C18:1 | C18:2 | C18:3 | C20:0 | C20:1 | C20:2 | C24:0 |
|---|---|---|---|---|---|---|---|---|---|---|
| Area % | 11.08 | 0.11 | 4.06 | 22.89 | 52.05 | 6.87 | 0.41 | 0.28 | 0.38 | 0.11 |

Mid Oleic Algal Oil (65% oleic content)

| FAME | C14:0 | C16:1 | C18:0 | C18:1 | C18:2 | C18:3 | C20:0 |
|---|---|---|---|---|---|---|---|
| Area % | 0.92 | 18.91 | 4.22 | 65.48 | 8.80 | 0.14 | 0.52 |

High Oleic Algal Oil (88% oleic content)

| FAME | C14:0 | C16:1 | C18:0 | C18:1 | C18:2 | C18:3 | C20:0 |
|---|---|---|---|---|---|---|---|
| Area % | 0.42 | 2.06 | 0.90 | 88.34 | 6.08 | 0.34 | 0.10 |

TABLE 15

| TAG | Mid Oleic Algal Oil (65%) | High Oleic Algal Oil (88%) |
|---|---|---|
| LLL | — | 0.9 |
| OLL | — | 1.2 |
| LOL | 1.8 | — |
| PLL | 0.8 | — |
| OOL | 8.3 | 6.5 |
| POL | 4.5 | — |
| OOM + POL | 1.0 | — |
| PPL | 0.9 | — |
| OOO | 37.9 | 86.2 |
| OOP | 24.6 | 2.9 |
| POP | 9.7 | — |
| OOS | 8.1 | 1.3 |
| OOG | — | 1.0 |
| POS | 2.5 | — |
| Total | 100.0 | 100.0 |

Figure 23:
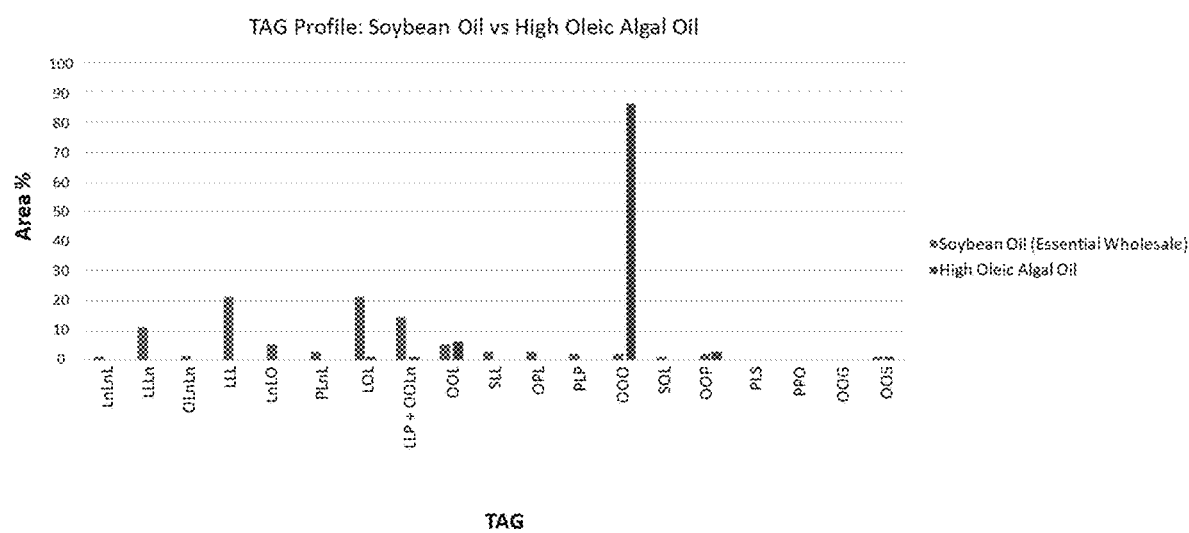
FIG. 23 illustrates LC-MS data for soybean oil (experimental data) and high oleic algal oil.

FIG. 23 shows a comparison between soybean oil (from FIG. 22; Essential Wholesale) and the high oleic algal oil (from Examples 1-9). Soybean oil had 16 TAG species comprising greater than 1% of TAGs, whereas the high oleic algal oil had only 4 TAG species with triolein (OOO) representing over 86% of all TAG species.

TAGs were resolved on a Shimadzu Shim-pack XR-ODS III 2.2µ, 2.0×200 mm column and confirmed by MS on an Agilent TOF LC-MS equipped with an APCI ionization source. G, gondoic; Ln, linolenic; L, linoleic; P, palmitate; O, oleic; S, stearate.

Example 11. The Effect of Hydrogenation Pressure on Polyol Physical Properties During Hydroformylation and Hydrogenation Reactions, as Assessed by GPC and OH #

Reaction conditions with regard to catalyst type and loading were identical to the conditions described in Example 1. Hydrogenation pressures of 600, 800, 900 (standard operating pressure), and 1200 psi were assessed for effects on the resultant polyols, as listed in TABLE 16. All polyols from this experiment had essentially identical OH # (171-173 mg KOH/g; theoretical value was 175).

TABLE 16

| Run | High Oleic Algal oil | Hydroformylation Pressure | Temp. | Time | Hydrogenation Pressure | Temp. | Time | OH# |
|---|---|---|---|---|---|---|---|---|
| Polyol-1 | 100 g | 1000 psi | 90° C. | 3.5 hrs | 600 psi | 110° C. | 2.5 hrs | 173 |
| Polyol-2 | | | | | 800 psi | | | 171 |
| Polyol-3 | | | | | 900 psi | | | 173 |
| Polyol-4 | | | | | 1200 psi | | | 172 |

Figure 24:
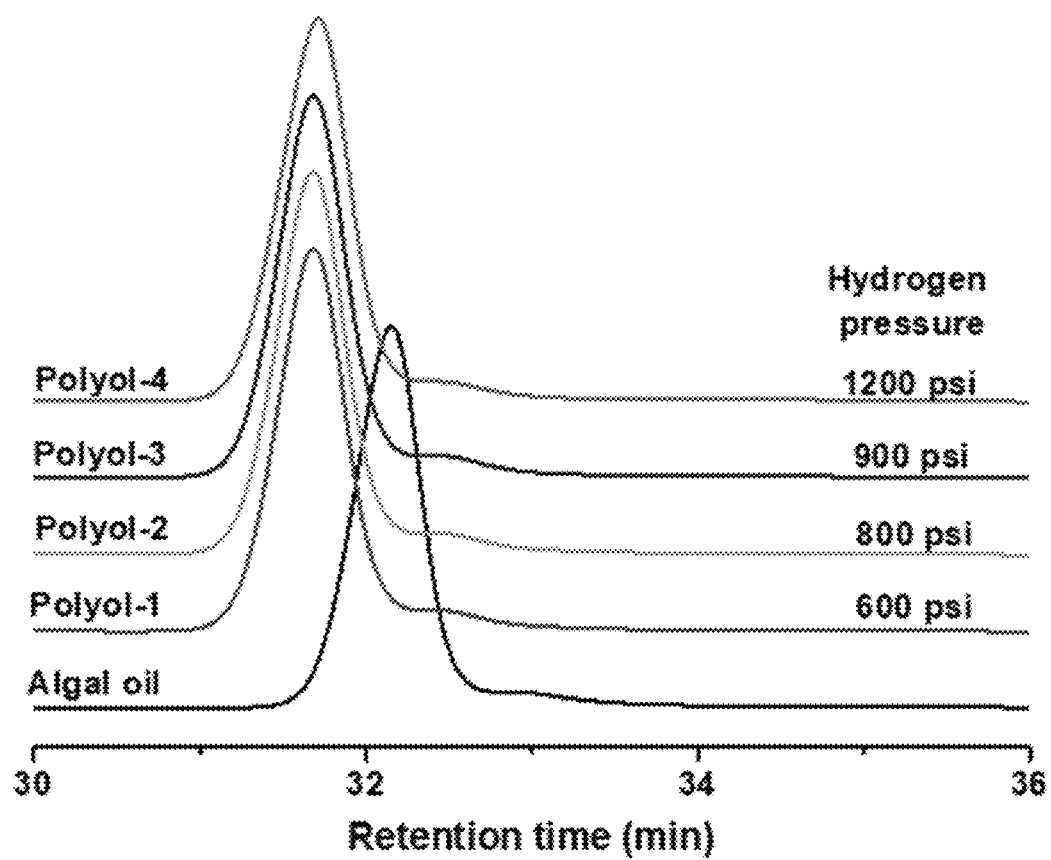
FIG. 24 illustrates GPC curves for the hydroformylation/hydrogenation reaction of polyols at various pressures.

GPC was carried out on the four polyols to assess whether there were any differences in MWs. There were no significant differences in MW among the polyols since the retention times were essentially the same for each, as shown in FIG. 24. These data, coupled with the OH # data shown in TABLE 16, indicate that a wide range of hydrogenation pressures can produce an essentially indistinguishable product.

Example 12. The Effect of Hydrogenation Pressure on Polyol Physical Properties During Hydroformylation and Hydrogenation Reactions with Varying Temperature and Pressure Regimes, as Assessed by GPC and OH #

Figure 25:
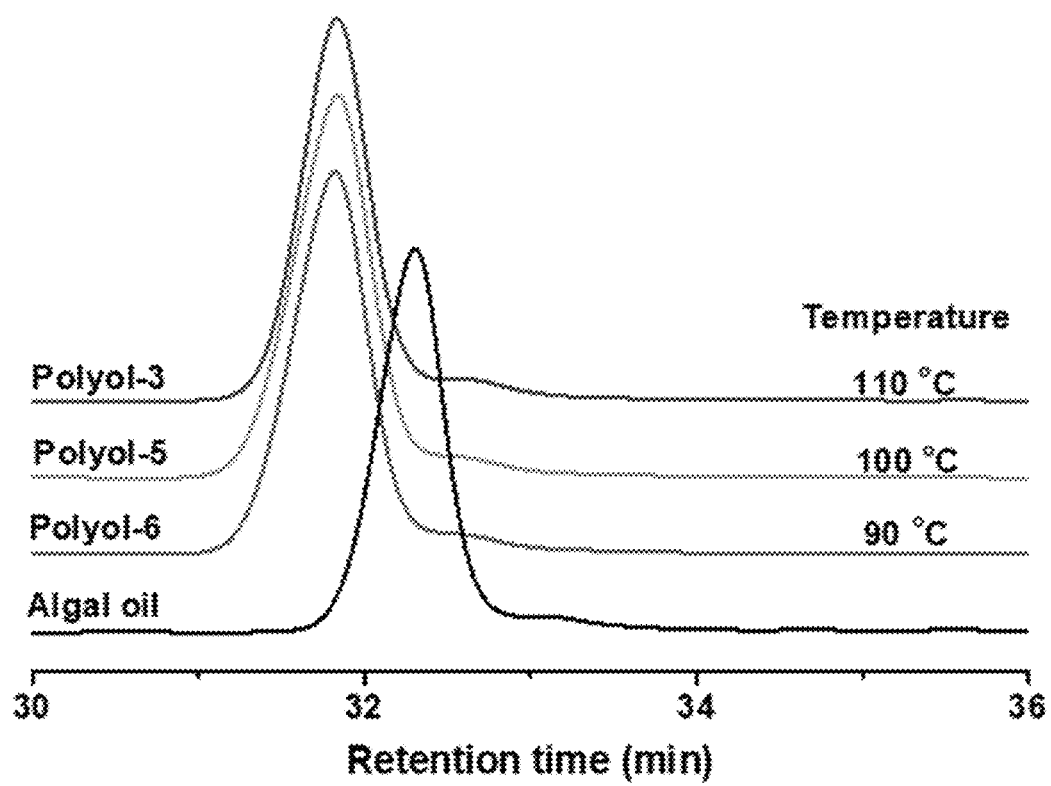
FIG. 25 illustrates GPC curves for the hydroformylation/hydrogenation reaction of polyols at various pressures and temperatures.

Three temperature/pressure regimes during the hydrogenation step were used to assess the impact on polyol OH # and MW. The standard pressure (900 psi) and temperature (110° C.) with two lower temperature regimes of 100° C. and 90° C. were compared. Both temperatures were carried out at 1000 psi operating pressure, as described in TABLE 17. Again, polyols from this experiment had essentially identical OH # (170-173 mg KOH/g, compared with a theoretical value of 175) and similar chromatographic behavior when assessed by GPC (FIG. 25), indicating that a range of hydrogenation temperatures results in polyols with equivalent functionalities and MW, respectively.

TABLE 17

| Run | High Oleic Algal oil | Hydroformylation Pressure | Temp. | Time | Hydrogenation Pressure | Temp. | Time | OH# |
|---|---|---|---|---|---|---|---|---|
| Polyol-3 | 100 g | 1000 psi | 90° C. | 3.5 hrs | 900 psi | 110° C. | 2.5 hrs | 173 |
| Polyol-5 | | | | | 1000 psi | 100° C. | | 172 |
| Polyol-6 | | | | | | 90° C. | | 170 |

Example 13. The Effect of Hydrogenation Pressure on Polyol Physical Properties During Hydroformylation and Hydrogenation Reactions at 1000 Psi and 100° C., as Assessed by GPC and OH#

Figure 26:
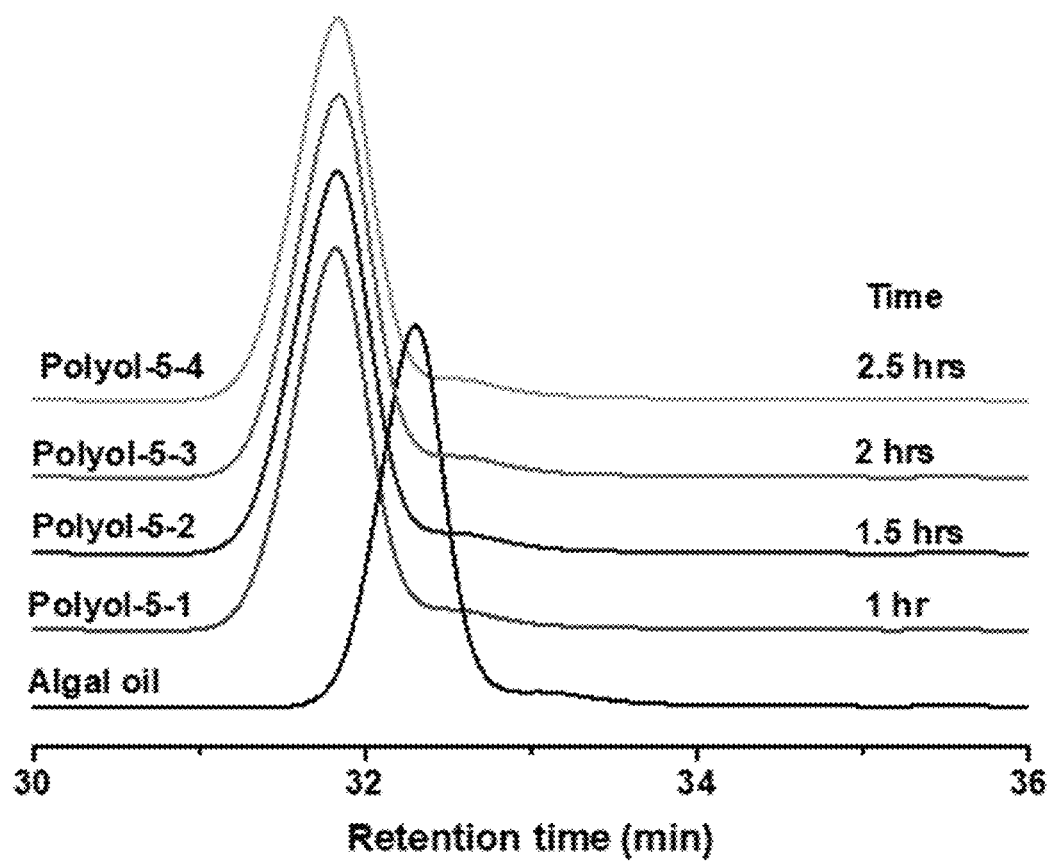
FIG. 26 illustrates GPC curves for the hydroformylation/hydrogenation reaction progress from 1 to 2.5 hours.

The effect of hydrogenation time was assessed under the reaction conditions used to generate Polyol-5 (1000 psi, 100° C.), as described in TABLE 18. Samples were withdrawn from the vessel over a time course ranging from 1 to 2.5 hrs. Again, no substantive differences in OH # (171 versus 172 in TABLE 18) or MW of the polyols (FIG. 26) were observed.

TABLE 18

| Run | High Oleic Algal oil | Hydroformylation Pressure | Temp. | Time | Hydrogenation Pressure | Temp. | Time | OH# |
|---|---|---|---|---|---|---|---|---|
| Polyol-5-1 | 100 g | 1000 psi | 90° C. | 3.5 hrs | 1000 psi | 100° C. | 1 hr | 171 |
| Polyol-5-2 | | | | | | | 1.5 hrs | 174 |

TABLE 18-continued

| | High Oleic | Hydroformylation | | | Hydrogenation | | | |
|---|---|---|---|---|---|---|---|---|
| Run | Algal oil | Pressure | Temp. | Time | Pressure | Temp. | Time | OH# |
| Polyol-5-3 | | | | | | | 2 hrs | 172 |
| Polyo-5-4 | | | | | | | 2.5 hrs | 172 |

Example 14. The Effect of Hydrogenation Pressure on Polyol Physical Properties During Hydroformylation and Hydrogenation Reactions Using Different Substrates at Varying Times, as Assessed by GPC and OH #

In these experiments, relative levels of oil to catalysts and solvents (e.g. isopropyl alcohol, IPA) in the hydroformylation and hydrogenation reactions were kept constant. Hydroformylation and hydrogenation pressures were kept constant at 1000 psi. Hydroformylation and hydrogenation temperatures were also kept constant at 90° C. and 100° C., respectively. As described in TABLE 19, hydroformylation times of 5 and 6 hours, followed by 2-5 hours of hydrogenation resulted in polyols with comparable OH #s (158-163). Reduced hydroformylation times (2 and 4 hours) resulted in significantly lower OH #s.

TABLE 19

| | Hydroformylation (HF) | | Hydrogenation (H) | | OH# |
|---|---|---|---|---|---|
| Run | Conditions | Time (h) | Conditions | Time (h) | mg KOH/g |
| 1 | 1000 psi, 90° C., Oil:Rh:TPP = 1000:1:182 | 5 | 1000 psi, 100° C., Oil:Ni:IPA = 10:1:4 | 1 | 154 |
| | | | | 2.5 | 160 |
| | | | | 3 | 163 |
| 2 | | 6 | | 1 | 122 |
| | | | | 2 | 159 |
| | | | | 3 | 159 |
| | | | | 4 | 158 |
| | | | | 5 | 158 |
| 3 | | 2 | | 1 | 105 |
| | | | | 2 | 99 |
| | | | | 3 | 97 |
| 4 | | 4 | | 1 | 142 |
| | | | | 2 | 144 |
| | | | | 3 | 142 |

Example 15. Hydroformylation Reaction Progress by FT-IR

Figure 27:
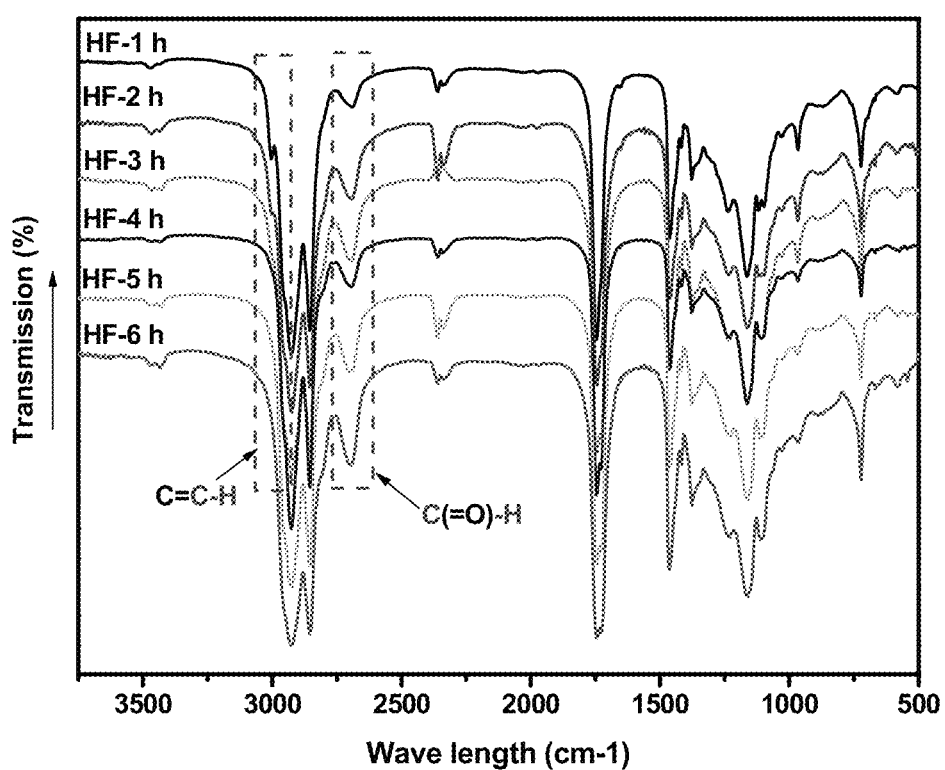
FIG. 27 illustrates the FT-IR spectra for the hydroformylation reaction progress.

The hydroformylation reaction was assessed using FT-IR. Reaction conditions (catalyst loading, pressure, and temperature) for hydroformylation were identical to the conditions described in Example 14. With increasing hydroformylation reaction time, the C=C=H signal at 3005 cm$^{-1}$ decreased and the aldehyde signal at 2700 cm$^{-1}$ increased, as denoted in FIG. 27. These data indicate that the hydroformylation reaction is generally complete at about 5 hours. At shorter reactions times (<5 hours), there is less pronounced development of the hydroformylated product, particularly as indicated by the less pronounced aldehyde peaks at 2700 cm$^{-1}$.

Example 16. Generation and Characterization of a Polyol Derived from Algal Oil with Oleic Content of 63%

Hydroformylation was carried out, as described in Example 1, using algal oil derived from *P. moriformis* microalgae. The fatty acid profile of the algal oil is shown in TABLE 20. The resulting polyol was characterized by OH # and viscosity (TABLE 21).

TABLE 20

| Fatty Acid | % Content in Algal Oil |
|---|---|
| C14:0 | 1.00 |
| C16:0 | 19.05 |
| C16:1 | 0.35 |
| C18:0 | 5.08 |
| C18:1 | 63.52 |
| C18:2 | 9.28 |
| C18:3 | 0.27 |

TABLE 21

| Polyol | OH# (mg KOH/g) | Viscosity @ 25° C. (Pa · S) |
|---|---|---|
| Method | IUPAC 2.241 | Rheometer |
| HF-H-AO-63%-1 | 141 | 1.4 |

Figure 28:
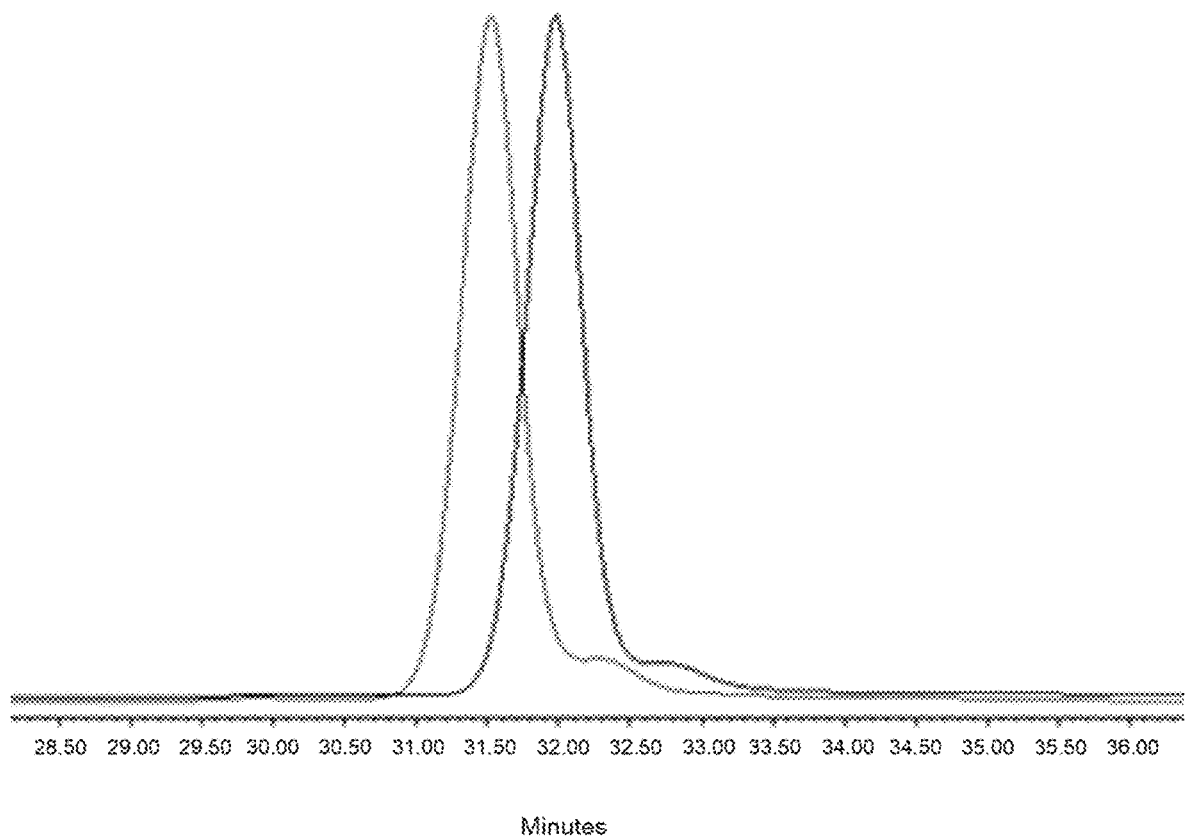
FIG. 28 illustrates GPC curves for the starting algal oil with oleic content of 63% and the hydroformylated polyol.

GPC was carried out to further characterize the polyol and compare the MW of the polyol and that of the starting algal oil. The hydroformylated polyol (blue curve; left) eluted earlier than the native algal oil triglyceride (black curve; right), which is consistent with the increase in molecular weight of the polyol (FIG. 28).

Example 17. Generation and Characterization of a Polyol Derived from Algal Oil with Oleic Content of 74%

Hydroformylation was carried out, as described in Example 1, using algal oil derived from *P. moriformis* microalgae. The fatty acid profile of the algal oil is shown in TABLE 22. The resulting polyol was characterized by OH #, viscosity, and GPC.

TABLE 22

| Fatty Acid | % Content in Algal Oil |
|---|---|
| C14:0 | 0.64 |
| C16:0 | 12.18 |
| C16:1 | 0.38 |
| C18:0 | 3.55 |
| C18:1 | 74.31 |
| C18:2 | 7.66 |
| C18:3 | 0.11 |

Figure 29:
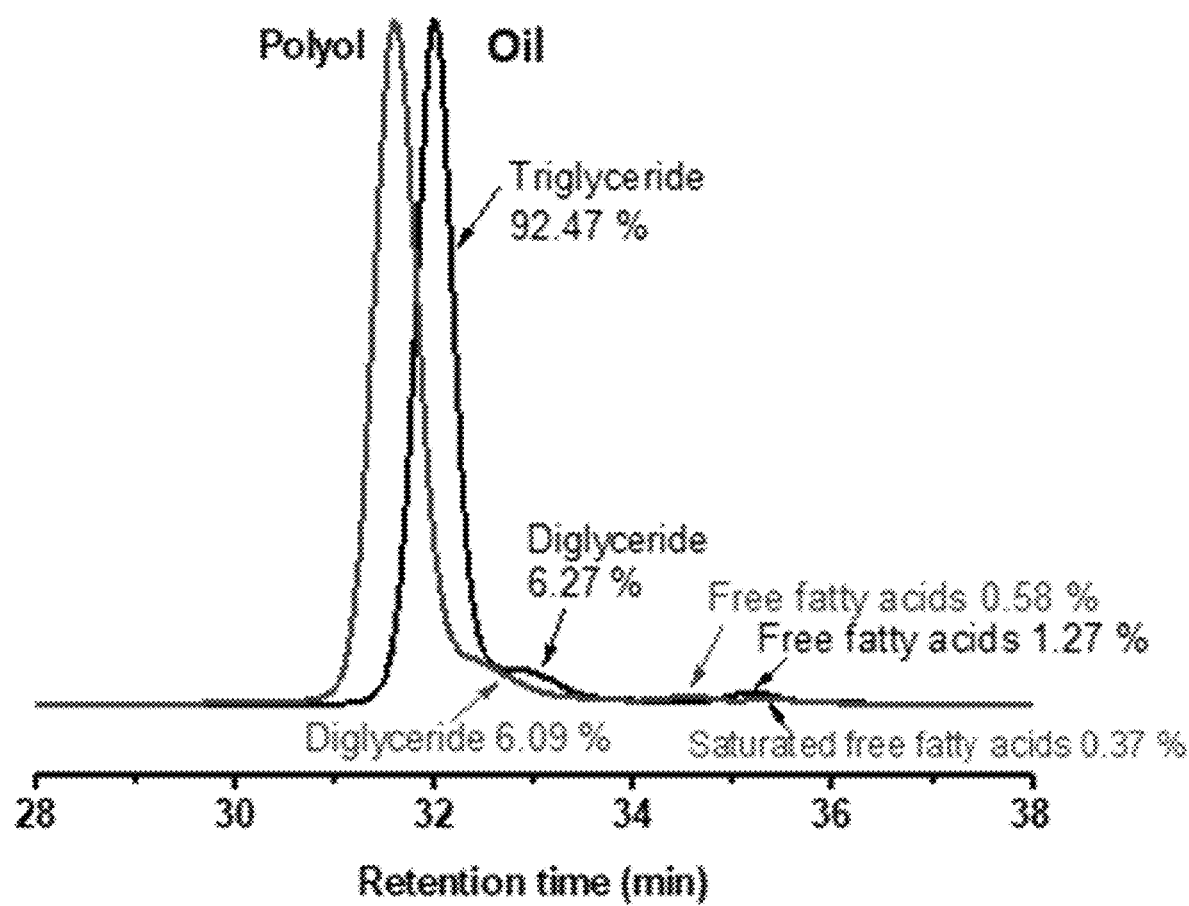
FIG. 29 illustrates GPC curves for the starting algal oil with oleic content of 74% and the hydroformylated polyol.

Properties of the final polyol are listed in TABLE 23. The GPC traces of the algal polyol and starting oil are shown in FIG. 29. The hydroformylated polyol (red curve; left) eluted earlier than the native algal oil triglyceride (black curve; right), which is consistent with the increase in molecular weight of the polyol.

TABLE 23

| Property | OH# (mg KOH/g) | Viscosity @ 25° C. (Pa · S) |
|---|---|---|
| Method | IUPAC 2.241 | Rheometer |
| Polyol | 152 | 1.79 |

Example 18. Generation and Characterization of a Polyol Derived from Algal Oil with Oleic Content of 75%

Hydroformylation was carried out, as described in Example 1, using algal oil derived from *P. moriformis* microalgae. The fatty acid profile of the algal oil is shown in TABLE 24. The resulting polyol was characterized by OH #, viscosity, and GPC.

TABLE 24

| Fatty Acid | % Content in Algal Oil |
|---|---|
| C14:0 | 0.69 |
| C16:0 | 11.48 |
| C16:1 | 0.38 |
| C18:0 | 3.37 |
| C18:1 | 75.11 |
| C18:2 | 7.69 |
| C18:3 | 0.11 |

Figure 30:
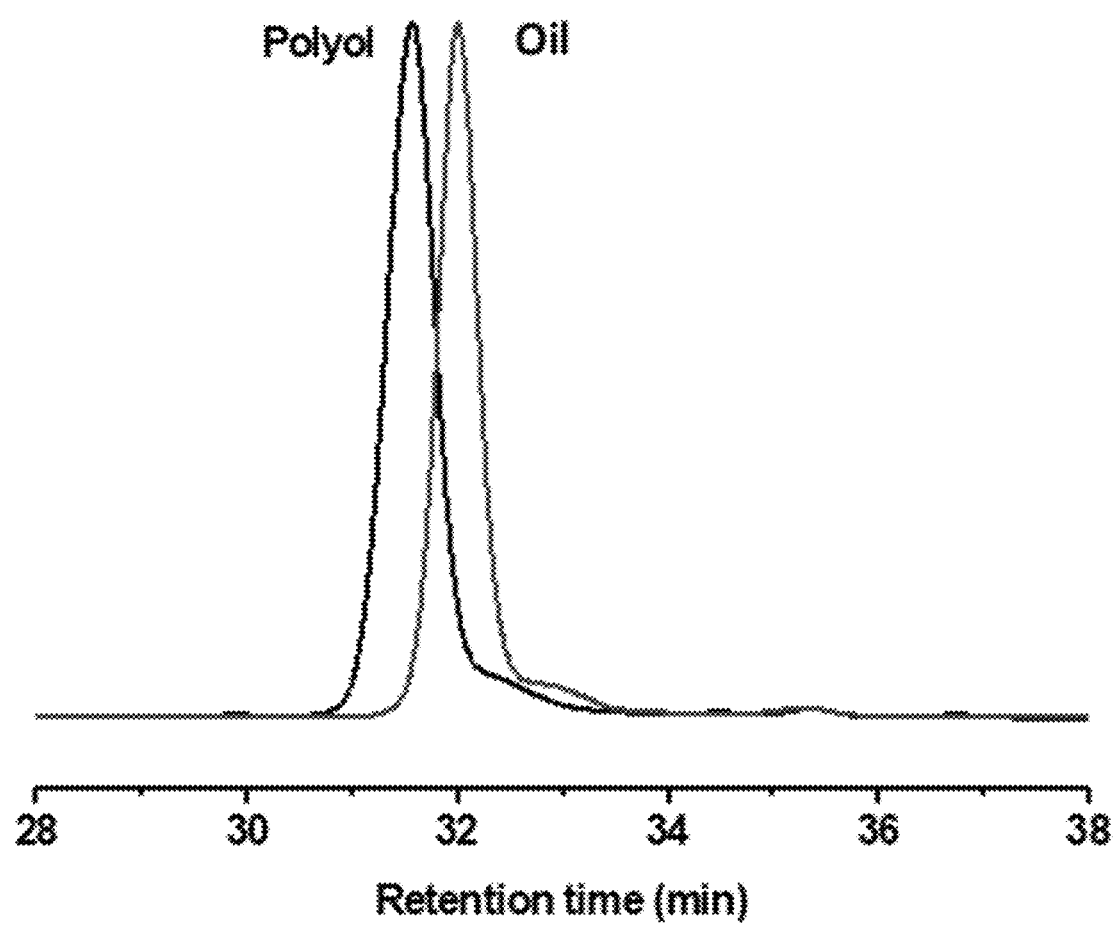
FIG. 30 illustrates GPC curves for the starting algal oil with oleic content of 75% and the hydroformylated polyol.

Properties of the final polyol are listed in TABLE 25. The GPC traces of the algal polyol and starting oil are shown in FIG. 30. The hydroformylated polyol (red curve; left) eluted earlier than the native algal oil triglyceride (black curve; right), which is consistent with the increase in molecular weight of the polyol.

TABLE 25

| Property | OH# (mg KOH/g) | Viscosity @ 25° C. (Pa · S) |
|---|---|---|
| Method | IUPAC 2.241 | Rheometer |
| Polyol | 155 | 1.6 |

Example 19. Generation and Characterization of a Polyol Derived from Algal Oil with Oleic Content of 85%

Hydroformylation was carried out, as described in Example 1, using algal oil derived from *P. moriformis* microalgae. The fatty acid profile of the algal oil is shown in TABLE 26. The resulting polyol was characterized by OH #, viscosity, and GPC.

TABLE 26

| Fatty Acid | % Content in Algal Oil |
|---|---|
| C14:0 | 0.44 |
| C16:0 | 4.32 |
| C16:1 | 0.15 |
| C18:0 | 1.75 |
| C18:1 | 84.76 |
| C18:2 | 6.90 |
| C18:3 | 0.10 |

Figure 31:
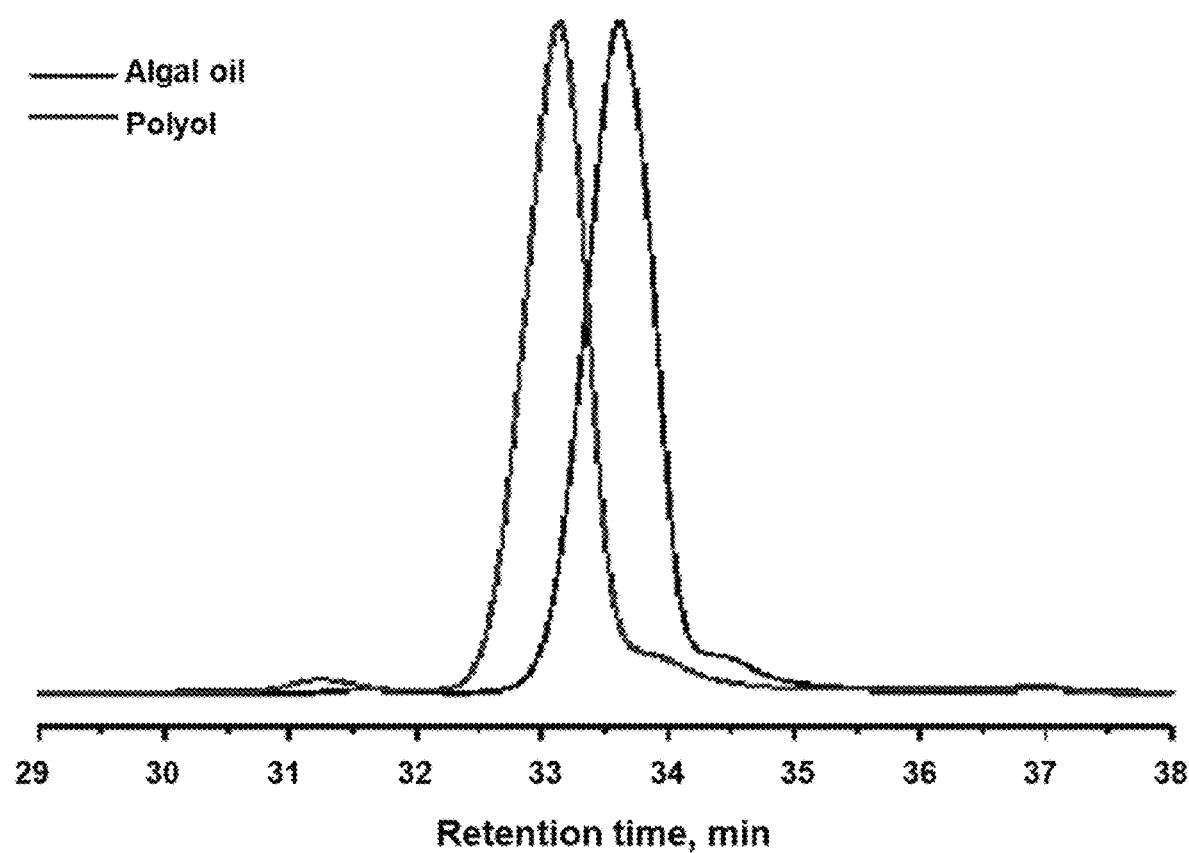
FIG. 31 illustrates GPC curves for the starting algal oil with oleic content of 85% and the hydroformylated polyol.

Properties of the final polyol are listed in TABLE 27. The GPC curves of the algal polyol and starting oil are shown in FIG. 31. The hydroformylated polyol (red curve; left) eluted earlier than the native algal oil triglyceride (black curve; right), which is consistent with the increase in molecular weight of the polyol.

TABLE 27

| | OH# (mg KOH/g) | Viscosity @ 25° C. (Pa · S) |
|---|---|---|
| Method | IUPAC 2.241 | Rheometer |
| Polyol | 157.4 | 1.926 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of producing a hydroformylated polyol, comprising:
   a) obtaining a microbial oil comprising triacylglycerol (TAG) species having a fatty acid profile comprising at least 60% of one or more unsaturated fatty acids, and wherein said microbial oil comprises 30% or more of triolein; and
   b) hydroformylating and hydrogenating said microbial oil, thereby generating said hydroformylated polyol.

2. The method of claim 1, wherein said microbial oil comprises up to nine TAG species, wherein each of said up to nine TAG species is in an amount of at least 1%.

3. The method of claim 1, wherein said microbial oil comprises up to five TAG species, wherein each of said up to five TAG species is in an amount of at least 1%.

4. The method of claim 1, wherein said microbial oil comprises up to four TAG species, wherein each of said up to four TAG species is in an amount of at least 1%.

5. The method of claim 1, wherein said microbial oil comprises up to three TAG species, wherein each of said up to three TAG species is in an amount of at least 1%.

6. The method of claim 1, wherein said microbial oil comprises 60% or more of a TAG species.

7. The method of claim 1, wherein said microbial oil comprises 80% or more of a TAG species.

8. The method of claim 1, wherein said microbial oil comprises 80% or more of triolein.

9. The method of claim 1, wherein said microbial oil comprises C14:0 in an amount of up to 1%, C16:1 in an amount of up to 19%, C18:0 in an amount of up to 5%, C18:1 in an amount of more than 60%, and C18:2 in an amount of up to 10%.

10. The method of claim 1, wherein said microbial oil comprises C14:0 in an amount of up to 1%, C16:1 in an amount of up to 5%, C18:0 in an amount of up to 1%, C18:1 in an amount of more than 80%, and C18:2 in an amount of up to 10%.

11. The method of claim 1, wherein said hydroformylated polyol has a hydroxyl number of 90 to 190.

12. The method of claim 1, wherein said hydroformylated polyol has a hydroxyl number of 150 to 160.

13. The method of claim 1, wherein said hydroformylated polyol has a hydroxyl number of 160 to 165.

14. The method of claim 1, wherein said hydroformylated polyol has a hydroxyl number of 170 to 175.

15. A method of producing a polyurethane cast resin, comprising reacting said hydroformylated polyol of claim 1 with an isocyanate, thereby generating said polyurethane cast resin.

16. A method of producing a polyurethane foam, comprising reacting said hydroformylated polyol of claim 1 with an isocyanate and a blowing agent, thereby generating said polyurethane foam.

17. A method of producing a polyurethane adhesive, comprising reacting said hydroformylated polyol of claim 1 with an isocyanate, thereby generating said polyurethane adhesive.

18. A method of producing a hydroformylated polyol, comprising:
   a) obtaining a microbial oil comprising up to nine TAG species present in amounts of 1% or more in said microbial oil, wherein said up to nine TAG species present in amounts of 1% or more have a fatty acid profile comprising at least 60% of one or more unsaturated fatty acids, and wherein said microbial oil comprises C14:0 in an amount of up to 1%, C16:1 in an amount of up to 19%, C18:0 in an amount of up to 5%, C18:1 in an amount of more than 60%, and C18:2 in an amount of up to 10%; and
   b) hydroformylating and hydrogenating said at least 60% of one or more unsaturated fatty acids, thereby generating said hydroformylated polyol.

19. A method of producing a hydroformylated polyol, comprising:
   a) obtaining a microbial oil comprising 30% or more of triolein and up to nine TAG species present in amounts of 1% or more in said microbial oil, wherein said up to nine TAG species present in amounts of 1% or more have a fatty acid profile comprising at least 60% of oleic acid; and
   b) hydroformylating and hydrogenating said microbial oil, thereby generating said hydroformylated polyol.

20. A method of producing a hydroformylated polyol, comprising:
   a) obtaining a microbial oil comprising triacyglycerol (TAG) species having a fatty acid profile comprising at least 60% of one or more unsaturated fatty acids, and wherein said microbial oil comprises C14:0 in an amount of up to 1%, C16:1 in an amount of up to 19%, C18:0 in an amount of up to 5%, C18:1 in an amount of more than 60%, and C18:2 in an amount of up to 10%; and
   b) hydroformylating and hydrogenating said microbial oil, thereby generating said hydroformylated polyol.

* * * * *